US010046942B2

(12) United States Patent
Beers et al.

(10) Patent No.: US 10,046,942 B2
(45) Date of Patent: Aug. 14, 2018

(54) MOTORIZED TENSIONING SYSTEM WITH SENSORS

(71) Applicant: NIKE, Inc., Beaverton, OR (US)

(72) Inventors: Tiffany A. Beers, Portland, OR (US); Andrew A. Owings, Portland, OR (US); Cody Collier Henderson, Denver, CO (US); James Alan Capra, Steamboat Springs, CO (US); Mark Stanley Soderberg, Conifer, CO (US); Daniel Hipwood, Denver, CO (US)

(73) Assignee: NIKE, Inc., Beaverton, OR (US)

( * ) Notice: Subject to any disclaimer, the term of this patent is extended or adjusted under 35 U.S.C. 154(b) by 213 days.

(21) Appl. No.: 15/171,500

(22) Filed: Jun. 2, 2016

(65) Prior Publication Data

US 2016/0272458 A1 Sep. 22, 2016

Related U.S. Application Data

(62) Division of application No. 14/014,555, filed on Aug. 30, 2013, now Pat. No. 9,365,387.

(Continued)

(51) Int. Cl.
| | |
|---|---|
| *A43B 11/00* | (2006.01) |
| *B65H 59/38* | (2006.01) |
| *A43C 11/00* | (2006.01) |
| *A43C 11/16* | (2006.01) |
| *A43B 3/00* | (2006.01) |

(Continued)

(52) U.S. Cl.
CPC .......... *B65H 59/384* (2013.01); *A43B 3/0005* (2013.01); *A43B 3/0015* (2013.01); *A43B 11/00* (2013.01); *A43C 11/00* (2013.01); *A43C 11/008* (2013.01); *A43C 11/165* (2013.01); *A61F 5/028* (2013.01); *B65H 59/00* (2013.01)

(58) Field of Classification Search
CPC ....... B65H 59/00; B65H 59/384; A43B 11/00; A43B 3/0005; A43B 3/0015; A61F 5/028; A43C 11/00; A43C 11/008; A43C 11/165
See application file for complete search history.

(56) References Cited

U.S. PATENT DOCUMENTS

| | | |
|---|---|---|
| 1,702,583 A | 2/1929 | Williams |
| 1,916,483 A | 7/1933 | Krichbaum |

(Continued)

FOREIGN PATENT DOCUMENTS

| | | |
|---|---|---|
| CN | 1061706 A | 6/1992 |
| CN | 1550166 A | 12/2004 |

(Continued)

OTHER PUBLICATIONS

Blake Bevin, Power Laces Prototype Version 1, Uploaded Jul. 4, 2010 http://www.youtube.com/watch?v=ROEZsOHpFQc&feature=endscreen&NR=1.

(Continued)

*Primary Examiner* — Sang K Kim
(74) *Attorney, Agent, or Firm* — Schwegman Lundberg & Woessner, P.A.

(57) ABSTRACT

A tensioning system for articles of footwear and articles of apparel is disclosed. The tensioning system includes a tensioning member that is tightened or loosened using a motorized tensioning device for winding and unwinding the tensioning member on a spool. The tensioning system may be used with various sensors to determine how the motorized tensioning device should be controlled.

20 Claims, 43 Drawing Sheets

Related U.S. Application Data

(60) Provisional application No. 61/695,953, filed on Aug. 31, 2012.

(51) Int. Cl.
*A61F 5/02* (2006.01)
*B65H 59/00* (2006.01)

(56) References Cited

U.S. PATENT DOCUMENTS

| | | | |
|---|---|---|---|
| 3,187,342 A | 6/1965 | Aileo |
| 3,430,303 A | 3/1969 | Donald et al. |
| 3,549,878 A | 12/1970 | Richard |
| 3,859,496 A | 1/1975 | Giese |
| 4,011,634 A | 3/1977 | Olivieri |
| 4,020,571 A | 5/1977 | Olivieri |
| 4,037,333 A | 7/1977 | Olivieri |
| 4,090,278 A | 5/1978 | Olivieri |
| 4,130,949 A | 12/1978 | Seidel |
| 4,253,217 A | 3/1981 | Marzocchi |
| 4,310,951 A | 1/1982 | Riedel |
| 4,326,320 A | 4/1982 | Riedel |
| 4,424,636 A | 1/1984 | Everest |
| 4,433,456 A | 2/1984 | Baggio |
| 4,453,290 A | 6/1984 | Riedel |
| 4,619,057 A | 10/1986 | Sartor et al. |
| 4,697,360 A | 10/1987 | Sartor |
| 4,724,626 A | 2/1988 | Baggio |
| 4,741,115 A | 5/1988 | Pozzobon |
| 4,780,968 A | 11/1988 | Bragagnolo |
| 4,787,124 A | 11/1988 | Pozzobon et al. |
| 4,800,659 A | 1/1989 | Marega |
| 4,802,290 A | 2/1989 | Marega |
| 4,841,649 A | 6/1989 | Baggio et al. |
| 4,942,678 A | 7/1990 | Gumbert |
| 5,105,566 A | 4/1992 | Legon |
| 5,129,130 A | 7/1992 | Lecouturier |
| 5,157,813 A | 10/1992 | Carroll |
| 5,341,583 A | 8/1994 | Hallenbeck |
| 5,381,609 A | 1/1995 | Hieblinger |
| 5,425,185 A | 6/1995 | Gansler |
| 5,456,393 A | 10/1995 | Mathis et al. |
| 5,467,537 A | 11/1995 | Aveni et al. |
| 5,469,640 A | 11/1995 | Nichols |
| 5,495,682 A | 3/1996 | Chen |
| 5,555,650 A | 9/1996 | Longbottom et al. |
| 5,692,324 A | 12/1997 | Goldston et al. |
| 5,755,044 A | 5/1998 | Veylupek |
| 5,791,068 A | 8/1998 | Bernier et al. |
| 5,836,899 A | 11/1998 | Reilly |
| 5,839,210 A | 11/1998 | Bernier et al. |
| 5,934,599 A | 8/1999 | Hammerslag |
| 6,018,890 A | 2/2000 | Bowen |
| 6,032,387 A | 3/2000 | Johnson |
| 6,052,924 A | 4/2000 | Sabat |
| 6,148,489 A | 11/2000 | Dickie et al. |
| 6,202,953 B1 | 3/2001 | Hammerslag |
| 6,289,558 B1 | 9/2001 | Hammerslag |
| 6,289,609 B1 | 9/2001 | Bowen |
| 6,427,361 B1 | 8/2002 | Chou |
| 6,449,878 B1 | 9/2002 | Lyden |
| 6,601,042 B1 | 7/2003 | Lyden |
| 6,681,504 B2 | 1/2004 | Kinan |
| 6,691,433 B2 | 2/2004 | Liu |
| 6,691,443 B1 | 2/2004 | Slayden |
| 6,751,490 B2 | 6/2004 | Esenaliev et al. |
| 6,862,820 B2 | 3/2005 | Farys et al. |
| 6,892,429 B2 | 5/2005 | Sartor et al. |
| 6,922,917 B2 | 8/2005 | Kerns et al. |
| 7,065,906 B2 | 6/2006 | Jones et al. |
| 7,103,994 B2 | 9/2006 | Johnson |
| 7,200,957 B2 | 4/2007 | Hubbard et al. |
| 7,287,342 B2 | 10/2007 | Keen |
| 7,310,895 B2 | 12/2007 | Whittlesey et al. |
| 7,367,522 B2 | 5/2008 | Chen |
| 7,503,131 B2 | 3/2009 | Nadel et al. |
| 7,584,528 B2 | 9/2009 | Hu |
| 7,591,050 B2 | 9/2009 | Hammerslag |
| 7,676,960 B2 | 3/2010 | DiBenedetto et al. |
| 7,721,468 B1 | 5/2010 | Johnson et al. |
| 7,752,774 B2 | 7/2010 | Ussher |
| 7,950,112 B2 | 5/2011 | Hammerslag et al. |
| 7,954,204 B2 | 6/2011 | Hammerslag et al. |
| 7,980,009 B2 | 7/2011 | Carnes et al. |
| 7,992,261 B2 | 8/2011 | Hammerslag et al. |
| 8,020,320 B2 | 9/2011 | Gillespie |
| 8,046,937 B2 | 11/2011 | Beers et al. |
| 8,056,269 B2 | 11/2011 | Beers et al. |
| 8,061,061 B1 | 11/2011 | Rivas |
| 8,074,379 B2 | 12/2011 | Robinson, Jr. et al. |
| 8,091,182 B2 | 1/2012 | Hammerslag et al. |
| 8,141,277 B2 | 3/2012 | Robinson et al. |
| 8,151,490 B2 | 4/2012 | Sokolowski |
| 8,231,074 B2 | 7/2012 | Hu et al. |
| 8,387,282 B2 | 3/2013 | Baker et al. |
| 8,904,673 B2 | 12/2014 | Johnson et al. |
| 9,365,387 B2 | 6/2016 | Beers et al. |
| 9,693,605 B2 | 7/2017 | Beers |
| 2002/0043007 A1 | 4/2002 | Hannah |
| 2002/0095750 A1 | 7/2002 | Hammerslag |
| 2004/0128863 A1 | 7/2004 | Hong et al. |
| 2005/0098673 A1 | 5/2005 | Huang |
| 2005/0102861 A1 | 5/2005 | Martin |
| 2006/0000116 A1 | 1/2006 | Brewer |
| 2006/0116483 A1 | 6/2006 | Tonkel |
| 2006/0156517 A1 | 7/2006 | Hammerslag et al. |
| 2006/0201031 A1 | 9/2006 | Jones et al. |
| 2007/0000105 A1 | 1/2007 | Grande et al. |
| 2007/0011914 A1 | 1/2007 | Keen et al. |
| 2007/0043630 A1 | 2/2007 | Lyden |
| 2007/0169378 A1 | 7/2007 | Sodeberg et al. |
| 2007/0278911 A1 | 12/2007 | Vallance et al. |
| 2008/0060167 A1 | 3/2008 | Hammerslag et al. |
| 2008/0066272 A1 | 3/2008 | Hammerslag et al. |
| 2008/0222917 A1 | 9/2008 | Dojan et al. |
| 2008/0235990 A1 | 10/2008 | Wegener |
| 2008/0307673 A1 | 12/2008 | Johnson |
| 2009/0055044 A1 | 2/2009 | Dienst |
| 2009/0184189 A1 | 7/2009 | Soderberg et al. |
| 2009/0205221 A1 | 8/2009 | Mitchell |
| 2009/0272007 A1 | 11/2009 | Beers et al. |
| 2010/0101116 A1 | 4/2010 | Serafino et al. |
| 2010/0139057 A1 | 6/2010 | Soderberg et al. |
| 2010/0251524 A1 | 10/2010 | Chen et al. |
| 2010/0299959 A1 | 12/2010 | Hammerslag et al. |
| 2011/0175744 A1 | 7/2011 | Englert et al. |
| 2011/0225843 A1 | 9/2011 | Kerns et al. |
| 2011/0258876 A1 | 10/2011 | Baker et al. |
| 2011/0266384 A1 | 11/2011 | Goodman et al. |
| 2012/0000091 A1 | 1/2012 | Cotterman et al. |
| 2012/0004587 A1 | 1/2012 | Nickel et al. |
| 2012/0005923 A1 | 1/2012 | Beers et al. |
| 2012/0117821 A1 | 5/2012 | Adams et al. |
| 2012/0192457 A1 | 8/2012 | Youngs |
| 2013/0312293 A1 | 11/2013 | Gerber |
| 2014/0068838 A1 | 3/2014 | Beers et al. |
| 2014/0070042 A1 | 3/2014 | Beers et al. |
| 2014/0082963 A1 | 3/2014 | Beers et al. |
| 2014/0094728 A1 | 4/2014 | Soderberg et al. |
| 2017/0295889 A1 | 10/2017 | Beers |

FOREIGN PATENT DOCUMENTS

| | | |
|---|---|---|
| CN | 102014682 A | 4/2011 |
| CN | 104822284 A | 8/2015 |
| CN | 105722419 A | 6/2016 |
| CN | 104822284 B | 10/2016 |
| CN | 106820446 A | 6/2017 |
| DE | 29817003 U1 | 3/1999 |
| DE | 19833801 A1 | 2/2000 |
| DE | 10109673 A1 | 9/2002 |
| DE | 102005036013 A1 | 2/2007 |
| EP | 1064863 A1 | 1/2001 |
| FR | 2827486 A1 | 1/2003 |

(56) References Cited

FOREIGN PATENT DOCUMENTS

| | | | |
|---|---|---|---|
| GB | 2449722 | A | 12/2008 |
| JP | 2004222782 | A | 8/2004 |
| JP | 2005036374 | A | 2/2005 |
| JP | 2005124597 | A | 5/2005 |
| JP | 2010148927 | A | 7/2010 |
| JP | 2011519611 | A | 7/2011 |
| JP | 2013529504 | A | 7/2013 |
| JP | 2016530058 | A | 9/2016 |
| WO | 0115559 | A1 | 3/2001 |
| WO | 2009071652 | A1 | 6/2009 |
| WO | 2009134858 | A1 | 11/2009 |
| WO | 2014036371 | A1 | 3/2014 |
| WO | 2014036374 | A1 | 3/2014 |

OTHER PUBLICATIONS

Blake Bevin, Power Laces Prototype Version 2, Uploaded Aug. 29, 2010 http://www.youtube.com/watch?v=k_Efr2TaEPo.
Blake Bevin, Power-Laces.com Archived, About the Project, Aug. 18, 2012.
International Preliminary Report on Patentability and Written Opinion dated Mar. 12, 2015 for International Patent Application No. PCT/US2013/057462.
International Preliminary Report on Patentability and Written Opinion dated Mar. 12, 2015 for International Patent Application No. PCT/US2013/057467.
International Search Report and Written Opinion dated Jan. 3, 2014 for International Patent Application No. PCT/US2013/057462.
International Search Report and Written Opinion dated Jan. 3, 2014 for International Patent Application No. PCT/US2013/057467.
International Search Report and Written Opinion dated Dec. 22, 2014 for International Patent Application No. PCT/US2014/056207.
International Preliminary Report on Patentability and Written Opinion dated Mar. 22, 2016 for International Patent Application No. PCT/US2014/056207.
Response to Written Opinion filed Sep. 7, 2015 in European Patent Application No. 13783413.1.
Response to Office Action filed Apr. 18, 2016 in Chinese Application No. 201380044810.0.
Notice of Allowance dated May 23, 2016 in Chinese Application No. 201380044813.4.
"U.S. Appl. No. 14/014,555, Examiner Interview Summary dated Jan. 22, 2016", 3 pgs.
"U.S. Appl. No. 14/014,555, Non Final Office Action dated Aug. 26, 2015", 8 pgs.
"U.S. Appl. No. 14/014,555, Notice of Allowance dated Feb. 17, 2016", 7 pgs.
"U.S. Appl. No. 14/014,555, Response filed Jan. 26, 2016 to Non Final Office Action dated Aug. 26, 2015", 14 pgs.
"U.S. Appl. No. 14/014,555, Response filed Aug. 14, 2015 to Restriction Requirement dated May 15, 2015", 11 pgs.
"U.S. Appl. No. 14/014,555, Restriction Requirement dated May 15, 2015", 7 pgs.
"U.S. Appl. No. 14/032,524, Examiner Interview Summary dated Mar. 3, 2016", 3 pgs.
"U.S. Appl. No. 14/032,524, Final Office Action dated May 6, 2016", 6 pgs.
"U.S. Appl. No. 14/032,524, Non Final Office Action dated Dec. 9, 2015", 11 pgs.
"U.S. Appl. No. 14/032,524, Notice of Allowance dated Jul. 26, 2016", 8 pgs.
"U.S. Appl. No. 14/032,524, Response filed Mar. 9, 2016 to Non Final Office Action dated Dec. 9, 2015", 14 pgs.
"U.S. Appl. No. 14/032,524, Response filed Jul. 6, 2016 to Final Office Action dated May 6, 2016", 11 pgs.
"U.S. Appl. No. 14/032,524, Response filed Oct. 6, 2015 to Restriction Requirement dated Aug. 7, 2015", 11 pgs.
"U.S. Appl. No. 14/032,524, Restriction Requirement dated Aug. 7, 2015", 8 pgs.
"Chinese Application Serial No. 201380044810.0, Office Action dated Dec. 2, 2015", with English translation of claims, 14 pgs.
"Chinese Application Serial No. 201380044810.0, Response filed Apr. 18, 2016 to Office Action dated Dec. 2, 2015", with English translation of claims, 21 pgs.
"European Application Serial No. 13783414.9, Response filed Sep. 7, 2015 to Communication pursuant to Rules 161(1) and 162 EPC dated Mar. 10, 2015", 14 pgs.
"European Application Serial No. 14790802.4, Response filed Nov. 3, 2016", 19 pgs.
"Japanese Application Serial No. 2016-543980, Office Action dated May 13, 2016", 87 pgs.
"U.S. Appl. No. 14/032,524 Notice of Allowance dated Nov. 23, 2016", 7 pgs.
"U.S. Appl. No. 14/032,524, Notice of Allowability dated May 22, 2017", 2 pgs.
"U.S. Appl. No. 14/032,524, Notice of Allowance dated Mar. 30, 2017", 8 pgs.
"Chinese Application Serial No. 201480062685.0, Office Action dated Mar. 2, 2017", with English translation of claims, 14 pgs.
"Chinese Application Serial No. 201480062685.0, Voluntary Amendment filed Oct. 21, 2016", with English translation of claims, 201 pgs.
"European Application Serial No. 13783414.9, Communication Pursuant to Article 94(3) EPC dated May 23, 2017", 5 pgs.
"Chinese Application Serial No. 201480062685.0, Office Action dated Sep. 15, 2017", w/ English Translation, 20 pgs.
"Chinese Application Serial No. 201480062685.0, Response filed Jul. 17, 2017 to Office Action dated Mar. 2, 2017", w/ English Translation, 8 pgs.
"Chinese Application Serial No. 201480062685.0, Response filed Dec. 22, 2017 to Office Action dated Sep. 15, 2017", claims not amended in response, attached currently pending claims to response PDF, 13 pgs.
"Japanese Application Serial No. 2016-543980, Office Action dated Jan. 25, 2018", w/ English translation, 9 pgs.
"European Application Serial No. 14790802.4, Communication Pursuant to Article 94(3) EPC dated Apr. 11, 2018", 7 pgs.
"Japanese Application Serial No. 2016-543980, Response filed Mar. 29, 2018 to Office Action dated Jan. 25, 2013", w/ English claims, 11 pgs.
"Japanese Application Serial No. 2016-543980, Office Action dated Jun. 21, 2018", w/ English translation, 8 pgs.

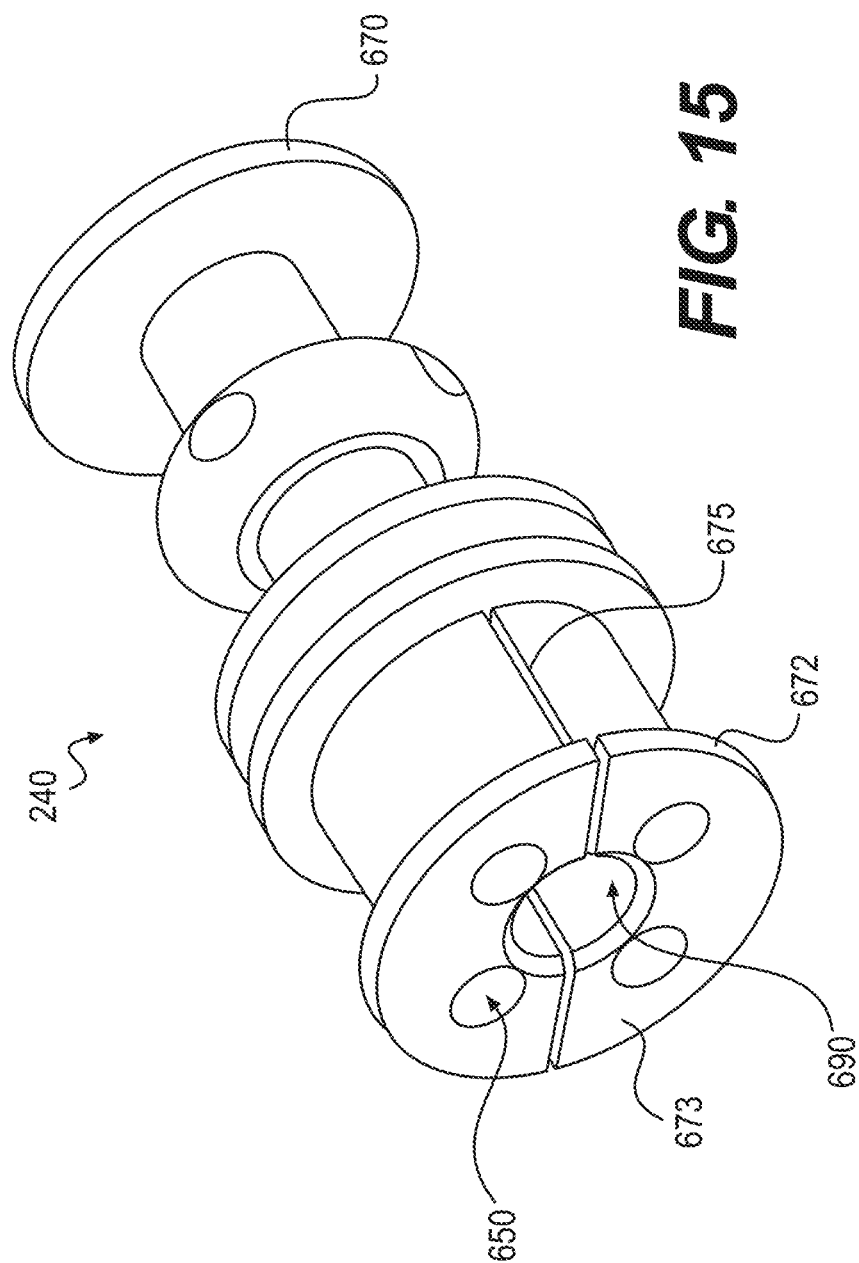

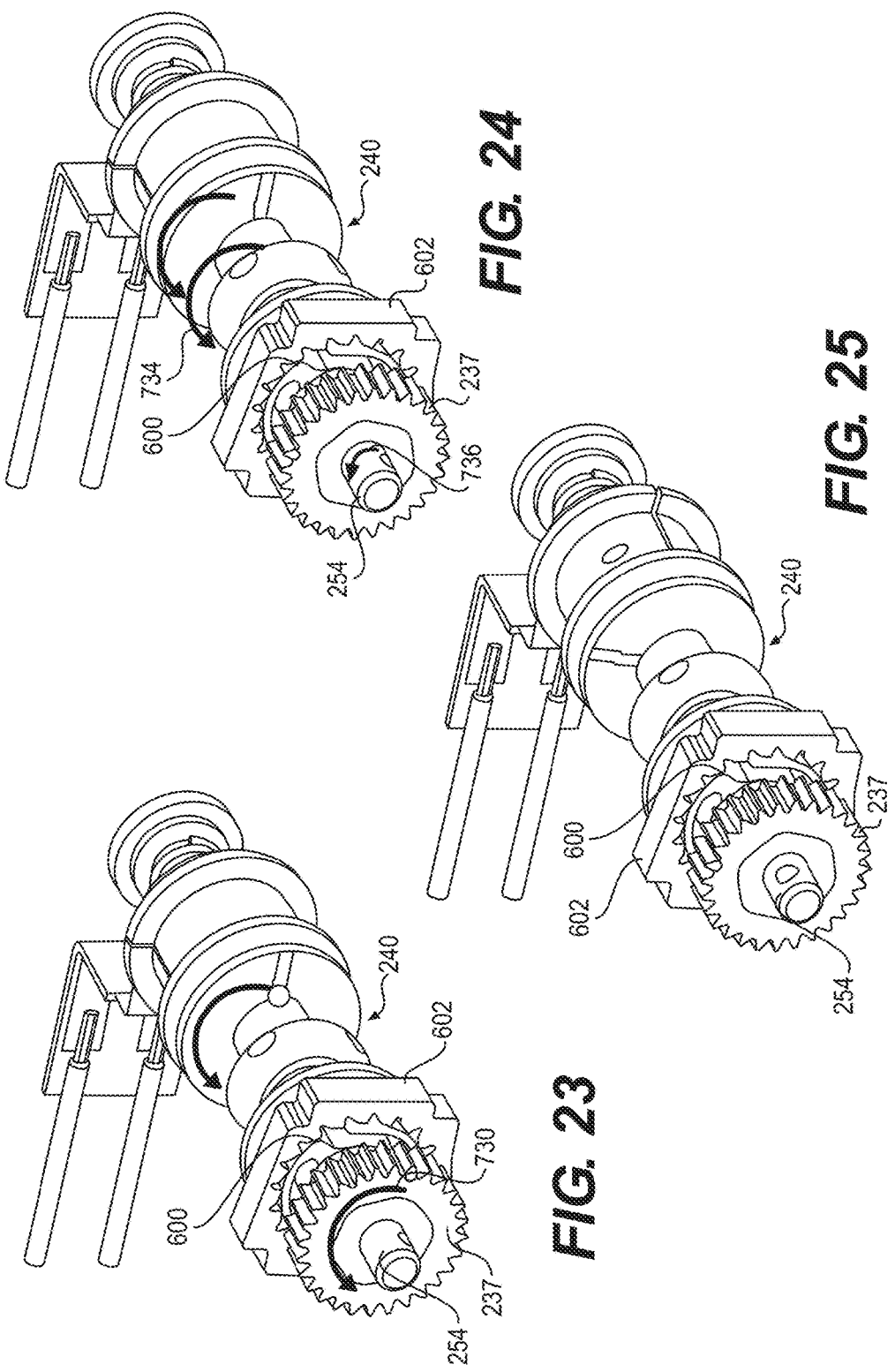

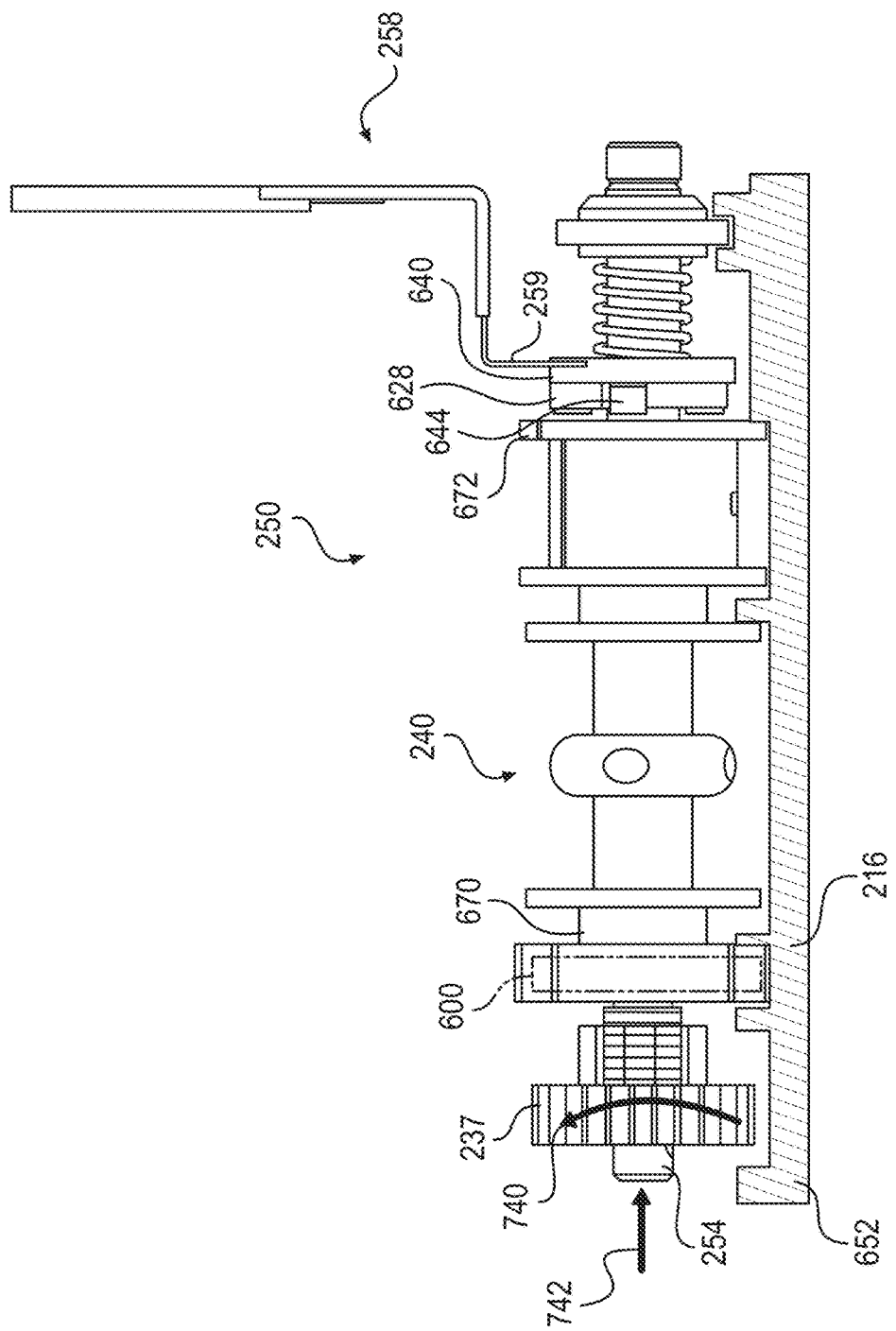

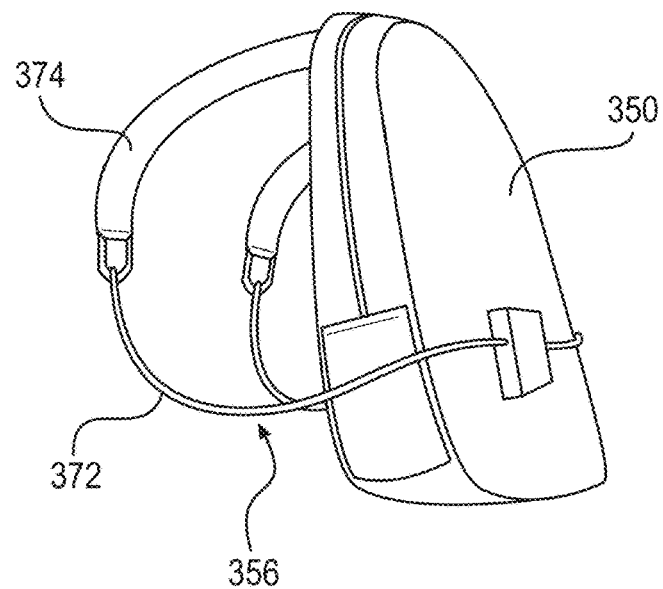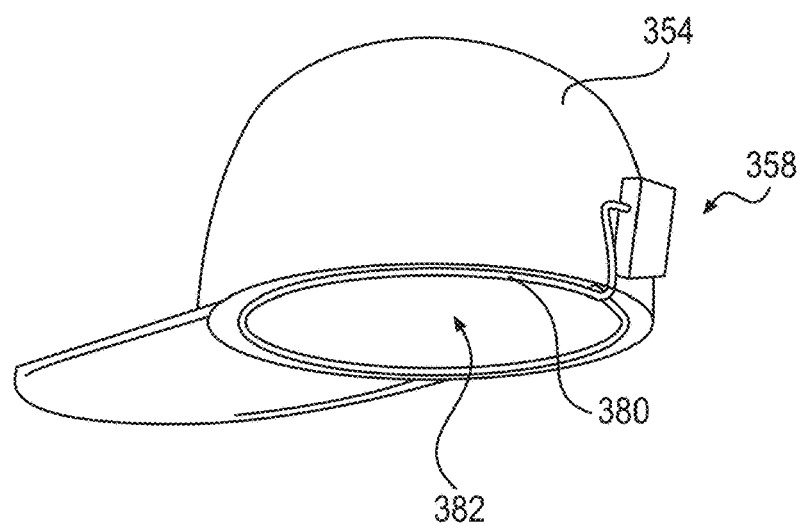
FIG. 37

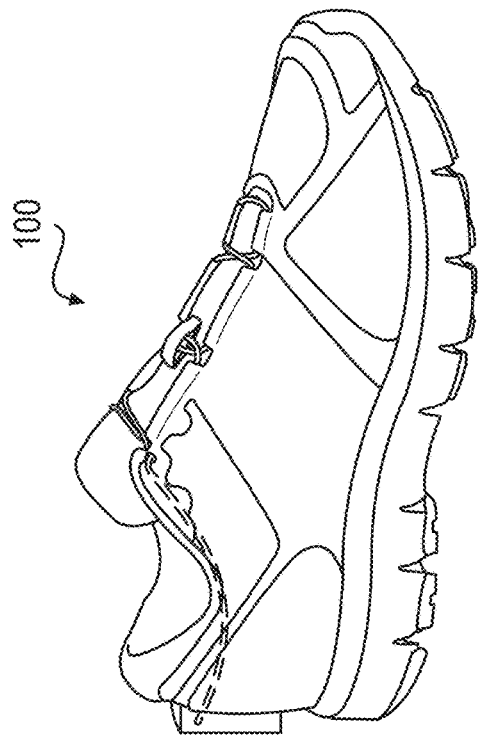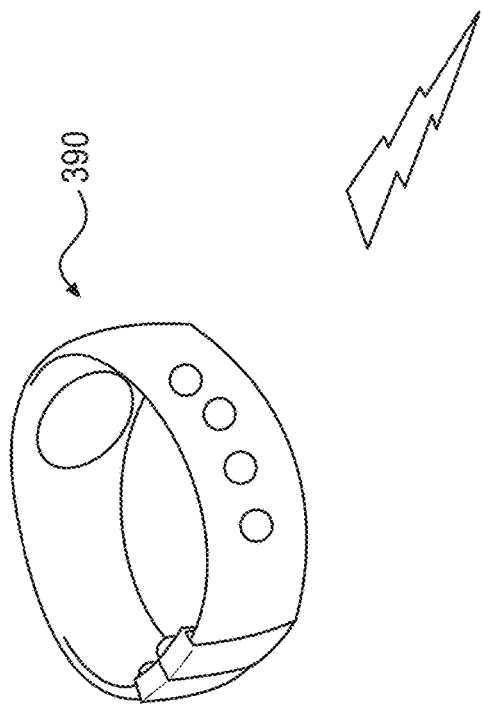
FIG. 38

MOTORIZED TENSIONING SYSTEM WITH SENSORS

RELATED APPLICATION

This application is a division of U.S. application Ser. No. 14/014,555, entitled "Motorized Tensioning System with Sensors", filed on Aug. 30, 2013, which application claims the benefit of priority to U.S. Provisional Patent Application Ser. No. 61/695,953, filed on Aug. 31, 2012, both of which are incorporated by reference herein in its entirety.

BACKGROUND

The present embodiments relate generally to articles of footwear and apparel including tensioning systems.

Articles of footwear generally include two primary elements: an upper and a sole structure. The upper is often formed from a plurality of material elements (e.g., textiles, polymer sheet layers, foam layers, leather, synthetic leather) that are stitched or adhesively bonded together to form a void on the interior of the footwear for comfortably and securely receiving a foot. More particularly, the upper forms a structure that extends over instep and toe areas of the foot, along medial and lateral sides of the foot, and around a heel area of the foot. The upper may also incorporate a lacing system to adjust the fit of the footwear, as well as permitting entry and removal of the foot from the void within the upper. Likewise, some articles of apparel may include various kinds of closure systems for adjusting the fit of the apparel.

SUMMARY

In one aspect, a method of operating a motorized tensioning device in an article of footwear includes sensing information related to a user set tension of a tensioning member used to fasten the article of footwear. The method also includes sensing a current tension of the tensioning member and determining if the current tension is less than the user set tension. The method also includes automatically controlling the motorized tensioning device to increase the tension of the tensioning member to achieve the user set tension when the current tension is less than the user set tension.

In another aspect, an article of footwear includes a tensioning member, a motorized tensioning device for controlling the tension of the tensioning member, at least one sensor for receiving information related to the tension of the tensioning member and a control unit, where the control unit can receive information from the at least one sensor. The control unit operates the motorized tensioning device in a normal operating mode and an active operating mode. The control unit powers down the motorized tensioning device after a target tension has been achieved in the normal operating mode. The control unit monitors the tension of the tensioning member and adjusts the motorized tensioning device to maintain the target tension in the active operating mode.

In another aspect, a footwear tension control system includes an article of footwear including a tensioning member, a motorized tensioning device for adjusting tension in the tensioning member, and a user control system in communication with the motorized tensioning device, where the user control system includes inputs that provide commands to the motorized tensioning device. The user control system includes a footwear selection input, the footwear selection input allowing the user to select between sending commands to a left article of footwear or a right article of footwear. The user control system includes a tighten input. The user control system includes a loosen input.

Other systems, methods, features and advantages of the embodiments will be, or will become, apparent to one of ordinary skill in the art upon examination of the following figures and detailed description. It is intended that all such additional systems, methods, features and advantages be included within this description and this summary, be within the scope of the embodiments, and be protected by the following claims.

BRIEF DESCRIPTION OF THE DRAWINGS

The embodiments can be better understood with reference to the following drawings and description. The components in the figures are not necessarily to scale, emphasis instead being placed upon illustrating the principles of the invention. Moreover, in the figures, like reference numerals designate corresponding parts throughout the different views.

FIG. 15 is a schematic isometric view of an embodiment of a spool;

FIG. 23 is a schematic isometric view of a torque transmitting system in a first stage of an incremental loosen configuration;

FIG. 24 is a schematic isometric view of a torque transmitting system in a second stage of an incremental loosen configuration;

FIG. 25 is a schematic isometric view of a torque transmitting system in a third stage of an incremental loosen configuration;

FIG. 26 is a schematic side view of an embodiment of a torque transmitting system transitioning to a full loosening configuration;

FIG. 37 is a schematic isometric view of an embodiment of additional articles of apparel that may be configured with tensioning systems including motorized tensioning devices:

FIG. 38 is a schematic isometric view of an embodiment of an article of footwear including a tensioning system and a remote bracelet configured to control a motorized tensioning device of the tensioning system;

DETAILED DESCRIPTION

Overview

Figure 1:
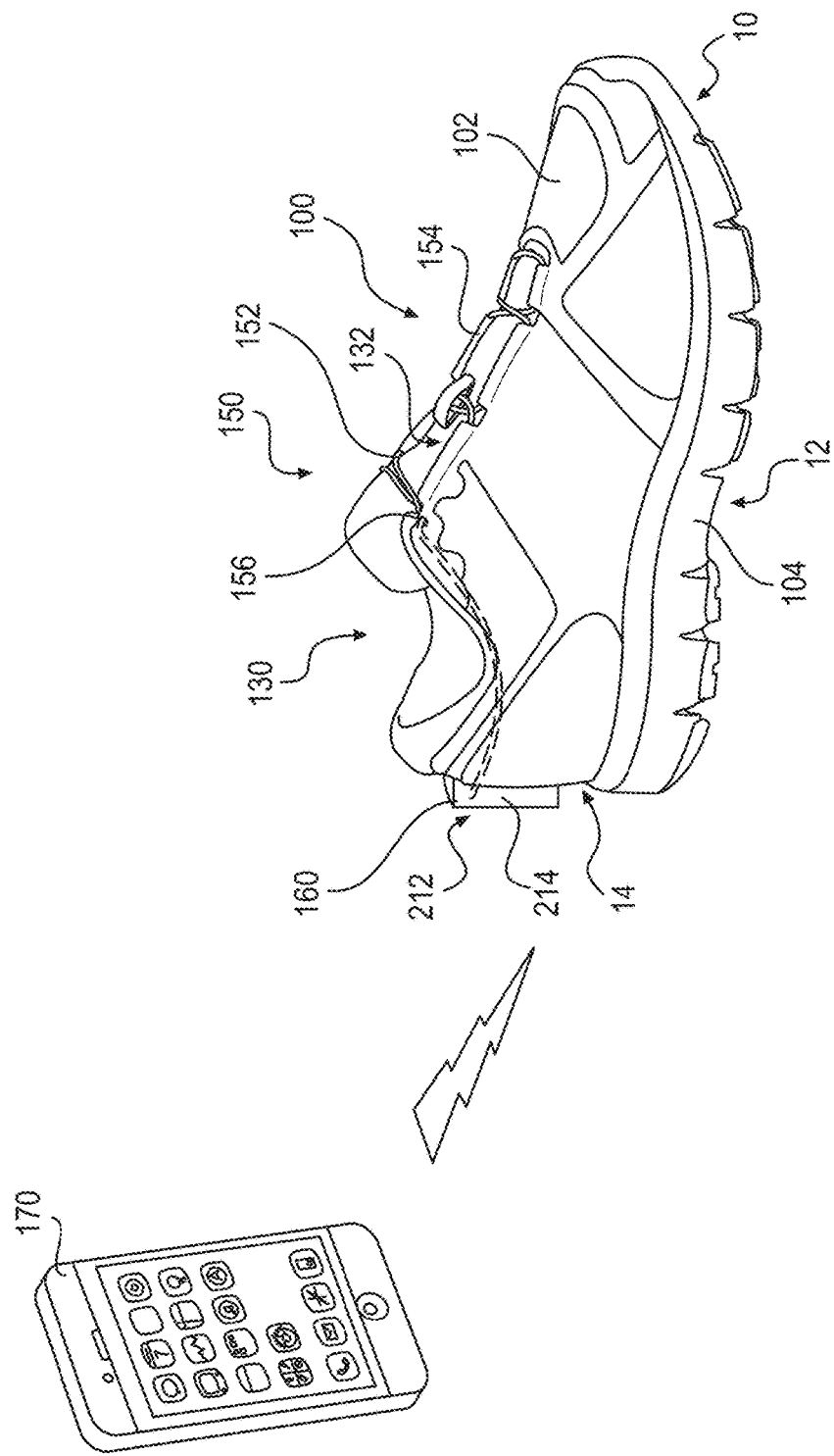
FIG. 1 is a schematic isometric view of an embodiment of an article of footwear with a tensioning system and a remote device for controlling the tensioning system.

FIG. 1 illustrates a schematic isometric view of an embodiment of article of footwear 100 that is configured with a tensioning system 150. In the current embodiment, article of footwear 100, also referred to hereafter simply as article 100, is shown in the form of an athletic shoe, such as a running shoe. However, in other embodiments, tensioning system 150 may be used with any other kind of footwear including, but not limited to: hiking boots, soccer shoes, football shoes, sneakers, running shoes, cross-training shoes, rugby shoes, basketball shoes, baseball shoes as well as other kinds of shoes. Moreover, in some embodiments article 100 may be configured for use with various kinds of non-sports related footwear, including, but not limited to: slippers, sandals, high heeled footwear, loafers as well as any other kinds of footwear. As discussed in further detail below, a tensioning system may not be limited to footwear and in other embodiments a tensioning system could be used with various kinds of apparel, including clothing, sportswear, sporting equipment and other kinds of apparel. In still other embodiments, a tensioning system may be used with braces, such as medical braces.

Referring to FIG. 1, for purposes of reference, article 100 may be divided into forefoot portion 10, midfoot portion 12 and heel portion 14. Forefoot portion 10 may be generally associated with the toes and joints connecting the metatarsals with the phalanges. Midfoot portion 12 may be generally associated with the arch of a foot. Likewise, heel portion 14 may be generally associated with the heel of a foot, including the calcaneus bone. It will be understood that forefoot portion 10, midfoot portion 12 and heel portion 14 are only intended for purposes of description and are not intended to demarcate precise regions of article 100.

For consistency and convenience, directional adjectives are employed throughout this detailed description corresponding to the illustrated embodiments. The term "longitudinal" as used throughout this detailed description and in the claims refers to a direction extending a length of a component. Also, the term "lateral" as used throughout this detailed description and in the claims refers to a direction extending a width of a component. Furthermore, the term "vertical" as used throughout this detailed description and in the claims refers to a direction that is perpendicular to both the longitudinal and lateral directions. It will be understood that each of these directional adjectives may be applied to various components shown in the embodiments, including article 100, as well as components of tensioning system 120.

Article 100 may include upper 102 and sole structure 104. Generally, upper 102 may be any type of upper. In particular, upper 102 may have any design, shape, size and/or color. For example, in embodiments where article 100 is a basketball shoe, upper 102 could be a high top upper that is shaped to provide high support on an ankle. In embodiments where article 100 is a running shoe, upper 102 could be a low top upper.

In some embodiments, sole structure 104 may be configured to provide traction for article 100. In addition to providing traction, sole structure 104 may attenuate ground reaction forces when compressed between the foot and the ground during walking, running or other ambulatory activities. The configuration of sole structure 104 may vary significantly in different embodiments to include a variety of conventional or non-conventional structures. In some cases, the configuration of sole structure 104 can be configured according to one or more types of ground surfaces on which sole structure 104 may be used. Examples of ground surfaces include, but are not limited to: natural turf, synthetic turf, dirt, as well as other surfaces.

In different embodiments, sole structure 104 may include different components. For example, sole structure 104 may include an outsole, a midsole, and/or an insole. In addition, in some cases, sole structure 104 can include one or more cleat members or traction elements that are configured to increase traction with a ground surface.

In some embodiments, sole structure 104 may be joined with upper 102. In some cases, upper 102 is configured to wrap around a foot and secure sole structure 104 to the foot. In some cases, upper 102 may include opening 130 that provides access to an interior cavity of article 100.

A tensioning system may include a tensioning member. The term "tensioning member" as used throughout this detailed description and in the claims refers to any component that has a generally elongated shape and high tensile strength. In some cases, a tensioning member could also have a generally low elasticity. Examples of different tensioning members include, but are not limited to: laces, cables, straps and cords. In some cases, tensioning members may be used to fasten and/or tighten an article, including articles of clothing and/or footwear. In other cases, tensioning members may be used to apply tension at a predetermined location for purposes of actuating some components or system.

Tensioning system 150 may comprise various components and systems for adjusting the size of opening 130 and thereby tightening (or loosening) upper 102 around a wearer's foot. In some embodiments, tensioning system 150 may comprise lace 152 as well as motorized tensioning device 160. Lace 152 may be configured to pass through various different lacing guides 154, which may be further associated with the edges of throat opening 132. In some cases, lacing guides 154 may provide a similar function to traditional eyelets on uppers. In particular, as lace 152 is pulled or tensioned, throat opening 132 may generally constrict so that upper 102 is tightened around a foot.

The arrangement of lacing guides 154 in this embodiment is only intended to be exemplary and it will be understood that other embodiments are not limited to a particular configuration for lacing guides 154. Furthermore, the particular types of lacing guides 154 illustrated in the embodiments are also exemplary and other embodiments may incorporate any other kinds of lacing guides or similar lacing provisions. In some other embodiments, for example, lace 154 could be inserted through traditional eyelets. Some examples of lace guiding provisions that may be incorporated into the embodiments are disclosed in Cotterman et al., U.S. Patent Application Publication Number 2012/0000091, now U.S. application Ser. No. 13/174,527, filed Jun. 30, 2011, and entitled "Lace Guide", which is hereby incorporated by reference in its entirety. Additional examples are disclosed in Goodman et al., U.S. Patent Application Publication Number 2011/0266384, now U.S. application Ser. No. 13/098,276, filed Apr. 29, 2011 and entitled "Reel Based Lacing System" (the "Reel Based Lacing Application"), which is hereby incorporated by reference in its entirety. Still additional examples of lace guides are disclosed in Kerns et al., U.S. Patent Application Publication Number 2011/0225843, now U.S. application Ser. No. 13/011,707, filed Jan. 21, 2011 and entitled "Guides For Lacing Systems", which is hereby incorporated by reference in its entirety.

Lace 152 may comprise any type of type of lacing material known in the art. Examples of lace that may be used include cables or fibers having a low modulus of elasticity as well as a high tensile strength. A lace may comprise a single strand of material, or can comprise multiple strands of material. An exemplary material for the lace is SPECTRA™, manufactured by Honeywell of Morris Township N.J., although other kinds of extended chain, high modulus polyethylene fiber materials can also be used as a lace. Still further exemplary properties of a lace can be found in the Reel Based Lacing Application mentioned above.

In some embodiments, lace 152 may be passed through lacing guides 154 and may pass through internal channels (not shown) within upper 102 after entering channel openings 156 that are above lacing guides 156. In some embodiments, the internal channels extend around the sides of upper 102 and guide the lace towards motorized tensioning device 160, which may be mounted on heel portion 14 of upper 102. In some cases, motorized tensioning device 160 may include provisions for receiving portions of lace 152. In some cases, end portions of lace 152 exit internal channels of upper 102 and pass through apertures in a housing unit 212 of motorized tensioning device 160.

Motorized tensioning device 160 may be configured to automatically apply tension to lace 152 for purposes of tightening and loosening upper 102. As described in further detail below, motorized tensioning device 160 may include provisions for winding lace 152 onto, and unwinding lace 152 from, a spool internal to motorized tensioning device 160. Moreover, the provisions may include an electric motor that automatically winds and unwinds the spool in response to various inputs or controls.

Provisions for mounting motorized tensioning device 160 to upper 102 can vary in different embodiments. In some cases, motorized tensioning device 160 may be removably attached, so that motorized tensioning system 160 can be easily removed by a user and modified (for example, when a lace must be changed). Examples of provisions for removably attaching motorized tensioning system 160 to upper 102 are discussed in detail later. In other cases, motorized lacing device 160 could be permanently attached to upper 102. In one embodiment, for example, an external harness (not shown) may be used to mount motorized tensioning system 160 to upper 102 at heel portion 14.

In some embodiments, motorized tensioning device 160 may communicate with remote device 170. In some cases, motorized tensioning device 160 may receive operating instructions from remote device 170. For example, motorized tensioning device 160 may receive instructions to apply increased tension to lace 152 by winding the spool. In some cases, remote device 170 may be capable of receiving information from motorized tensioning device 160. For example, remote device 170 could receive information related to the current tension in lace 152 and/or other sensed information. As discussed below in reference to FIG. 2, remote device 170 may function as a remote control that may be used by the wearer to operate tensioning system 150.

In one embodiment, remote device 170 comprises a mobile phone, such as the iPhone made by Apple, Inc. In other embodiments, any other kinds of mobile phones could also be used including smartphones. In other embodiments, any portable electronic devices could be used including, but not limited to: personal digital assistants, digital music players, tablet computers, laptop computers, ultrabook computers as well as any other kinds of portable electronic devices. In still other embodiments, any other kinds of remote devices could be used including remote devices specifically designed for controlling motorized tensioning device 160. In another embodiment, discussed in detail below, remote device 170 could comprise a bracelet, wristband and/or armband that is worn by a user and specifically designed for communicating with motorized tensioning device 160. The type of remote device could be selected according to software and hardware requirements, ease of mobility, manufacturing expenses, as well as possibly other factors. In some embodiments, motorized tightening device 160 may communicate with multiple remote devices. For example, a user may use a mobile device, such as an iPhone, at home to identify and set preferred tension settings, and another remote device with more rudimentary controls might then be used to issue commands to motorized tightening device 160, such as with a bracelet, wristband and/or armband while playing sports. For example, a bracelet might allow a user to recall a set tension and adjust it, but not set a new tension for later recall. In some embodiments, such as where motorized tightening device 160 is used for a medical brace, a physician may be provided with fewer controls for the medical brace. For example, the wearer may be provided with a remote device that allows a full range of commands and/or tensions for adjusting fit or performance, but the wearer of that brace may be provided with a remote device that is not configured to issue all of the commands available with the physician's remote device and/or allows a more limited range of tension adjustment, such as for improving comfort without disturbing the overall fit of the brace.

As already mentioned, remote device 170 may communicate with motorized tightening device 160 (or indirectly with motorized tightening device 160 via a secondary device, such as a separate control unit). Examples of different communication methods include, but are not limited to: wireless networks such as personal area networks (e.g., Blutetooth) and local area networks (e.g., Wi-Fi) as well as any kinds of RF based methods known in the art. In some embodiments, infrared light may be used for wireless communication. Although the illustrated embodiments detail a remote device 170 that communicates wirelessly with motorized tensioning system 160, in other embodiments remote device 170 and motorized tensioning system 160 may be physically connected and communicate through one or more wires.

For purposes of clarity, a single article of footwear is shown in the embodiments. However, it will be understood that remote device 170 may be configured to operate a corresponding article of footwear which also includes a similar tensioning system (e.g., a pair of footwear each having a tensioning system). As described below, remote device 170 may be used to operate each the tensioning systems of each article independently of one another.

Figure 2:
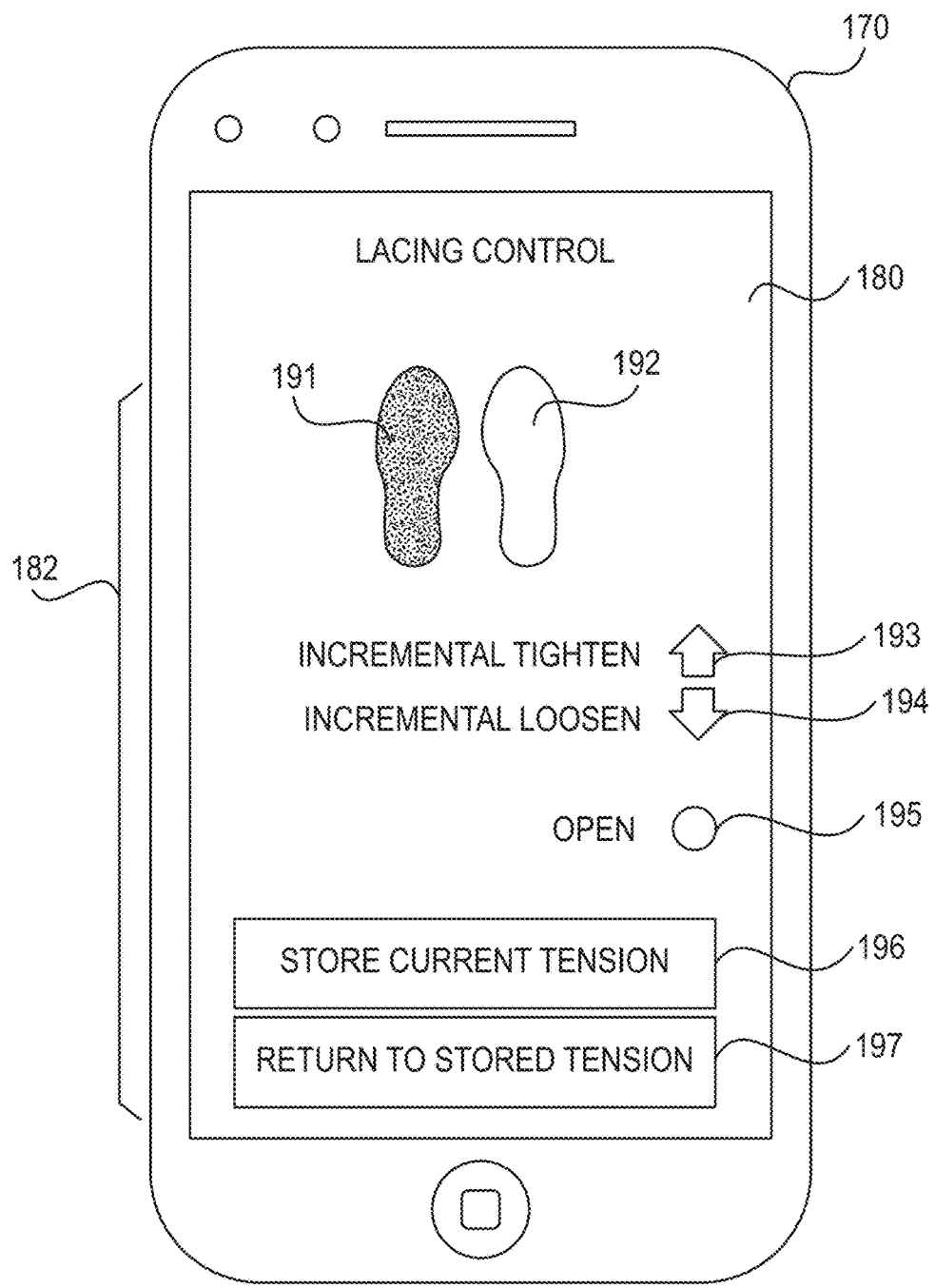
FIG. 2 is a schematic view of an embodiment of a remote device running a lacing control application.

FIG. 2 illustrates a schematic view of an embodiment of remote device 170, including a schematic of an example user interface for controlling tensioning system 150. In some embodiments, remote device 170 may be capable of running a lacing control software application 180, hereafter referred to simply as application 180. In embodiments where remote device 170 is a mobile phone (or similar digital device) capable of running mobile software applications, application 180 may be downloaded by a user from a third party online store or website. Such a mobile phone (or similar digital device) may include a touch screen LCD device which may be used by application 180 for input and output interaction with a user. In some embodiments, a touch screen LCD or non-touch screen LCD may be used for output display only.

Application 180 may display and respond to user interaction with a plurality of control buttons 182, and initiate control commands in response to such interaction. Example control commands may include, but are not limited to, left/right shoe selection, incremental tighten, incremental loosen, open/fully loosen, store tension, and recall/restore tension. In the exemplary embodiment of FIG. 2, these control buttons include a first button 191 and a second button 192, which are respectively used to select the left or right shoe that will receive and respond to the control commands. In some embodiments, either first button 191 or second button 192 may be selected, but both may not be selected simultaneously. In other cases, it may be possible to select both first button 191 and second button 192 simultaneously, to allow a user to tighten, loosen, or open both shoes simultaneously. In addition, application 180 may include third button 193 for initiating an "incremental tighten" command, a fourth button 194 for initiating an "incremental loosen" command and a fifth button 195 for initiating an "open" (or fully loosen) command. Optionally, some embodiments could include a "fully tighten" command that would tighten the footwear until a predetermined threshold is achieved (for example, a threshold pressure, winding distance, etc.).

In some embodiments, a shoe, article, or other item may include more than one motorized tightening device 160. In such embodiments, each motorized tightening device 160 may include wireless communication hardware for separately communicating with a remote device 170, or a single wireless communication device may be provided for common use by multiple motorized tightening devices 160. For such embodiments, remote device 170 may be configured, such as with application 180, to provide additional buttons or other controls to individually adjust plural motorized tightening devices 160 on a single article. For example, button 191 illustrated in FIG. 2 could be subdivided into a top region and lower region which are separately responsive to user interaction. By use of these regions, one of two motorized tightening devices 160 could be selected for tension adjustment via buttons 193, 194, and 195. In another example, additional buttons like buttons 193 and 194 could be displayed at the same time by application 180, allowing for more rapid adjustment of multiple motorized tightening devices 160.

Application 180 may also include provisions for storing and using preferred tension settings. For example, sixth button 196 and seventh button 197 may be used to initiate a "store current tension" command and a "return to stored tension" command, respectively. In some cases, the tension values could be stored at the remote device, while in other cases the tension values could be stored in internal memory of a control board for the motorized tensioning device 160. Still other embodiments could include provisions for storing multiple tension settings. For example, a user may prefer a tighter fit for playing sports and a looser fit for casual activities. In such cases, remote device 170 may allow a user to store two or more tension settings, corresponding to at least two different lace tension preferences. In some embodiments, sixth button 196 may cause the tension setting for a single, currently selected, motorized tightening device 160 to be stored, and in some embodiments sixth button 196 may cause the tension settings for multiple motorized tightening devices 160 to be stored in a single action. Those skilled in the art appreciate that storage or recall of tensions for multiple motorized tightening devices 160, whether part of a single item of apparel or multiple items, such as a pair of shoes, may be performed with a single command issued by a remote device 170 or with a series of control commands, such as by issuing separate control commands to each motorized tightening device 160 and/or item of apparel.

In some embodiments, application 180 and/or remote device 170 may be configured to selectively control individual items or individual sets of items, such as a pair of shoes, from among multiple items or sets of items within communication range of remote device 170. For example, application 180 may be configured to enumerate items by unique identifiers assigned to each item, display the enumerated items to a user, and receive an input selecting an item. In another example, an application 180 may be paired via BlueTooth with a particular item or set of items. In another example, a remote device without an LCD display may include a control button that may be pressed, repeatedly if needed, to select a desired item, and the item may include an LED which is illuminated when it is in wireless communication with the remote device.

The embodiments are not limited to a particular user interface or application for remotely operating motorized tensioning device 160. The embodiments here are intended to be exemplary, and other embodiments could incorporate any additional control buttons, interface designs and software applications. As one example, some embodiments may not include provisions for selecting the shoe to be controlled, and instead could utilize two sets of control buttons, where each set corresponds to either the left or right shoe. The control buttons for initiating various operating commands can be selected according to various factors including: ease of use, aesthetic preferences of the designer, software design costs, operating properties of the motorized tensioning device 160 as well as possibly other factors.

Throughout the detailed description and in the claims, various operating modes, or configurations, of a tensioning system are described. These operating modes may refer to states of the tensioning system itself, as well as to the operating modes of individual subsystems and/or components of the tensioning system. Exemplary modes include an "incremental tighten mode", an "incremental loosen mode" and a "fully loosen" mode. The latter two modes may also be referred to as an "incremental release mode" and a "full release mode". In the incremental tighten mode, motorized tightening device 160 may operate in a manner that incrementally (or gradually) tightens, or increases the tension of, lace 152. In the incremental loosen mode, motorized tightening device 160 may operate in a manner that incrementally (or gradually) loosens, or releases tension in, lace 152. As discussed further below, the incremental tighten mode and the incremental loosen mode may tighten and loosen a lace in discrete steps or continuously. In the full release mode, motorized tightening device 160 may operate in a manner so that tension applied to the lace by the system is substantially reduced to a level where the user can easily remove his or her foot from the article. This is in contrast to the incremental release mode, where the system operates to achieve a lower tension for the lace relative to the current tension, but not necessarily to completely remove tension from the laces. Moreover, while the full release mode may be utilized to quickly release lace tension so the user can remove the article, the incremental release mode may be utilized to make minor adjustments to the lace tension as a user searches for the desired amount of tension. Although the embodiments describe three possible modes of operation (and associated control commands), other operating modes may also be possible. For example, some embodiments could incorporated a fully tighten operating mode where motorized tightening device 160 continues to tighten lace 152 until a predetermined tension has been achieved.

FIGS. 3 through 7 illustrate schematic views of an embodiment of article 100 being tightened and loosened during different operating modes of tensioning system 150. Each figure also shows a schematic view of remote device 170, including the particular control button used to initiate each operating mode.

Figure 3:
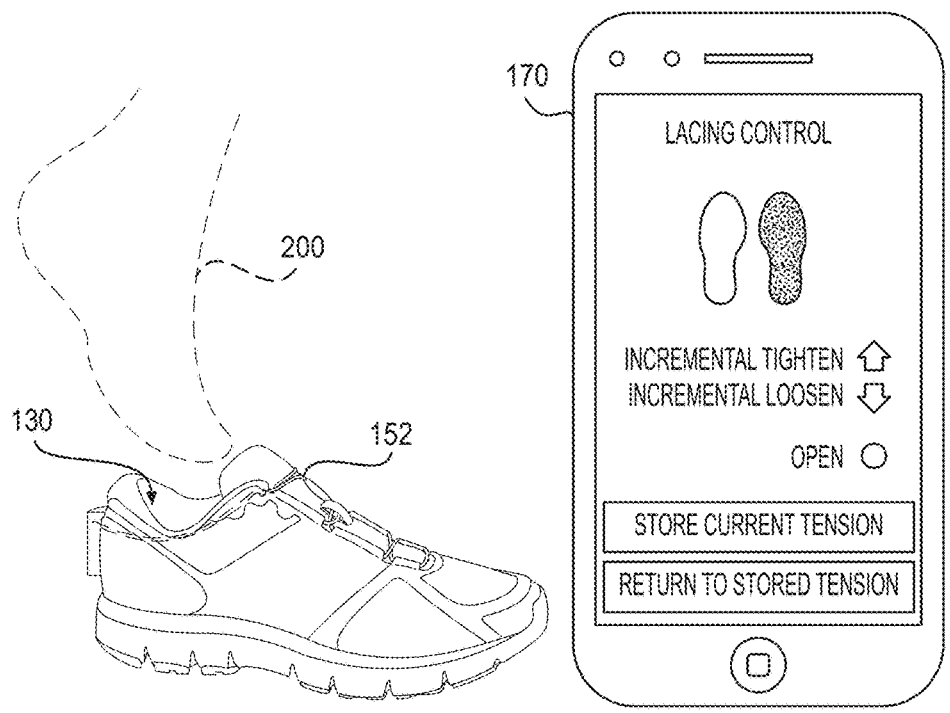
FIG. 3 is a schematic view of an embodiment of a foot being inserted into an article and a remote device running a lacing control application.
Figure 4:
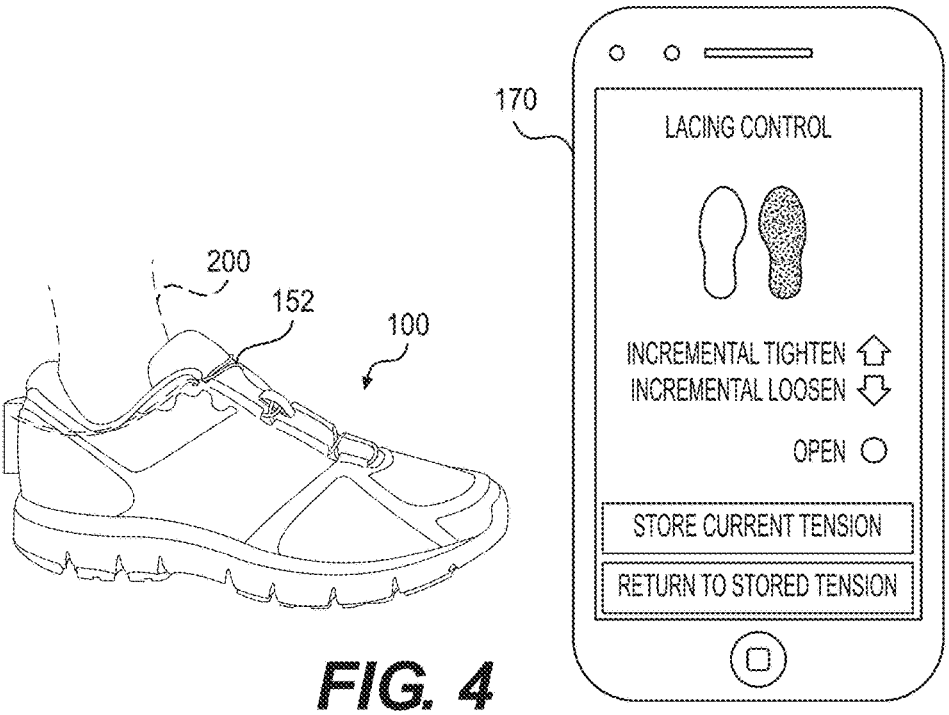
FIG. 4 is a schematic view of an embodiment of a foot fully inserted into an article and a remote device running a lacing control application.
Figure 5:
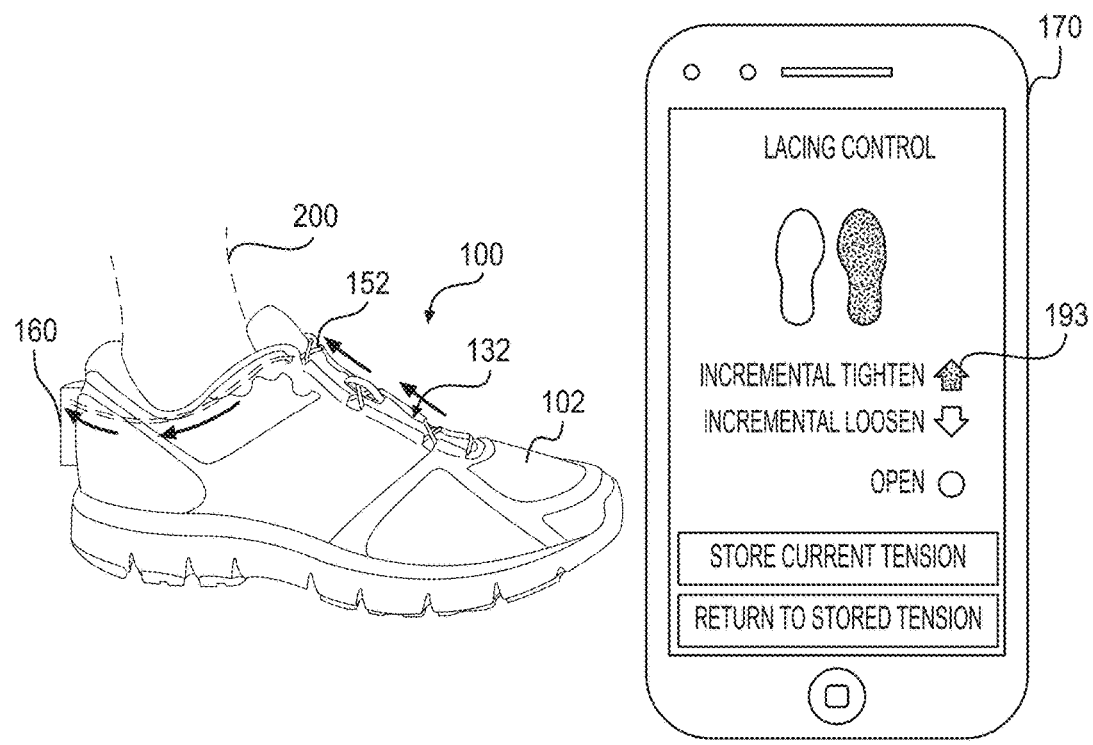
FIG. 5 is a schematic view of an embodiment of an article being tightened as a remote device sends an incremental tighten command to a tensioning system.

FIG. 3 shows article 100 is in a fully opened state just prior to the entry of foot 200. In this state, lace 152 may be loose enough to allow a user to insert his or her foot into opening 130. Referring next to FIG. 4, foot 200 is inserted into article 100, which remains in the fully opened state. Referring next to FIG. 5, an incremental tighten command has been sent to motorized tensioning device 160 by pressing third button 193 of remote device 170. This command causes motorized tensioning device 160 to enter an incremental tighten mode. At this point, the tension of lace 152 is increased to tighten upper 102 around foot 200. In particular, lace 152 is drawn into motorized tensioning device 160, which pulls on the portions of lace 152 disposed adjacent throat opening 132 and thus constricts throat opening 132. In some cases, this incremental tightening can occur in discrete steps so that each time the wearer presses third button 193, lace 152 is taken up by a predetermined amount (for example by rotating a spool within motorized tensioning device 160 through a predetermined angle). In other cases, this incremental tightening can occur in a continuous manner, as long as the wearer continues to touch third button 193. In some cases, the speed of tightening can be set so that the system does not overshoot a preferred level of tightness (i.e., the system doesn't move between not tight enough and overly tight too quickly) while also being large enough to avoid overly long times for fully tightening article 100.

Figure 6:
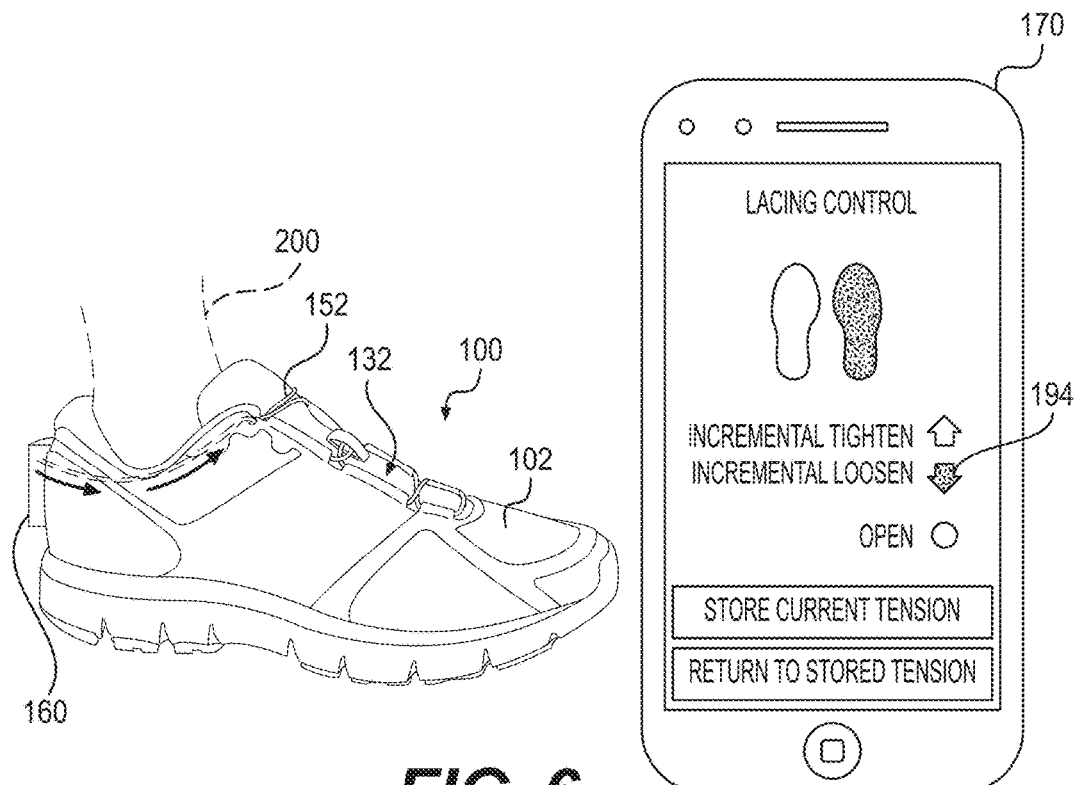
FIG. 6 is a schematic view of an embodiment of an article being loosened as a remote device sends an incremental loosen command to a tensioning system.
Figure 7:
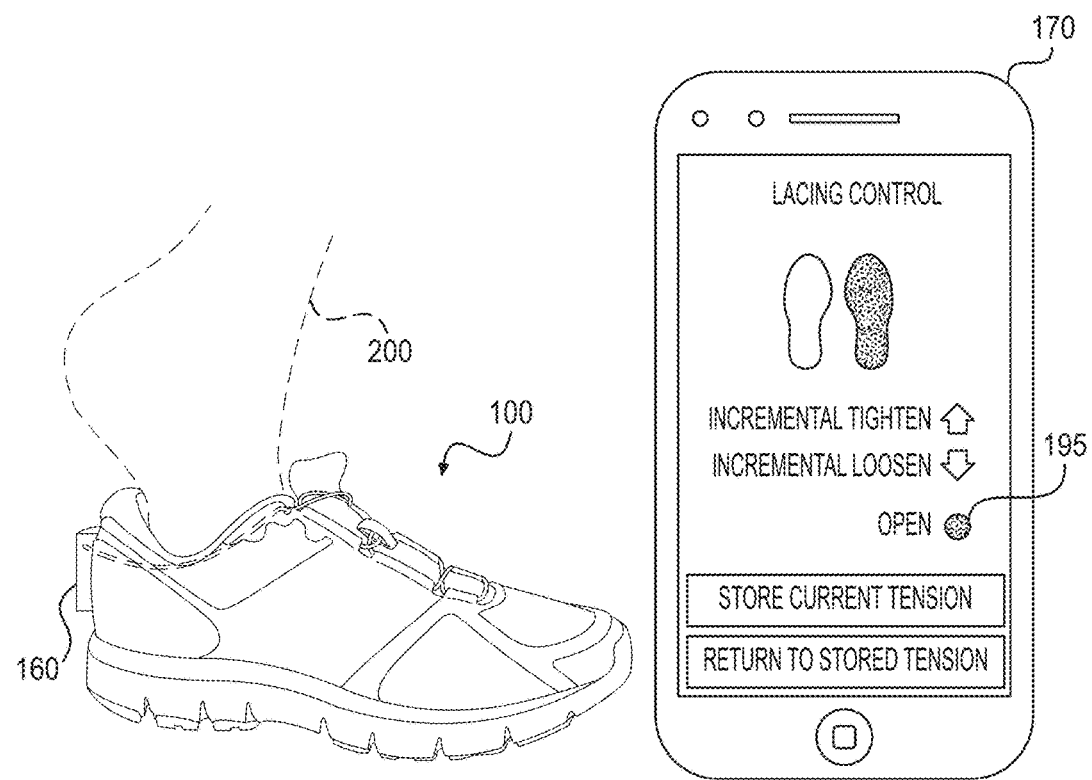
FIG. 7 is a schematic view of an embodiment of an article opened to allow a foot to be removed after a remote device has sent an open command to a tensioning system.

FIGS. 6 and 7 illustrate schematic views of two different operating modes where lace 152 may be loosened. Referring first to FIG. 6, a wearer can press fourth button 194 to initiate an incremental loosen command in tensioning system 150. Upon receiving the incremental loosen command, motorized tensioning device 160 may operate in an incremental loosen mode, in which lace 152 is released from motorized tensioning device 160 (i.e., sections of lace 152 exit from motorized tensioning device 160). This relaxes some of the tension in lace 152 and allows throat opening 132 to partially expand. In some cases, this incremental loosening can occur in discrete steps so that each time the wearer presses fourth button 194, lace 152 is let out up by a predetermined amount (for example by rotating a spool within motorized tensioning device 160 through a predetermined angle). In other cases, this incremental loosening can occur in a continuous manner, as long as the wearer continues to touch fourth button 194. In some cases, the speed of loosening can be set so that the system does not overshoot a preferred level of tightness (i.e., the system doesn't move between too tight and not tight enough too quickly) while also being large enough to avoid overly long times for fully loosening article 100. With this arrangement, a wearer can continue increasing and decreasing the tension of lace 152 (using the incremental tighten and incremental loosen modes) until a preferred level of tightness for upper 102 is achieved.

Referring next to FIG. 7, a wearer can press fifth button 195 to initiate an open, or fully loosen, command in tensioning system 150. In contrast to the incremental loosen command, the open command may be used to quickly relieve all (or most of) tension in lace 152 so that a user can quickly remove article 100. Thus, upon receiving the open command, motorized tensioning device 160 operates in a fully loosen mode. In this mode, motorized tensioning device operates to let out enough of lace 152 so that substantially all tension is removed from lace 152. In some cases, this may be achieved by continuously monitoring tension in lace 152 (for example, using sensors) and letting out lace 152 until the level of tension is below a threshold tension. In other cases, this may be achieved by letting out a predetermined length of lace 152 known to correspond approximately to the amount needed to achieve a fully loosened state for tensioning system 150. As seen in FIG. 7, with tensioning system 150 in the open state, foot 200 can be easily and comfortably removed from footwear 100.

Figure 8:
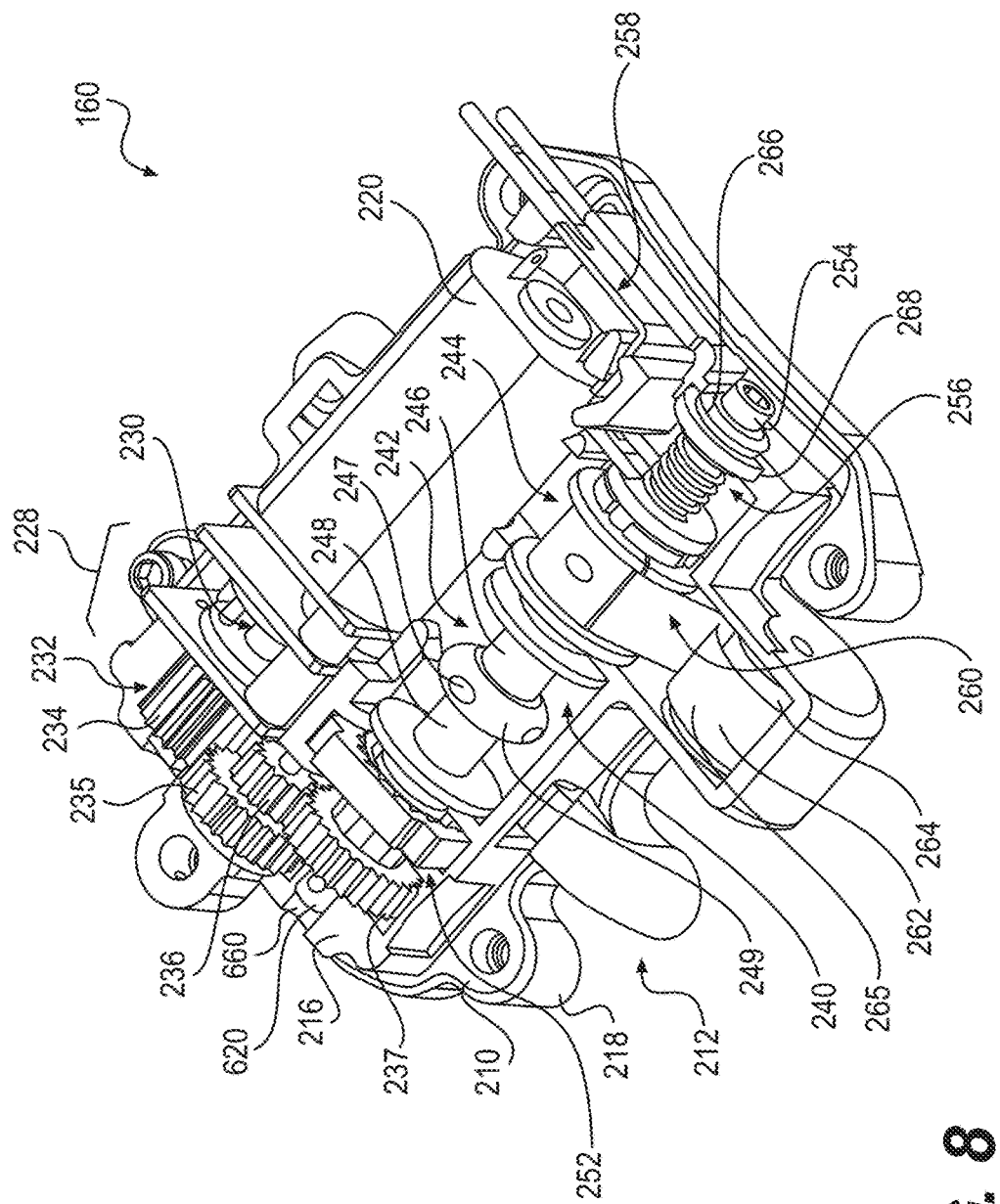
FIG. 8 is a schematic isometric view of an embodiment of a motorized tensioning device with an outer cover of the housing unit removed.
Figure 9:
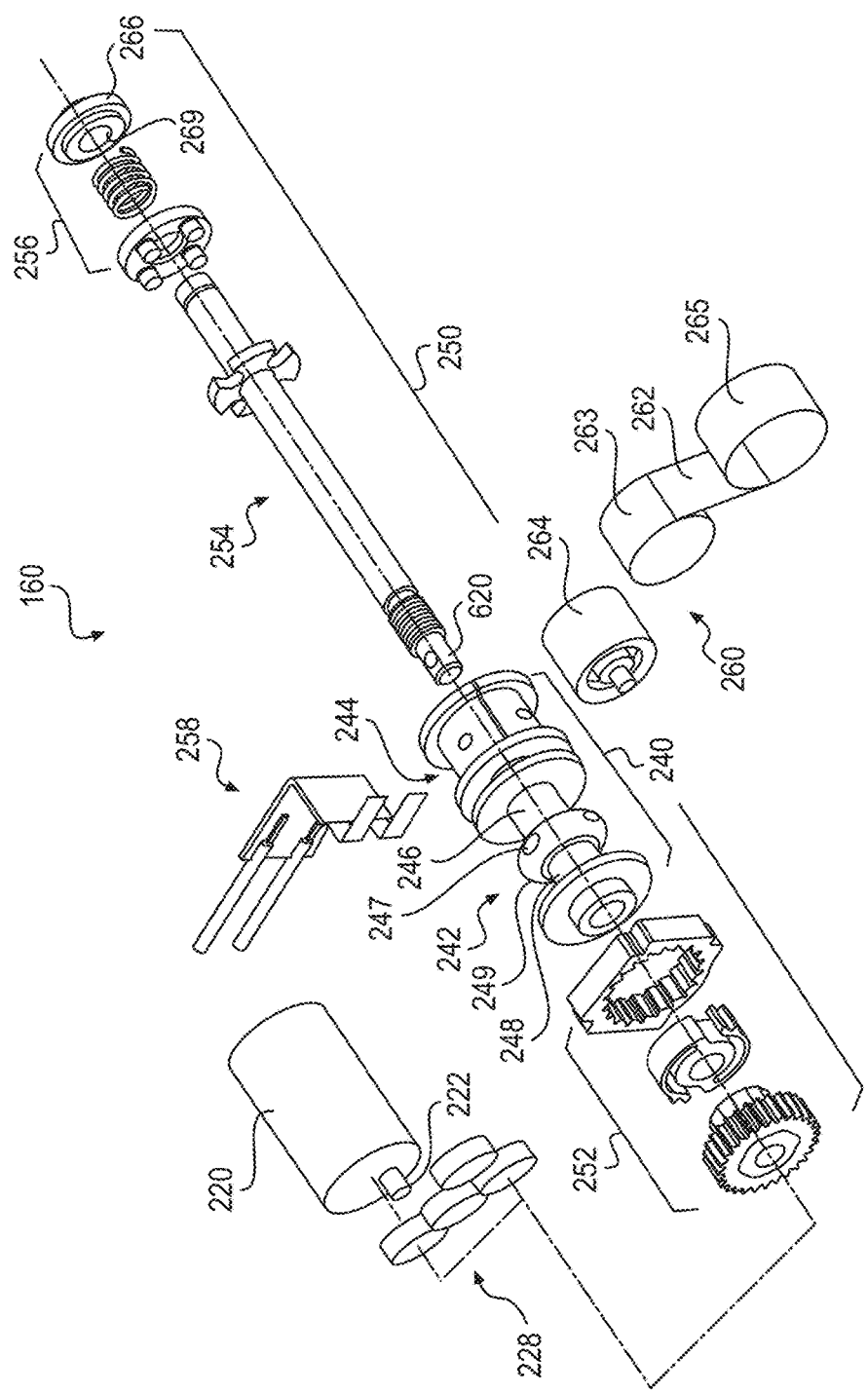
FIG. 9 is a schematic exploded isometric view of an embodiment of some components of a motorized tensioning device.

FIGS. 8 and 9 illustrate an isometric view and isometric exploded view, respectively, of an embodiment of the internal components of motorized tensioning device 160. Referring first to FIG. 8, the components are shown within a portion of housing unit 212. Housing unit 212 may further include an inner housing portion 216 and an outer housing portion 218. Outer housing portion 218 may include a base panel 210 as well as an outer cover 214 (shown in FIG. 1), and generally provides a protective outer covering for components of motorized tensioning device 160. Inner housing portion 216 may be shaped to support components of motorized tensioning device 160. In some cases portions of inner housing portion 216 function to limit the mobility of some components, as discussed in detail below.

Referring now to FIGS. 8 and 9, in some embodiments, motorized tensioning system 160 may comprise motor 220 (shown schematically in FIG. 9). In some embodiments, motor 220 may be an electric motor. However, in other embodiments, motor 220 could comprise any kind of non-electric motor known in the art. Examples of different motors that can be used include, but are not limited to: DC motors (such as permanent-magnet motors, brushed DC motors, brushless DC motors, switched reluctance motors, etc.), AC motors (such as motors with sliding rotors, synchronous electrical motors, asynchronous electrical motors, induction motors, etc.), universal motors, stepper motors, piezoelectric motors, as well as any other kinds of motors known in the art. Motor 220 may further include a motor crankshaft 222 that can be used to drive one or more components of motorized tensioning system 160. Provisions for powering motor 220, including various kinds of batteries, are discussed in detail below.

In some embodiments, motorized tensioning system 160 can include provisions for reducing the output speed of, and increasing the torque generated by, motor 220. In some embodiments, motorized tensioning system 160 can include one or more gear reduction assemblies and/or gear reduction systems. In some embodiments, motorized tensioning system 160 may include a single gear reduction assembly. In other embodiments, motorized tensioning system 160 may include two or more gear reduction assemblies. In one embodiment, motorized tensioning system 160 includes first gear reduction assembly 230 and second gear reduction assembly 232, which may be collectively referred to as gear reduction system 228. First gear reduction assembly 230 may be an in-line spur gear reduction assembly that is generally aligned with motor 220 and/or crankshaft 222. In contrast, second gear reduction assembly 232 may provide additional gear reduction that extends in a generally perpendicular direction to the orientation of crankshaft 222. With respect to housing unit 212, first gear reduction assembly 230 may extend in a longitudinal direction of housing unit 212 while second gear reduction assembly 232 may extend in a lateral (or horizontal) direction of housing unit 212. By using a combination of in-line gears and horizontally spaced gears, relative to the orientation of crankshaft 222, motor 220 can be arranged in parallel with a spool and corresponding spool shaft (as discussed in further detail below). This arrangement may reduce the longitudinal space required to fit all the components of motorized tensioning device 160 within housing unit 212.

Each gear reduction assembly can comprise one or more gears. In the exemplary embodiment, first gear reduction assembly 230 comprises one or more in-line spur gears. Moreover, first gear reduction assembly 230 may be driven by crankshaft 222 and itself drives a first gear 234 of second gear reduction assembly 232.

In one embodiment, second gear reduction assembly 232 may be configured with 4 stages of spur gears, including a first gear 234, a second gear 235, a third gear 236 and a fourth gear 237. In this embodiment, fourth gear 237 acts as a clamping gear for turning additional components of motorized tensioning device 160, as described in further detail below. The current embodiment of second gear reduction assembly 232 includes four gears. However, other embodiments could use any other number of gears. Likewise, the number of gears comprising first gear reduction assembly 230 may vary in different embodiments. Additionally, in different embodiments, the type of gears used in first gear reduction assembly 230 and/or second gear assembly 232 could vary. In some cases, spur gears may be used. Other examples of gears that may be used include, but are not limited to: helical gears, external gears, internal gears, bevel gears, crown gears, worm gears, non-circular gears, rack and pinion gears, epicyclic gears, planetary gears, harmonic drive gears, cage gears, magnetic gears as well as any other kinds of gears and/or any combinations of various kinds of gears. The number, type and arrangement of gears for gear reduction system 228 may be selected to achieve the desired tradeoff between size, torque and speed of the motorized tensioning system 160.

In some embodiments, motorized tensioning system 160 can include provisions for winding and unwinding portions of a lace. In some embodiments, motorized tensioning system 160 can include spool 240. In some cases, spool 240 may further comprise a first receiving portion 242 and a second receiving portion 244 for receiving a lace and a portion of a spring, respectively. Moreover, in some cases, first receiving portion 242 may comprise a first lace winding region 246 and a second lace winding region 248, which in some cases can be used to separately wind two ends of a lace. Since torque output goes down as the lace builds up in diameter, using separate winding regions for each lace end may help decrease the diameter of wound lace on spool 240 and thereby minimize torque output reduction. In some cases, first lace winding region 246 and second lace winding region 248 may be separated by a dividing portion 249, which may include a lace receiving channel 247 for permanently retaining a portion of the lace on spool 240. In other cases, however, first receiving portion 242 may comprise a single lace winding region.

Motorized lacing system 160 may include provisions for transferring torque between a final drive gear of second gear reduction assembly 232 and spool 240. In some embodiments, motorized lacing system 160 may include provisions for transferring torque from second gear reduction assembly 232 (or more generally from gear reduction system 228) to spool 240 in a manner that allows for incremental tightening, incremental loosening and full loosening of a lace. In one embodiment, motorized lacing system 160 may be configured with a torque transmitting system 250 that facilitates the transmission of torque from fourth gear 237 of second gear reduction assembly 232 to spool 240.

Torque transmitting system 250 may further comprise various assemblies and components. In some embodiments, torque transmitting system 250 may include a ratcheting assembly 252, a shaft 254 and a rotation control assembly 256. As discussed in further detail below, the components of torque transmitting system 250 operate to transmit torque from fourth gear 237 of second gear reduction assembly 232 to spool 240. More specifically, these components operate in a manner that allows for incremental tightening (spool winding), incremental loosening (spool unwinding) as well as full tension release (during which time substantially no torque is transferred from fourth gear 237 to spool 240).

In some embodiments, motorized tensioning device 160 may further include a secondary winding assembly 260. In some embodiments, secondary winding assembly 260 may be configured to apply torque to spool 240 independently of any torque applied by motor 220. In some cases, for example, secondary winding assembly 260 comprises a spring member 262 and a rotatable spring bearing 264. Spring member 262 may extends between second receiving portion 244 of spool 240 and spring bearing 264. In particular, a first end portion 263 of spring member 262 may be associated with spool 240 while a second end portion 265 of spring member 262 may be associated with spring bearing 264. In operation, spring member 262 may be configured to apply a biasing torque that may tend to rotate spool 240 in the lace winding direction in the absence of other forces or torques (for example when there is slack in the lace). Spring member 262 could be a wind-up spring, a constant force spring, a constant torque spring, a clock spring as well as any other kind of spring.

Some embodiments can also include a fixed bearing 266, which may be associated with an end of shaft 254. In some embodiments, fixed bearing 266 may be received within a recess 268 of inner housing portion 216. In some embodiments, an end of shaft 254 may be disposed within opening 269 of fixed bearing 266, and may be configured so that shaft 254 can slide through opening 269 to provide some axial movement for shaft 254.

In some embodiments, motorized tensioning device 160 may include provisions for adjusting the operation of motor 220 according to one or more feedback signals. In some embodiments, for example, motorized tensioning device 160 may include a limit switch assembly 258. Generally, limit switch assembly 258 may detect current across portions of rotation control assembly 256 and vary the operation of motor 220 according to the detected current. Further details on the operation of limit switch assembly 258 are discussed in detail below.

For purposes of reference, the following detailed description uses the terms "first rotational direction" and "second rotational direction" in describing the rotational directions of one or more components about an axis. For purposes of convenience, the first rotational direction and the second rotational direction refer to rotational directions about a longitudinal axis 284 (see FIG. 12) of shaft 254 and are generally opposite rotational directions. The first rotational direction may refer to the clockwise rotation of a component about longitudinal axis 284, when viewing the component from the vantage point of first end portion 620 of shaft 254. First end portion 620 of shaft 254 may be the end portion associated with fourth gear 237. The second rotational direction may be then be characterized by the counterclockwise rotation of a component about longitudinal axis 284, when viewing the component from the same vantage point.

A brief overview of the operation of motorized tensioning device 160 is described here. A detailed description of the operation is given below. In the incremental tighten mode motor 220 may begin operating in order to rotate crankshaft 222. Crankshaft 222 may turn an input gear of first gear reduction assembly 230, such that the output gear of first gear reduction assembly 230 drives first gear 234 of second gear reduction assembly 232. The intermediate second gear 235 and third gear 236 both rotate, which drives fourth gear 237 in the first rotational direction. As fourth gear 237 rotates, fourth gear 237 may engage and drive torque transmitting system 250 such that spool 240 may eventually begin to rotate in the first rotational direction. This causes lace 152 to wind onto first receiving portion 242 of spool 240.

In the incremental loosen mode, motor 220 may operate to rotate crankshaft 222. In the loosening mode, motor 220 and crankshaft 222 turn in an opposite direction of the direction associated with tightening. The gear reduction system 228 is then driven such that fourth gear 237 of second gear reduction assembly 232 rotates in the second rotational direction. In contrast to the incremental tighten mode, in the incremental loosen mode fourth gear 237 does not directly drive portions of torque transmitting system 250 and spool 240. Instead, the motion of fourth gear 237 in the second rotational direction causes torque transmitting system 250 to momentarily release spool 240, allowing spool 240 to unwind by a predetermined amount after which torque transmitting system 250 reengages spool 240 and prevents further unwinding. This sequence of releasing and catching spool 240 occurs over and over as long as fourth gear 237 rotates in the second rotational direction. Further details of the method by which this incremental loosening is achieved is described in detail below.

Finally, in the open or fully loosen mode, torque transmitting system 250 operates so that substantially no torque is transmitted to spool 240 from any components of torque transmitting system 250. During this mode, spool 240 may rotate more easily in the unwinding direction about shaft 254 (for example, as a wearer manually loosens lace 152 to take off article 100). As slack forms along the lace, secondary winding assembly 260 may apply a small amount of torque to second receiving portion 244 of spool 240, which acts to wind up slack in lace 152.

Torque Transmitting System

FIGS. 10-14 illustrate various schematic views of the components comprising torque transmitting system 250. For purposes of clarity, these components are shown in isolation from other parts of motorized tightening device 160. Additionally, some components are not shown or may be shown in phantom in some views to reveal interior components.

Figure 10:
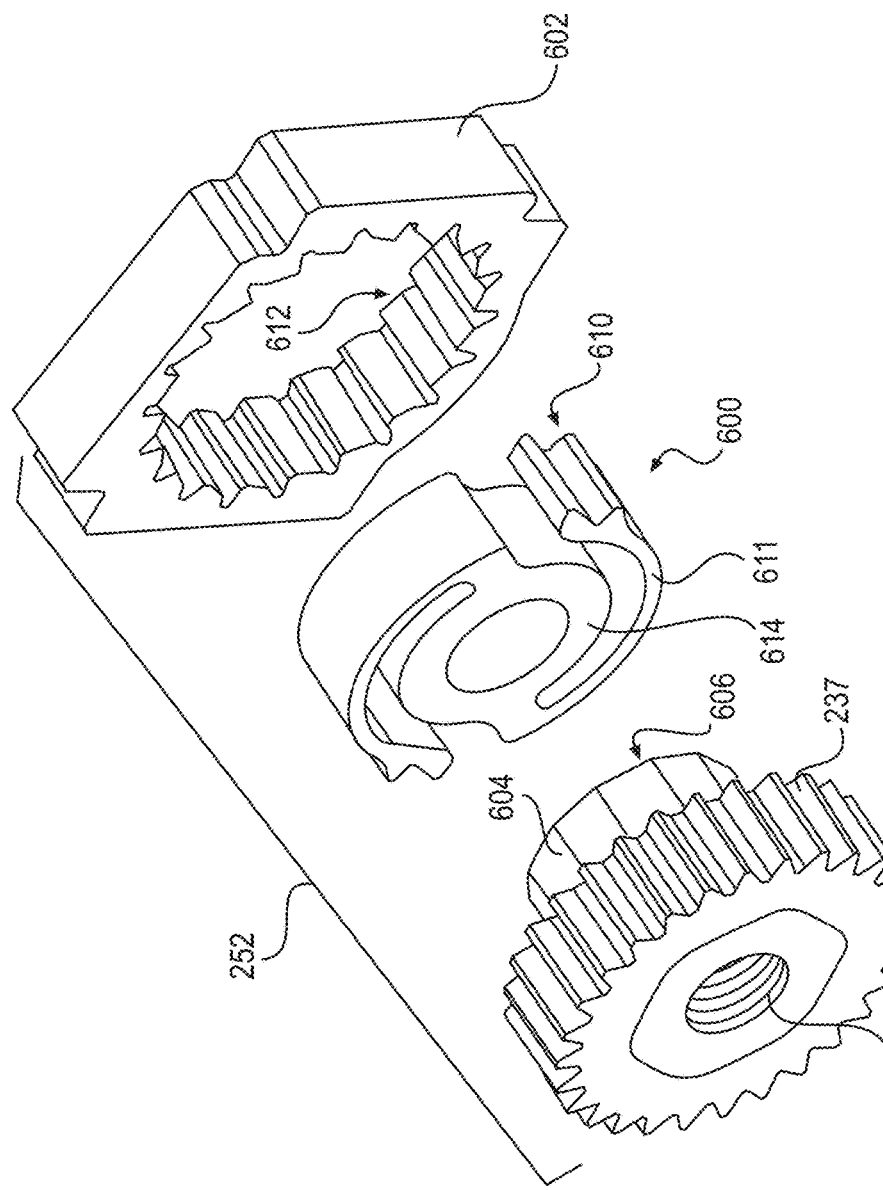
FIG. 10 is a schematic exploded isometric view of an embodiment of a ratcheting assembly.
Figure 11:
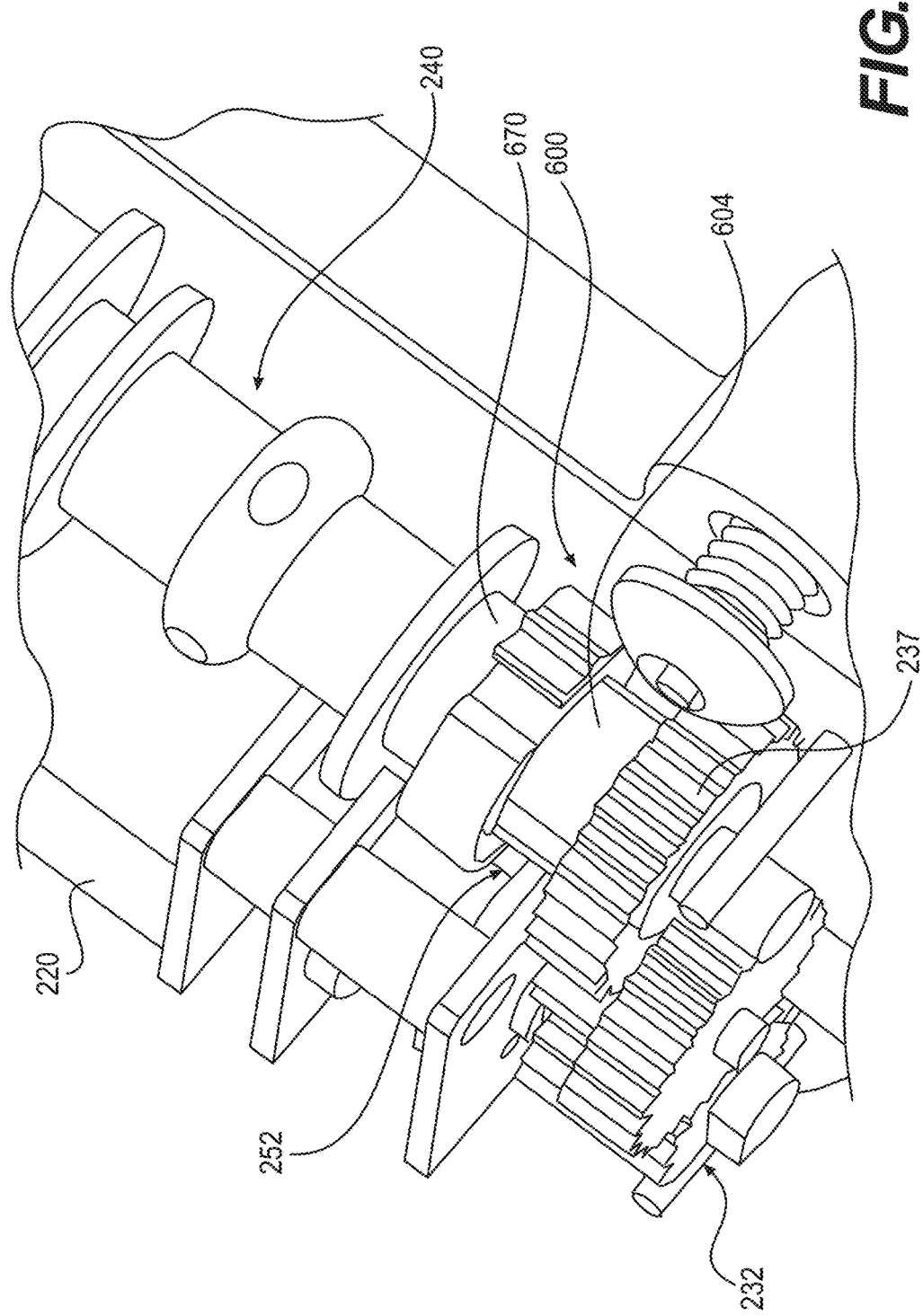
FIG. 11 is a schematic isometric view of a portion of a motorized tensioning system showing a ratcheting assembly clamped to a spool.

Referring first to FIGS. 10 and 11, ratcheting assembly 252 may comprise several components including fourth gear 237, pawl member 600 and ratchet housing 602 (ratchet housing 602 is not shown in FIG. 11 to better show the relative positions of fourth gear 237, pawl member 600 and spool 240). Fourth gear 237 may include an extended boss portion 604. In some embodiments, the extended boss portion 604 further includes a frictional face 606 that contacts pawl member 600. Fourth gear 237 may also include an internally threaded cavity 608 that may engage threading on shaft 254. For purposes of convenience, fourth gear 237 is characterized as part of both ratcheting assembly 252 and second gear reduction assembly 232 as fourth gear 237 acts as an element that confronts and directly drives pawl member 600 and also as a final driving gear of second gear reduction assembly 232. In particular, it is to be understood that characterizing fourth gear 237 as part of one assembly does not preclude it from being associated with a different assembly.

In some embodiments, pawl member 600 is configured to interface with ratchet housing 602. In particular, teeth 610, which extend from pawl arms 611, may engage with corresponding teeth 612 on ratchet housing 602. In some cases the geometry of pawl arms 611 and teeth 610 provide an arrangement where pawl member 600 can rotate within ratchet housing 602 in a first rotational direction, but pawl member 600 is prevented from rotating within ratchet housing 602 in a second rotational direction that is opposite of the first rotational direction.

In some embodiments, pawl member 600 includes a boss engaging surface 614 that confronts and can engage frictional face 606 of fourth gear 237. When frictional face 606 of fourth gear 237 is brought into contact with boss engaging surface 614 of pawl member 600, fourth gear 237 may drive pawl member 600. Moreover, the one-way ratchet design of ratcheting assembly 252 ensures that fourth gear 237 may only drive pawl member 600 in a first rotational direction.

Pawl member 600 may include a spool engaging surface 616 (see also FIG. 16) which confronts a first end 670 of spool 240. When spool engaging surface 616 is pressed against spool 240 with enough frictional force, pawl member 600 may be used to drive spool 240 in the first rotational direction. Thus, in the configuration shown in FIG. 11, with fourth gear 237, pawl member 600 and spool 240 all clamped together under sufficient frictional force, fourth gear 237 may act to drive pawl member 600 and thus spool 240.

Ratcheting assembly 252 is only intended to be exemplary of a one-way torque transmitting mechanism that may be used to transmit torque to a spool. Other embodiments are not limited to ratchet-like mechanisms and could include other one-way mechanisms. Examples of other one-way mechanisms that could be used include, but are not limited to: roller bearings, sprag clutches, ratcheting wheel and pawl as well as other mechanisms.

Figure 12:
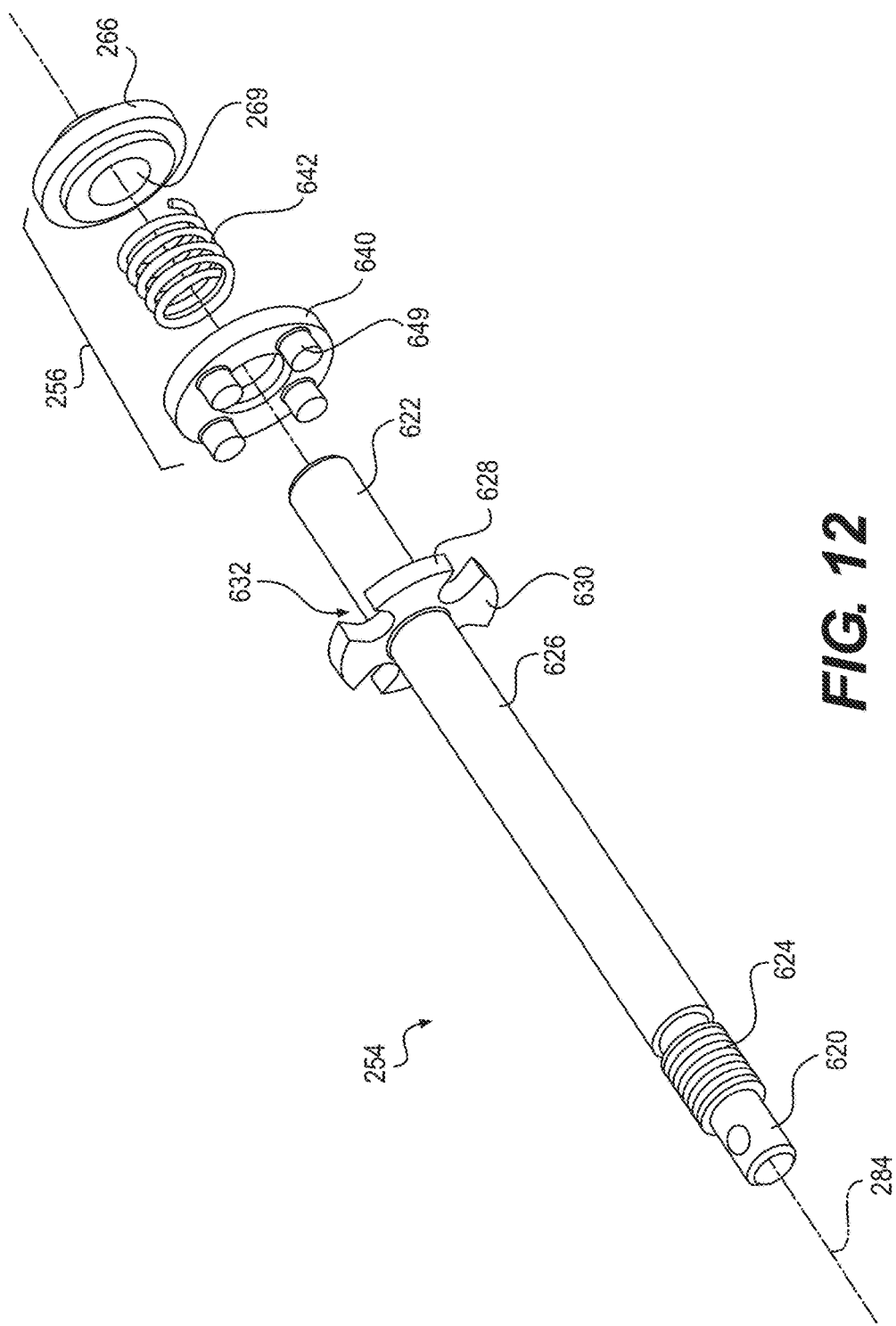
FIG. 12 is a schematic isometric view of an embodiment of a shaft and a rotational control assembly.
Figure 14:
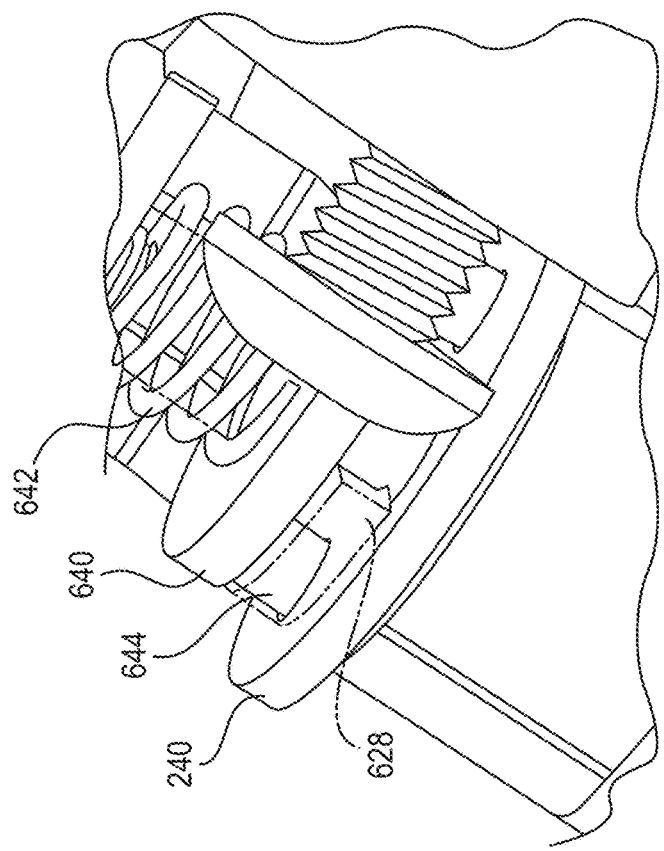
FIG. 14 is another schematic isometric view of a portion of the rotational control assembly of FIG. 13.
Figure 13:
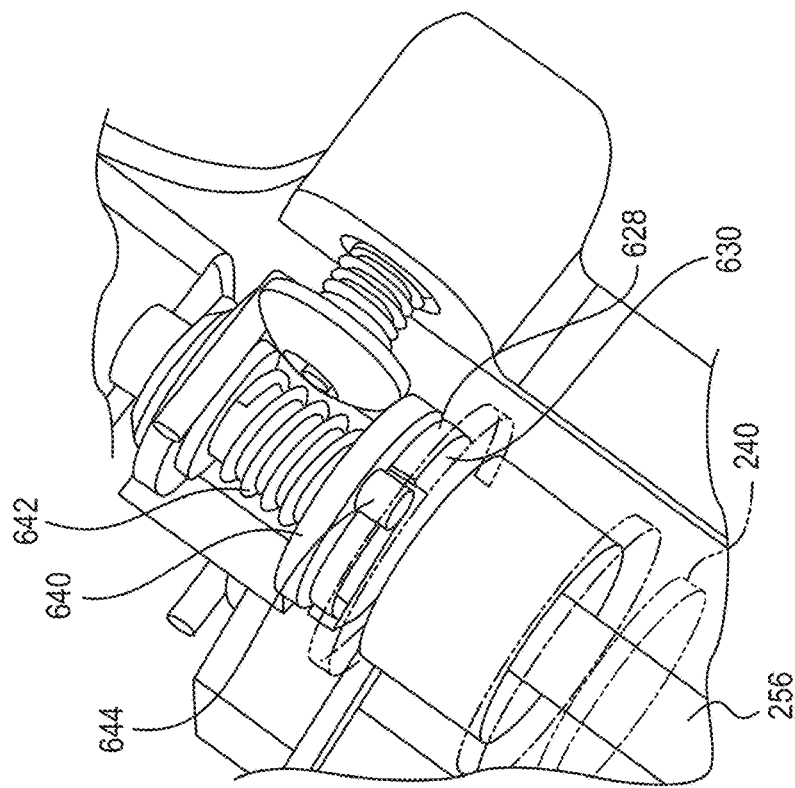
FIG. 13 is a schematic isometric view of a portion of a motorized tensioning system showing a rotational control assembly engaging a spool.

FIGS. 12-14 illustrate various views of additional components of torque transmitting system 250, including shaft 254 and rotation control assembly 256. In particular, FIG. 12 illustrates an isolated exploded view of shaft 254 and rotation control assembly 256, while FIGS. 13-14 illustrate assembled views of some portions of these components from various perspectives.

Shaft 254 may comprise a first end portion 620. In some embodiments, first end portion 620 may include threading 624. In some cases, threading 624 may engage internally threaded cavity 608 (see FIG. 10) of fourth gear 237, which may facilitate the relative axial movement of fourth gear 237 along shaft 254. Shaft 254 may also include a second end portion 622 that engages opening 269 of fixed bearing 266. In some embodiments, an intermediate portion 626 of shaft 254 may be disposed between first end portion 620 and second end portion 622.

Various portions of shaft 254 are configured to receive components of torque transmitting system 250 and spool 240. First end portion 620 and second end portion 622 may be associated with ratcheting assembly 252 and rotation control assembly 256, respectively. Intermediate portion 626 may be inserted within a central cavity 690 of spool 240 (see FIG. 15), such that spool 240 may rotate about intermediate portion 262.

In some embodiments, intermediate portion 626 of shaft 254 further includes a flange portion 628 that extends radially outwards from shaft 254. Flange portion 628 may include a spool engaging surface 630 that contacts spool 240. An opposing surface of flange portion 628 (not shown) may confront rotation control assembly 256. In some embodiments, flange portion 628 may include one or more slots 632.

In some embodiments, rotation control assembly 256 may include an engagement plate 640 and a compression spring 642. In some embodiments, engagement plate 640 further includes pins 644 that extend towards engagement plate 640 and spool 240. In some embodiments, pins 644 may be inserted through slots 632 of flange portion 628. Moreover, in some cases, pins 644 may be inserted into alignment holes 650 of spool 240 (see FIG. 15), which prevents shaft 254 and spool 240 from rotating independently of one another.

As seen in FIGS. 12-14, the components of rotation control assembly 256 are disposed along second end portion 622 of shaft 254. In some embodiments, compression spring 642 may be disposed between engagement plate 640 and fixed bearing 266 so that compression spring 642 may act to bias engagement plate 640 in an axial direction towards flange portion 628 and spool 240.

In other embodiments, alternate methods could be used for releasably coupling a shaft and spool. Examples include other kinds of physical interlocking features or including friction increasing features. As one example, axial compliant friction coupling could be achieved using a wave washer or Belleville washer.

FIG. 15 illustrates an isometric view of an embodiment spool 240 in isolation. As previously described, spool 240 includes provisions for receiving pins 644 of engagement plate 640. In this case, four alignment holes 650 are approximately evenly spaced about a second end face 673. Additionally, this particular view of spool 240 clearly illustrates a slot 675 that may be used for retaining an end of spring member 262.

Figure 16:
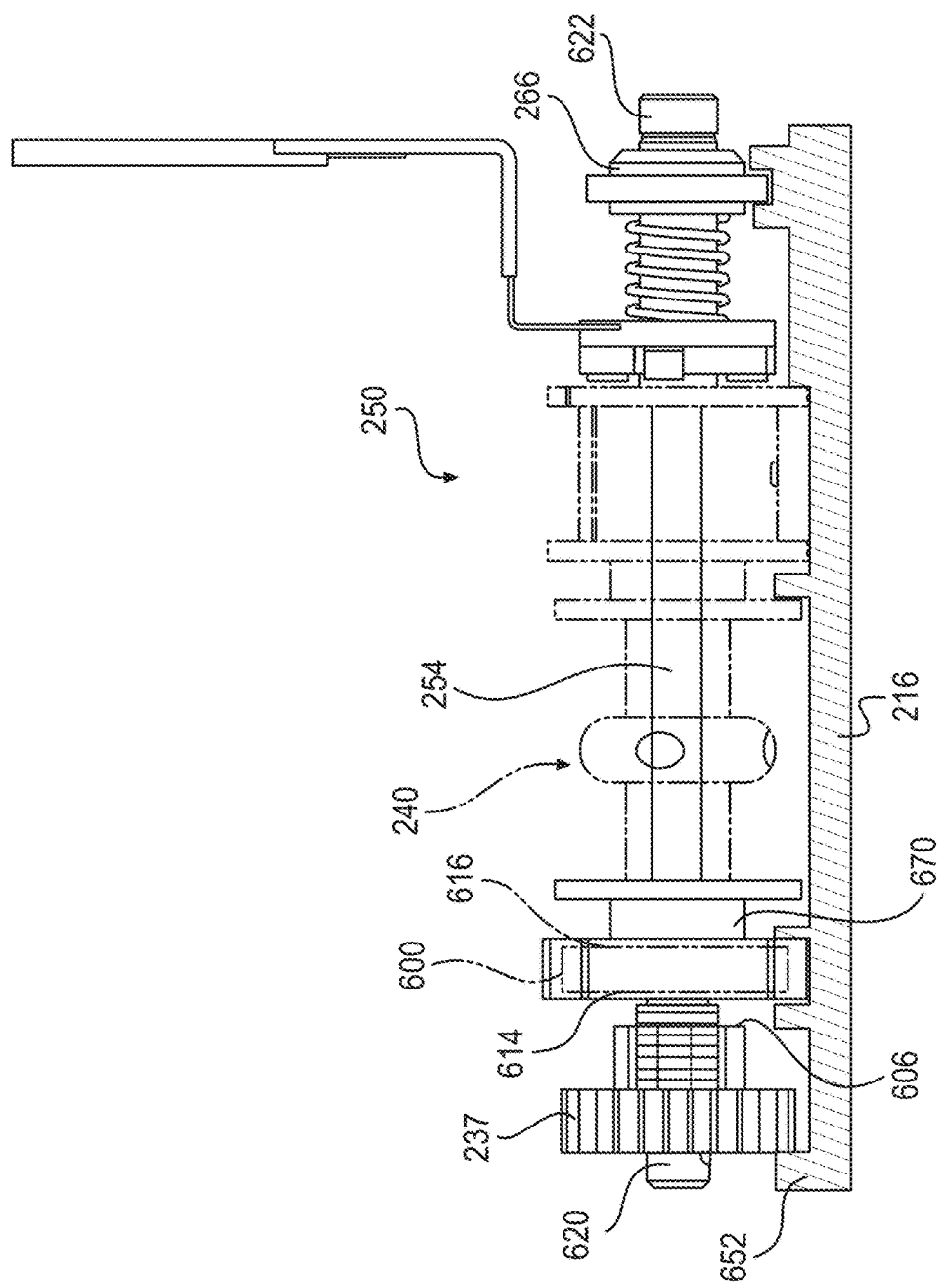
FIG. 16 is a side schematic view of an embodiment of a torque transmitting system.

Referring now to FIG. 16, the components of torque transmitting system 250 are shown in their assembled configuration along shaft 254. For purposes of reference, spool 240 is shown in phantom on shaft 254. In addition, a cross-sectional portion of inner housing portion 216 is shown for reference. As also seen in FIG. 8, when installed within inner housing portion 216, some components of torque transfer system 250 are constrained from any axial movement. For example, spool 240 and ratchet housing 602 are constrained from moving in an axial direction (or along a longitudinal direction of shaft 254). In contrast, fourth gear 237, which is threaded along first end portion 620 of shaft 254, can rotate about shaft 254 and translate axially (because of the threaded engagement) along shaft 254. In some embodiments, a wall portion 652 of inner housing portion 216 limits the axial motion of fourth gear 237 in a direction away from ratcheting assembly 252.

The arrangement shown here for torque transmitting system 250 also allows for both rotation and axial translation of shaft 254. In particular, second end portion 622 of shaft 254 may slide through fixed bearing 266, while first end portion 620 of shaft 254 is disposed in a channel 660 of inner housing portion 216 (see FIG. 8) that also allows for some axial motion of shaft 254. In some embodiments, the amount of axial translation may be limited by features including contact between flange portion 628 and spool 240, as well as possibly other features.

Figure 17:
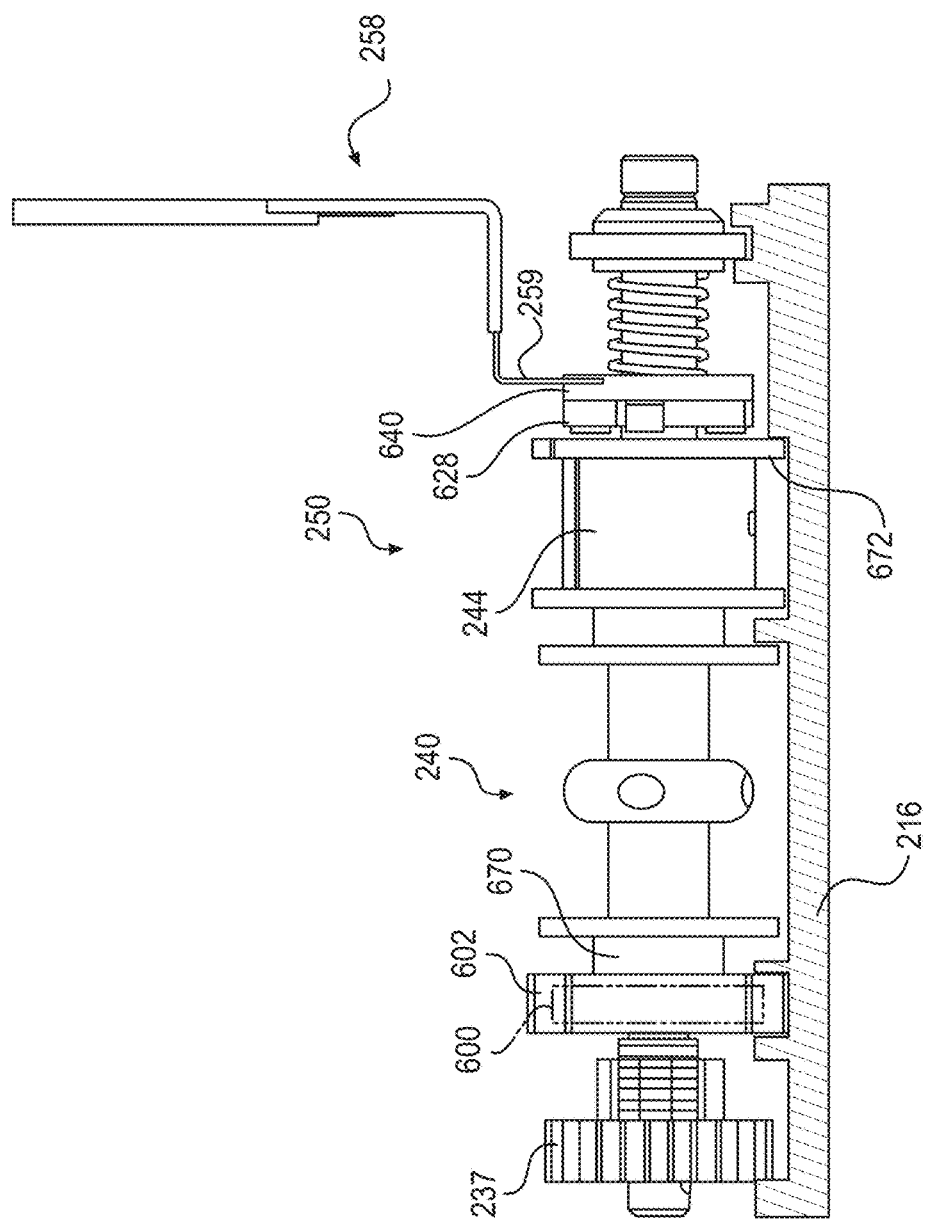
FIG. 17 is a side schematic view of an embodiment of a torque transmitting system in a fully loosened configuration.

FIGS. 17 through 26 illustrate schematic views of torque transmitting system 250 and spool 240 for purposes of illustrating the operation of torque transmitting system 250 during incremental tightening, incremental loosening and full loosening. Referring first to FIG. 17, torque transmitting system 250 is in a configuration where the lace is fully loosened. More specifically, this configuration is one in which no torque is transmitted to spool 240 from torque transmitting system 250. In this configuration, fourth gear 237 may be spaced away from pawl member 600 (disposed within ratchet housing 602) so that no torque is transmitted from fourth gear 237 to pawl member 600. Furthermore, without fourth gear 237 to provide any clamping pressure against pawl member 600 and spool 240, spool 240 may rotate without any substantial resistance at first end portion 670 from pawl member 600. Furthermore, in this configuration engagement plate 640 and flange portion 628 are spaced apart from second end 672 of spool 640, so that spool 240 also does not undergo any resistance to rotation at second end 672. Although features of inner housing portion 612 prevent any axial motion of spool 240, in this configuration spool 240 may rotate in a first rotational direction or a second rotational direction. As previously described, spool 240 may be biased to rotate in a first rotational direction lace winding direction) by secondary winding assembly 260 (not shown), which applies a biasing torque to spool at second receiving portion 244. However, this biasing force may be just large enough to pull in slack and can be overcome relatively easily by a wearer pulling on the laces to unwind them from spool 240. Thus, spool 240 may rotate relatively freely in this configuration, though spool 240 will be biased to wind in slack in the absence of tension applied by the lace to spool 240.

As also shown in FIG. 17, in this fully loosened configuration the contacts 259 of limit switch assembly 258 are pressed against engagement plate 640. This contact with engagement plate 640 provides continuity for the switch, so that current may flow between contacts 259.

Figure 18:
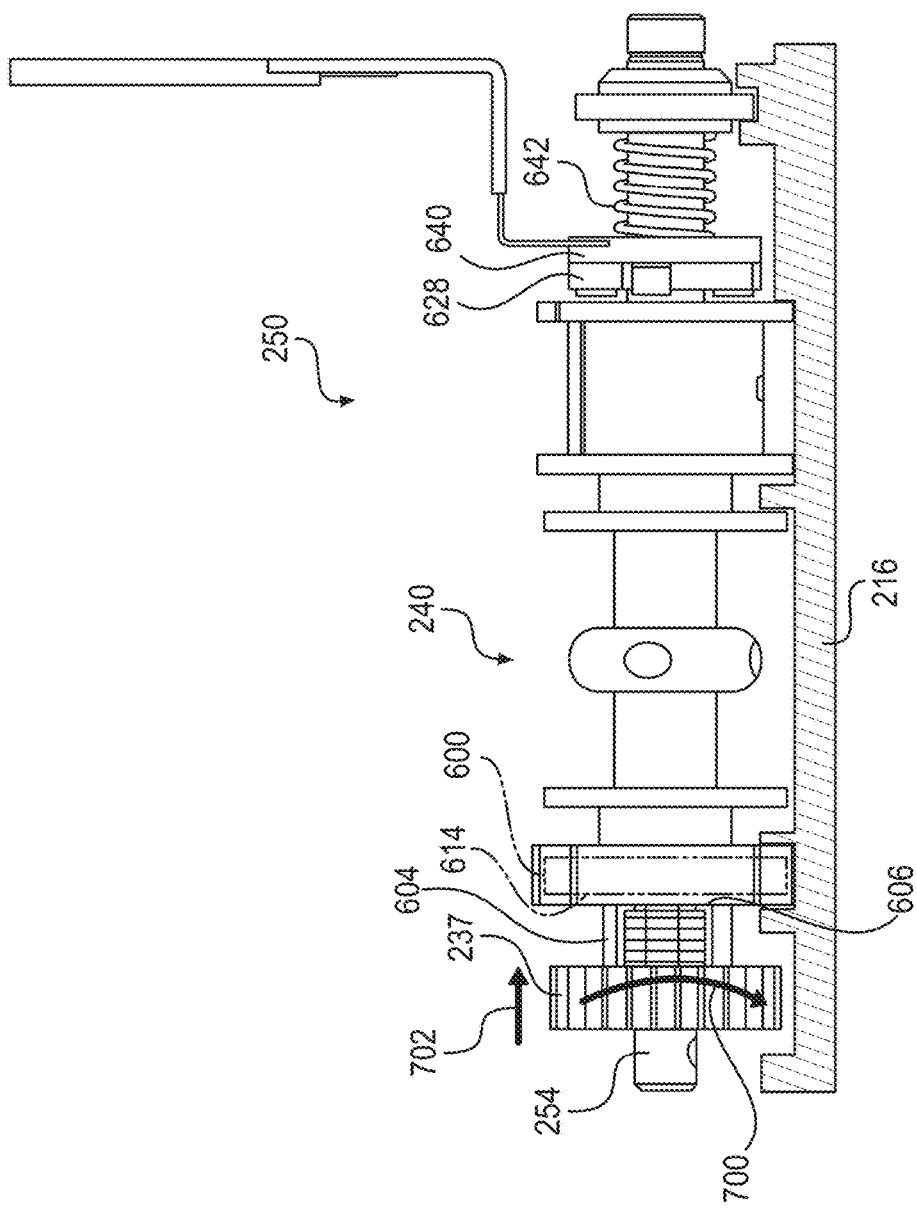
FIG. 18 is a side schematic view of an embodiment of a torque transmitting system in an incremental tightening configuration.

FIG. 18 shows the operation of torque transmitting system 250 as motor 220 (not shown) begins to rotate. Initially, motor 220 drives gear reduction system 228, so that fourth gear 237 is rotated in the first rotational direction (represented schematically by arrow 700). As fourth gear 237 rotates in the first rotational direction, fourth gear 237 translates axially (indicated by arrow 702) towards pawl member 600 because of the threaded interface between fourth gear 237 and shaft 254. Fourth gear 237 continues to rotate and translate axially until frictional face 606 of boss portion 604 contacts and presses against boss engaging surface 614 of pawl member 600. At this point, the preload from compression spring 642 may provide some drag on engagement plate 640 and flange portion 628 (which are coupled) to keep shaft 254 from rotating while fourth gear 237 translates axially along shaft 254. Without this drag, or another source of friction or drag, shaft 254 may be inclined to turn with fourth gear 237 so that fourth gear 237 would not translate axially.

Figure 19:
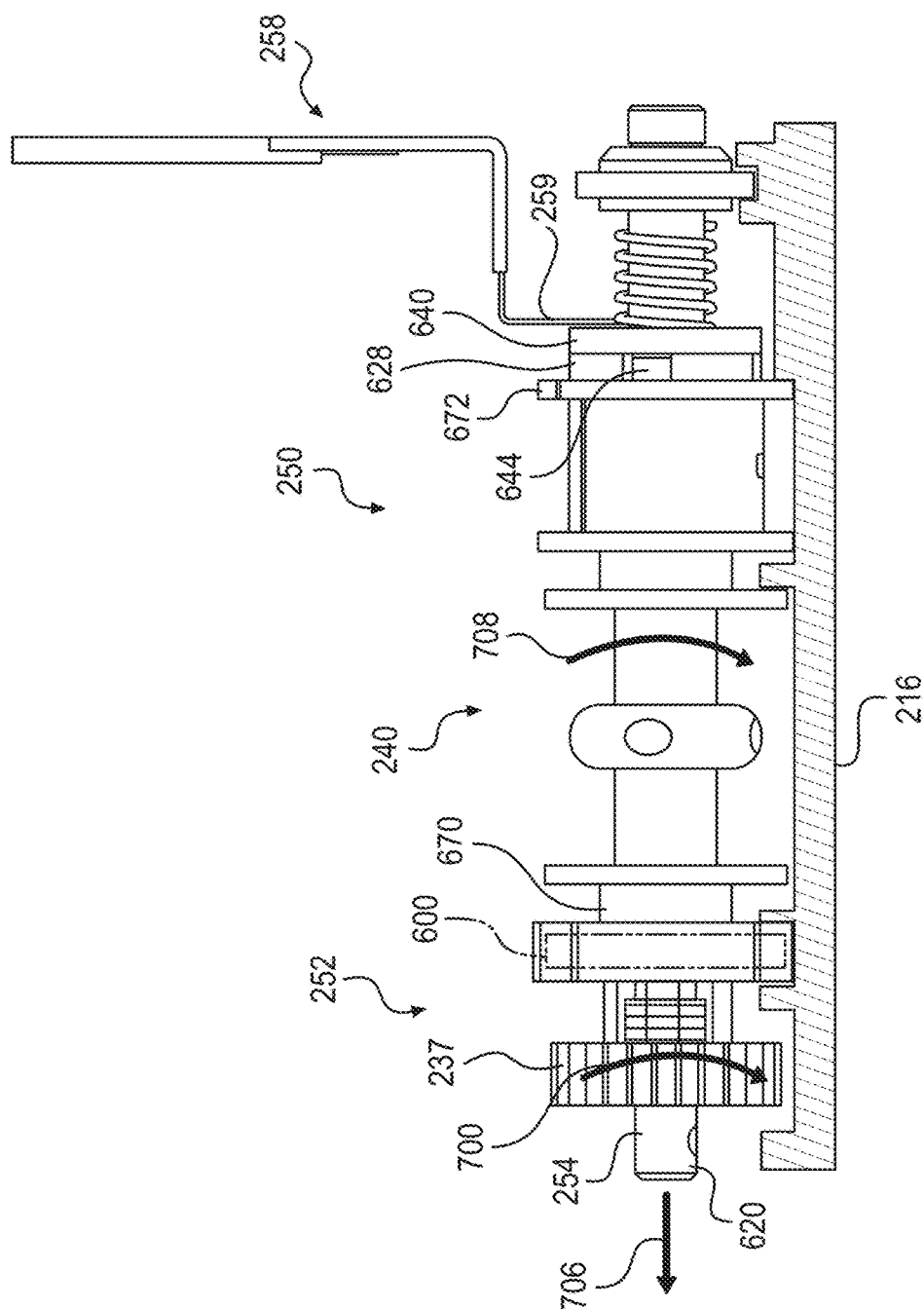
FIG. 19 is a side schematic view of an embodiment of a torque transmitting system in an incremental tighten configuration.

FIG. 19 shows the operation of torque transmitting system 250 in a configuration where spool 240 may begin to wind in lace (i.e., torque transmitting system 250 is in the incremental tighten mode). In this case, motor 220 continues to drive fourth gear 237 in the first rotational direction (indicated schematically as arrow 700), though contact with pawl member 600 prevents any further axial translation of fourth gear 237 along shaft 254. Therefore, as fourth gear 237 continues to turn, shaft 254 is translated axially (indicated schematically as arrow 706) so that first end portion 620 translates further from spool 240. As shaft 254 translates axially, flange portion 628 compresses against second end 672 of spool 240, allowing pins 644 to engage alignment holes (see FIG. 15) of spool 254. This locks shaft 254 and spool 240 together and prevents relative rotation of the two components. The contact between between flange portion 628 and spool 240 prevents any further axial translation of shaft 254. At this point, with ratcheting assembly 252 clamped against first end portion 670 of spool 240, further driving of fourth gear 237 acts to rotate spool 240 in the first rotational direction (indicated schematically by arrow 708). As long as motor 240 continues to drive fourth gear 237, lace may be wound onto spool 240.

It can also be seen in FIG. 19 that as flange 628 moves towards spool 240 and engagement plate 640 follows under the force of compression spring 642, limit switch assembly 258 is separated from engagement plate 640. This breaks the continuity of current between contacts 259.

Figure 21:
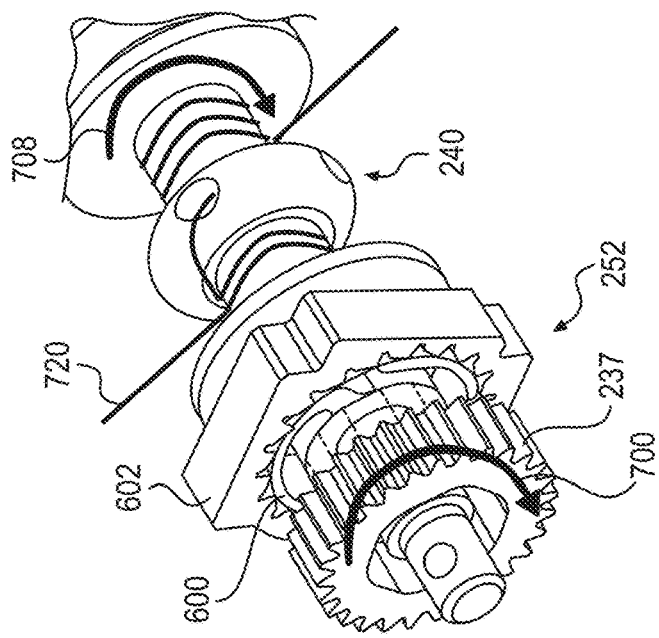
FIG. 21 is a schematic isometric view of the portion of torque transmitting system of FIG. 20, in which the gear, ratcheting assembly and spool are clamped together and the spool is rotated.
Figure 20:
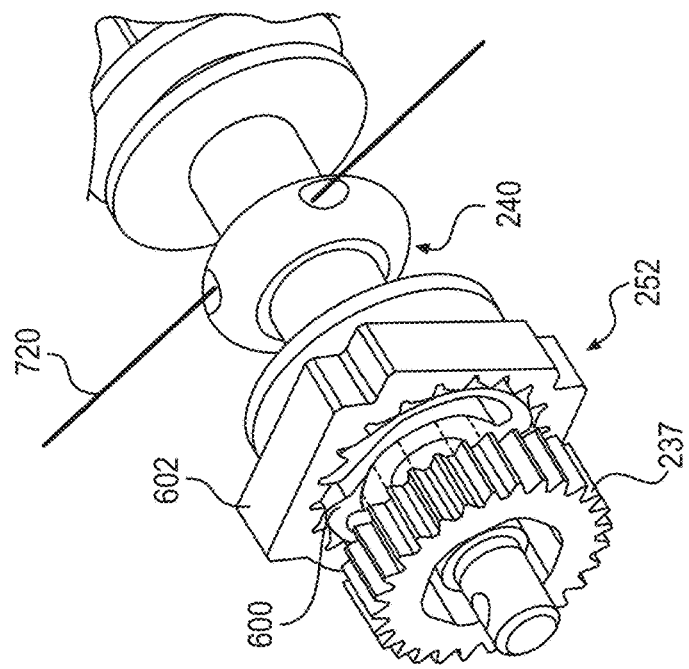
FIG. 20 is a schematic isometric view of a portion of a torque transmitting system as a gear contacts a ratcheting assembly.
Figure 22:
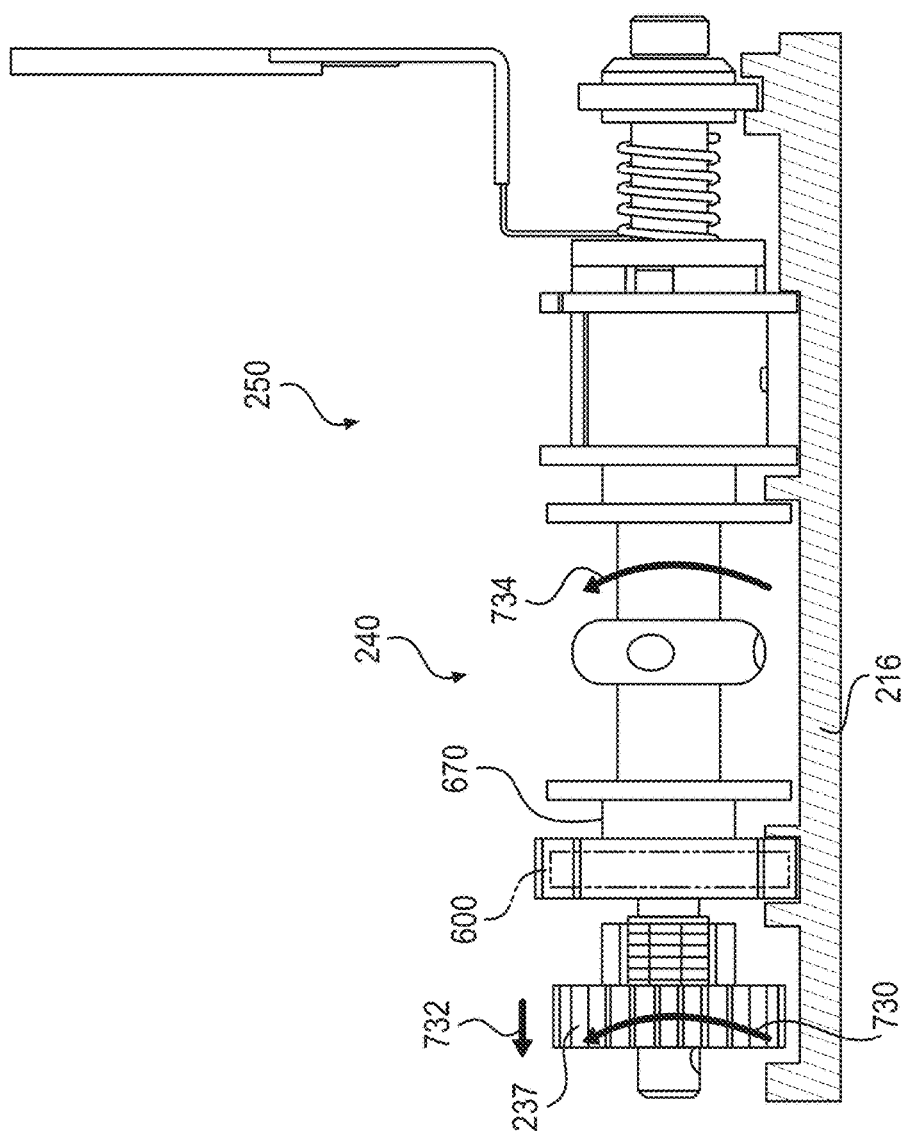
FIG. 22 is a side schematic isometric view of a torque transmitting system in an incremental loosen configuration.

FIGS. 20 and 21 illustrate close up schematic views of some components. For purposes of illustration, a schematic lace 720 is shown with spool 240. Referring to FIGS. 20 and 21, ratcheting assembly 252 ensures that torque can only be transmitted from fourth gear 237 to pawl member 600 and spool 240, and not vice versa. In particular, the one-way operation of ratcheting assembly 252 prevents torque generated by spool 240 from turning pawl member 600, fourth gear 237 and ultimately motor 220. In other words, as previously described, ratcheting assembly 252 functions as a load-holding mechanism that prevents spool 240 from unintentionally rotating in the second rotational direction (i.e., the unwinding direction). This arrangement may help prevent spool 240 from back winding motor 220 in situations where motor 220 stops or the torque applied to spool 240 by the lace exceeds to torque applied to the spool by fourth gear 237.

FIGS. 22-25 show the operation of torque transmitting system 250 in an incremental loosen mode. In some embodiments, incremental loosening may occur in several stages. During a first stage, shown in FIGS. 22 and 23, motor 220 is operated to drive fourth gear 237 in the second rotational direction (indicated schematically as arrow 730). This causes fourth gear 237 to translate axially away from pawl member 600 and spool 240 in a direction indicated schematically by arrow 732. As fourth gear 237 translates away from pawl member 600, the clamping force between fourth gear 237, pawl member 600 and first end 670 of spool 240 is released. During a second stage, shown in FIG. 24, tension in the lace then causes spool 240 to rotate in the second rotational direction (indicated schematically by arrow 734). Because spool 240 and shaft 254 are physically locked together at this stage, shaft 254 rotates along with spool 240 in the second rotational direction (indicated schematically by arrow 736). As shaft 254 rotates the threaded engagement between shaft 254 and fourth gear 237 (as well as the resistance to the rotation of fourth gear 237 provided by gear reduction system 228 and motor 220) causes fourth gear 237 to translate axially towards pawl member 600. In the last stage, shown in FIG. 25, fourth gear 237, pawl member 600 and spool 240 are clamped together, which prevents spool 240 from further rotation in the second rotational direction. These three stages may be repeated in succession to incrementally unwind lace from spool 240.

FIG. 26 shows the operation of torque transmitting system 250 in a fully loosen mode (or full release mode). Referring to FIG. 26, motor 220 may drive fourth gear 237 to rotate in the second rotational direction (indicated schematically by arrow 740) until the lace tension is low enough that spool 240 no longer unwinds. In some embodiments, fourth gear 237 may continue to rotate until fourth gear 237 encounters a hard stop provided by wall portion 652 of inner housing portion 216. With fourth gear 237 unable to translate further, continued driving of fourth gear 237 by motor 220 results in shaft 254 translating axially in the direction indicated schematically by arrow 742 until engagement plate 628 is no longer locked with spool 240 (i.e., until pins 644 disengaged from alignment holes 650 of spool 240). At this point, engagement plate 640 touches contacts 259 of limit switch assembly 258, thereby completing the limit switch continuity, which further causes motor 220 to stop. This leaves spool 240 in a fully loosened state and able to rotate relatively freely, though with some biasing in the first rotational direction provided by secondary winding assembly 260.

Secondary Winding Assembly

A secondary winding assembly may be configured to operate substantially independently of a torque transmitting system. This may allow the winding assembly to draw in slack during various stages of operation of the torque transmitting system. In particular, the secondary winding assembly may be configured to draw in slack in a tensioning member (e.g., lace), which could occur during tightening, loosening and fully loosening of the tensioning member.

Figure 27:
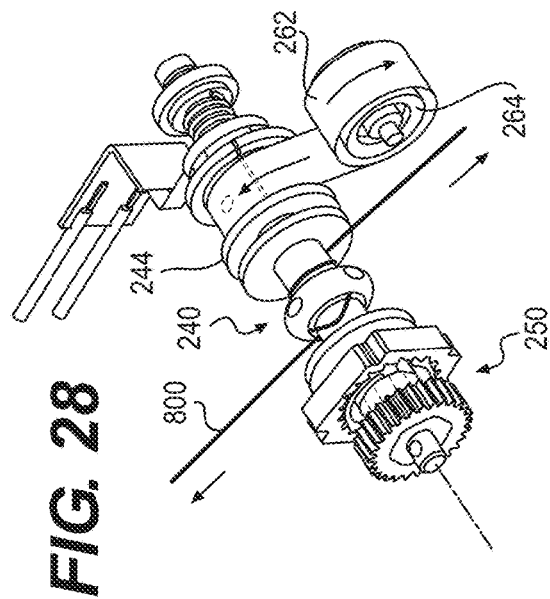
FIG. 27 is a schematic isometric view of a secondary winding assembly operating while a lace is being wound onto a spool.
Figure 28:
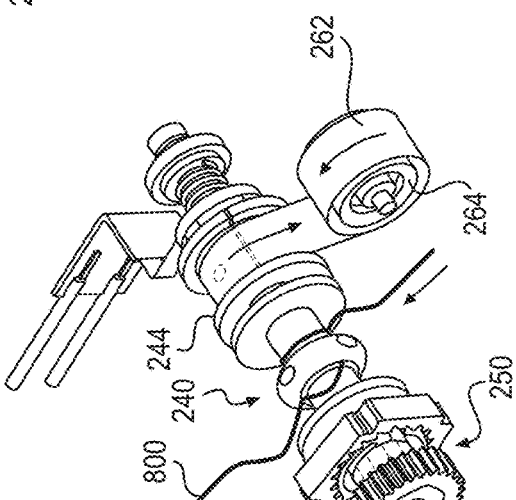
FIG. 28 is a schematic isometric view of a secondary winding assembly operating while a lace is being unwound from a spool due to tension on the lace.
Figure 29:
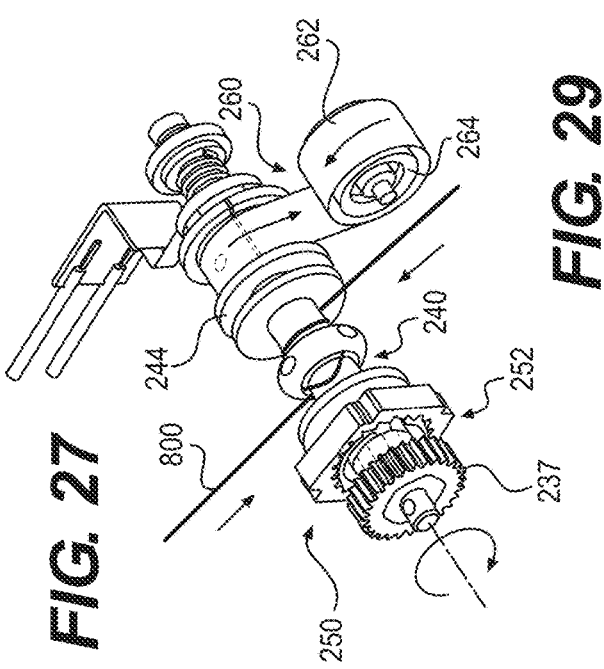
FIG. 29 is a schematic isometric view of a secondary winding assembly operating when a lace has developed some slack near the spool.

FIGS. 27 through 29 illustrate schematic isometric views of some portions of motorized tightening device 160. More specifically, FIGS. 27 through 29 are intended to illustrate the general operation of secondary winding assembly 260 during different operating modes of the system. FIG. 27 illustrates a configuration of motor tightening device 160 operating in a tightening mode. In this mode, fourth gear 237, in cooperation with torque transmitting system 250, drives spool 240 in a first rotational direction and thereby winds lace 800 around spool 240. In this mode, spring member 262 may be wound from spool 240 to spring bearing 264 as spool 240 is driven by the motor.

Referring next to FIG. 28, when motorized tightening device 160 operates in a fully loosened mode, the tension of lace 800 rotates spool 240 in the second winding direction and unwinds lace 800 from spool 240. As spool 240 winds in the second rotational direction, spring member 262 may unwind from spring bearing 264 and onto second receiving portion 244 of spool 240. This allows spring member 262 to return to a default configuration, in which secondary winding assembly 260 tends to bias spool 240 in the winding direction to draw in slack.

Referring next to FIG. 29, motorized tightening device 160 is operating in a mode where no torque is being supplied to spool 240 by a motor. In addition, slack has developed in lace 800 so that lace 800 is not applying much torque to spool 240 either. In this situation, secondary winding assembly 260 provides a biasing force to wind spool 240 in the first rotational direction, as spring member 262 unwinds from second receiving portion 244 of spool 240 and onto spring bearing 264.

Figure 30:
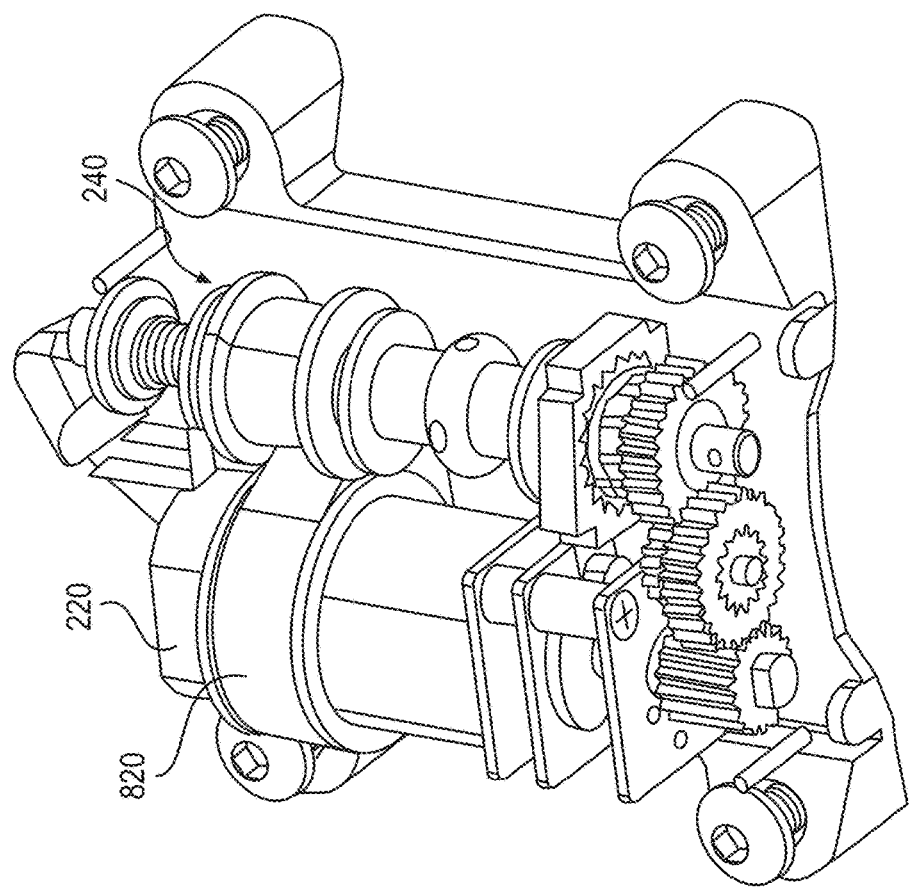
FIG. 30 is a schematic isometric view of motorized tensioning device including an alternative configuration for a secondary winding assembly.

Secondary winding assembly 260 may improve usability of tensioning system 150, by ensuring that slack is rapidly wound up when motor 220 is disengaged. This is desirable so a user can quickly put the article on or take the article off without having to wait for the motor to wind in slack. In the embodiment shown, this rapid slack winding is accomplished using constant force spring that is stored on a freewheeling spool and rewound onto one end of the lace spool. However, in other embodiments, a variety of different elements or systems could be used for this rapid slack winding. For example, in another embodiment a second small motor with either no reduction or light gear reduction could be used for slack winding. In still other embodiments, other spring elements could be used. For example, in another embodiment, an elastomeric torsion spring could be used. In still another embodiment, a geared clock spring could be used. Moreover, in other embodiments, a spring member could be wound onto other components of a tightening system. For example, in the alternative embodiment shown in FIG. 30, spring member 820 is configured to wind around spool 240 at one end, and around motor 220 at another. This alternative arrangement may provide a slightly more compact configuration for a motorized tightening system. In addition to improving the speed of fully winding and unwinding the lace, battery life may be greatly improved over systems that utilize a motor to completely wind and unwind a lace.

Placement

The location of a motorized tensioning device can vary from one embodiment to another. The illustrated embodiments show a motorized tensioning device disposed on the heel of an upper. However, other embodiments may incorporate a motorized tensioning device in any other location of an article of footwear, including the forefoot and midfoot portions of an upper. In still other embodiments, a motorized tensioning device could be disposed in a sole structure of an article. The location of a motorized tensioning device may be selected according to various factors including, but not limited to: size constraints, manufacturing constraints, aesthetic preferences, optimal lacing placement, ease of removability as well as possibly other factors.

In embodiments where motorized tensioning device 160 is disposed externally on upper 102, a wearer may access components by removing a portion of housing unit 212 (see FIG. 1). For example, in some cases spool 240 may be replaceable in the event of a broken lace.

Some embodiments may include provisions for incorporating a motorized tensioning device into removable components of an article. In one embodiment, a motorized tensioning device may be incorporated into an external heel counter. In some cases, an external heel counter may function as a harness for mounting a motorized tensioning device to an article. In such embodiments, the external heel counter may be specially adapted to receive a motorized tensioning device. An example of a heel counter configured for use with a lace tensioning device is disclosed in Gerber, U.S. Pat. No. 2013/0312293, now U.S. patent application Ser. No. 13/481,132, filed May 25, 2012 and titled "Article of Footwear with Protective Member for a Control Device", the entirety of which is hereby incorporated by reference.

Battery and Control Unit

Figure 31:
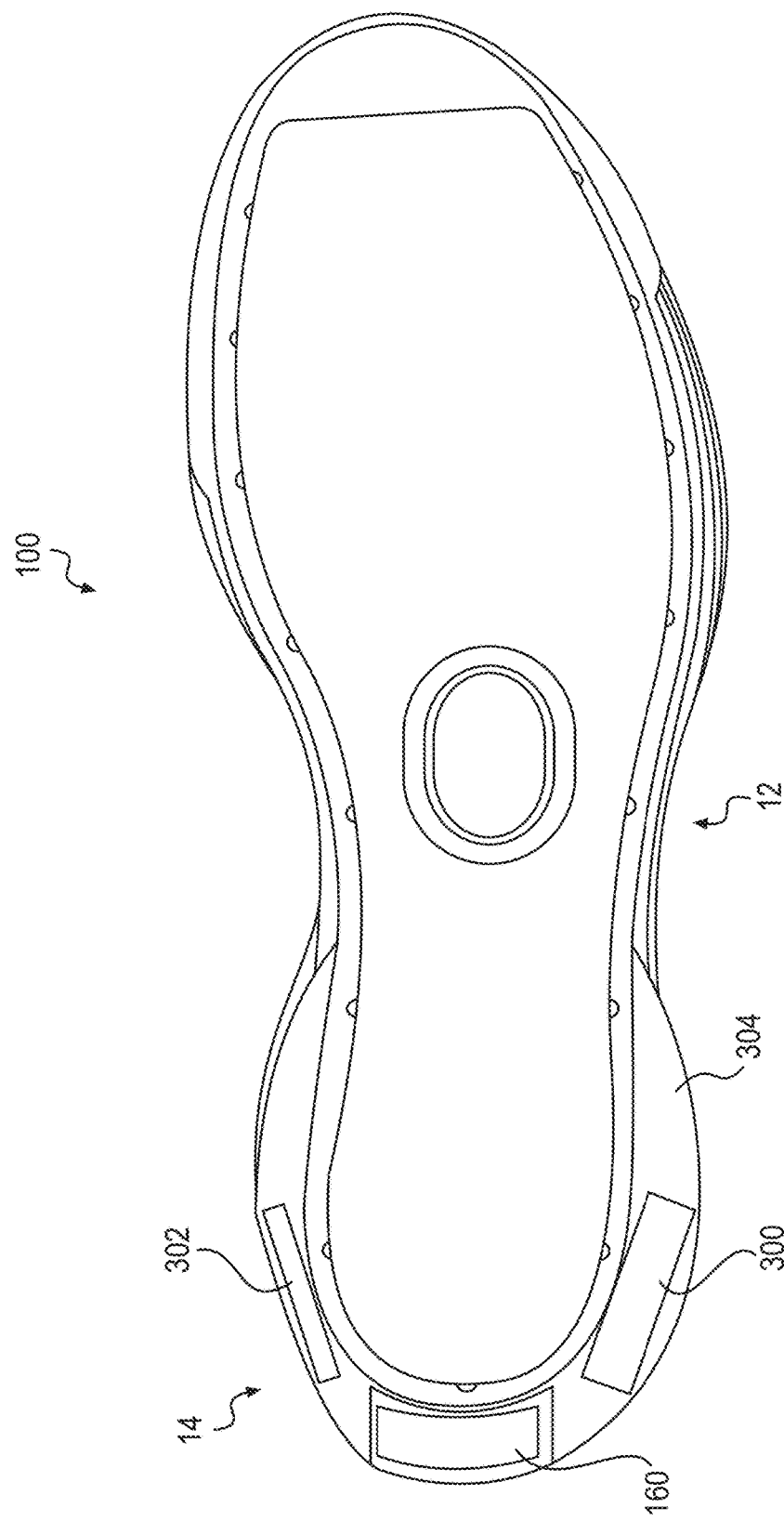
FIG. 31 is a top down schematic view of a portion of an article including an external heel counter, in which the locations of a motorized tensioning device, a control unit and a battery are indicated schematically.

Embodiments may include a battery and/or control unit configured to power and control motorized tensioning device 160. FIG. 31 illustrates a schematic view of an embodiment of article 100 including motorized tensioning device 160, battery 300 and control unit 302. In the embodiment of FIG. 31, motorized tensioning device 160, battery 300 and control unit 302 are all disposed in an external heel counter 304, which may function to receive and protect these components. In other embodiments, however, any of these components could be disposed in any other portions of an article, including the upper and/or sole structure. In some cases, some components could be disposed in one portion of an article and other components could be disposed in another, different, portion. In another embodiment motorized tensioning device 160 could be disposed at the heel of an upper, while battery 300 and/or control unit 302 could be disposed with a sole structure of article 100. For example, in one embodiment the battery and controller unit may be disposed under midfoot portion 12 of article 100 with a cable connection (or a simple electrical contact connection) to motorized tensioning device 160, which may be disposed in heel portion 14. In still other embodiments, a battery and a control unit could be integrated into a motorized tensioning device. For example, in some embodiments, both a battery and a control unit could be disposed within housing unit 212 (see FIG. 1) of motorized tensioning device 160.

Battery 300 is only intended as a schematic representative of one or more types of battery technologies that could be used to power motorized tightening device 160. One possibly battery technology that could be used is a lithium polymer battery. The battery (or batteries) could be rechargeable or replaceable units packaged as flat, cylindrical, or coin shaped. In addition, batteries could be single cell or cells in series or parallel.

Rechargeable batteries could be recharged in place or removed from an article for recharging. In some embodiments, charging circuitry could be built in and on board. In other embodiments, charging circuitry could be located in a remote charger. In another embodiment, inductive charging could be used for charging one or more batteries. For example, a charging antenna could be disposed in a sole structure of an article and the article could then be placed on a charging mat to recharge the batteries.

Additional provisions could be incorporated to maximize battery power and/or otherwise improve use. For example, it is also contemplated that batteries could be used in combination with super caps to handle peak current requirements. In other embodiments, energy harvesting techniques could be incorporated which utilize the weight of the runner and each step to generate power for charging a battery.

Control unit 302 is only intended as a schematic representation of one or more control technologies that could be used with motor tensioning device 160. For example, there are various approaches to motor control that may be employed to allow speed and direction control. For some embodiments, a microcontroller unit may be used. The microcontroller may use internal interrupt generated timing pulses to create pulse-width modulation (PWM) output. This PWM output is fed to an H-bridge which allows high current PWM pulses to drive the motor both clockwise and counterclockwise with speed control. However, any other methods of motor control known in the art could also be used.

Apparel

A tensioning system as described above is not limited to articles of footwear and could be used with apparel, for example. As one particular example, FIGS. 32-36 illustrate an embodiment where a tensioning system 320 is used with an article of apparel 322. In this case, article of apparel 322 may be a layer of clothing that incorporates shoulder pads 324. For purposes of clarity, the description below discusses the use of tensioning system 320 for adjusting a first shoulder pad 326, however, it will be understood that a substantially similar tensioning system could also be used to adjust a second shoulder pad 328 in a similar manner.

Figure 32:
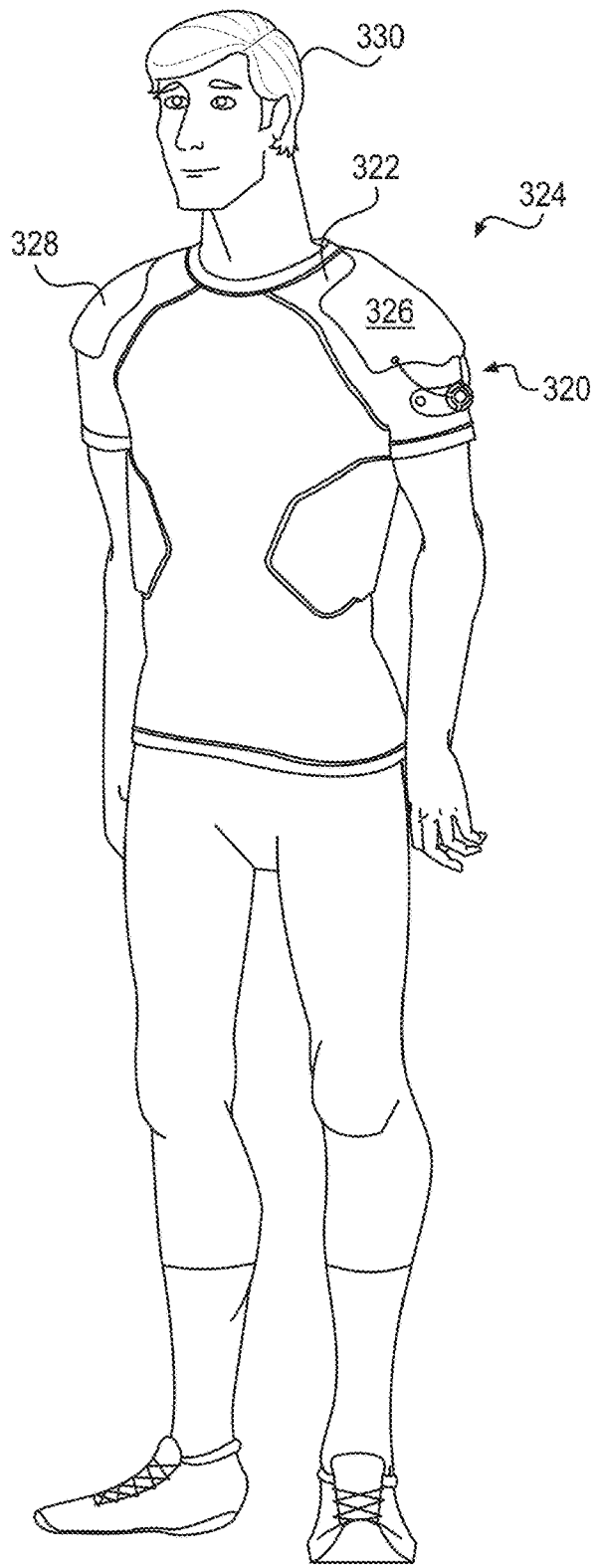
FIG. 32 is an isometric schematic view of an article of apparel including shoulder pads worn by a user.

As seen in FIG. 32, the embodiment discussed here may be used for padding worn by a user 330 playing American football, where shoulder pads are common. However, other embodiments could use this adjustable shoulder pad configuration with any other kinds of clothing configured to be worn by players in any other sports, including, for example, hockey, lacrosse, as well as any other sports or activities requiring shoulder pads. Moreover, it should be understood that the principles discussed here can be used for adjusting any kinds of padding including, but not limited to: elbow pads, knee pads, shin pads, padding associated with the hands and arms, padding associated with the feet and legs, padding associated with the torso, padding associated with the head as well as any other kind of padding known in the art.

Figure 34:
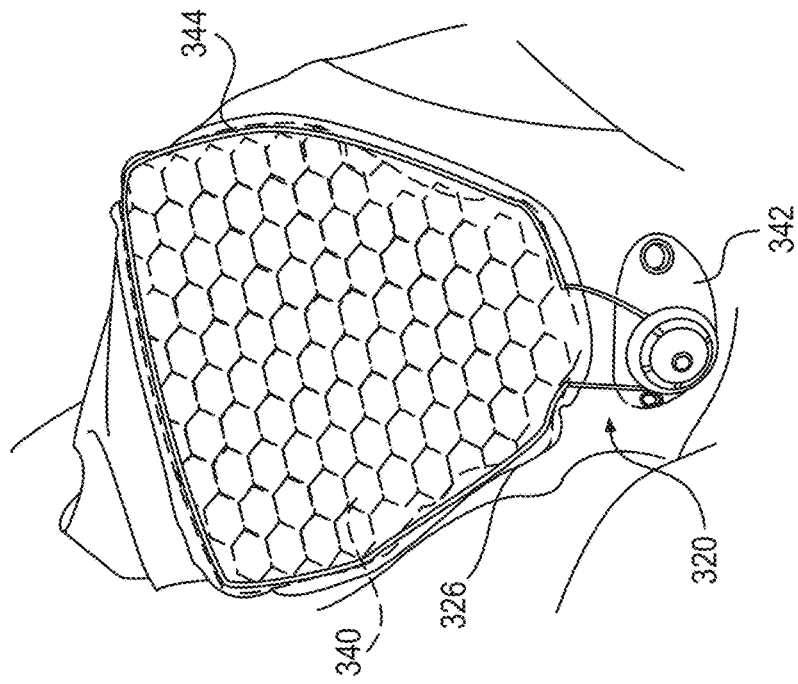
FIG. 34 is a schematic enlarged view of an embodiment of a pad configured with a tensioning system in which a cable of the tensioning system has been tightened around the pad.
Figure 33:
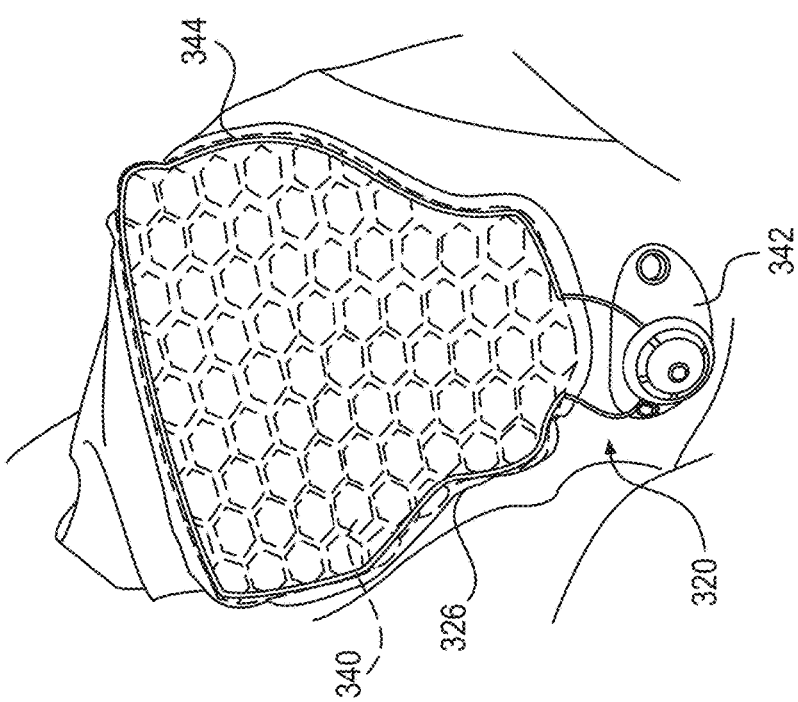
FIG. 33 is a schematic enlarged view of an embodiment of a pad configured with a tensioning system.
Figure 35:
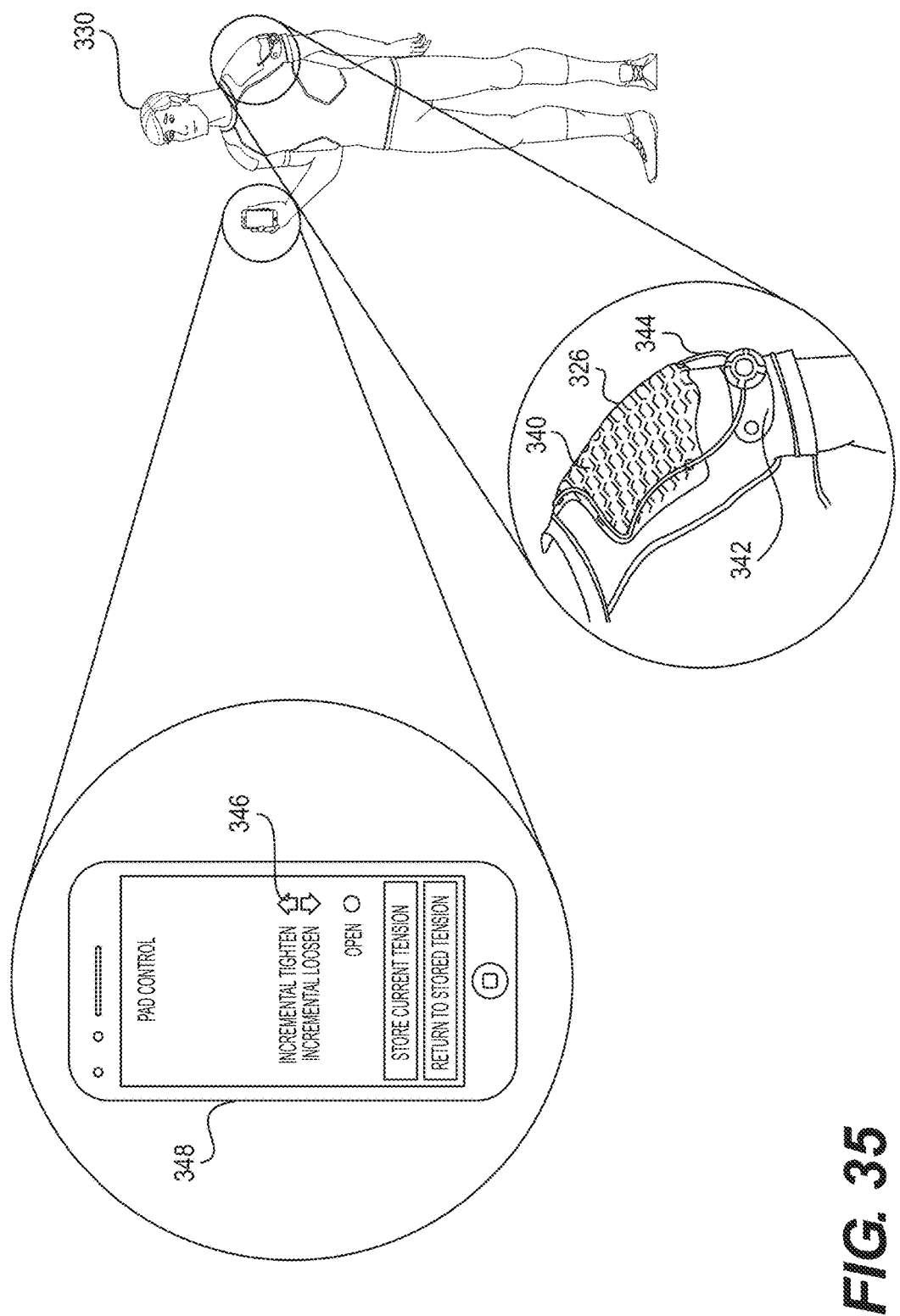
FIG. 35 is a schematic isometric view of an embodiment of a user with an article of apparel having a tensioning device and a remote device for controlling the tensioning device.
Figure 36:
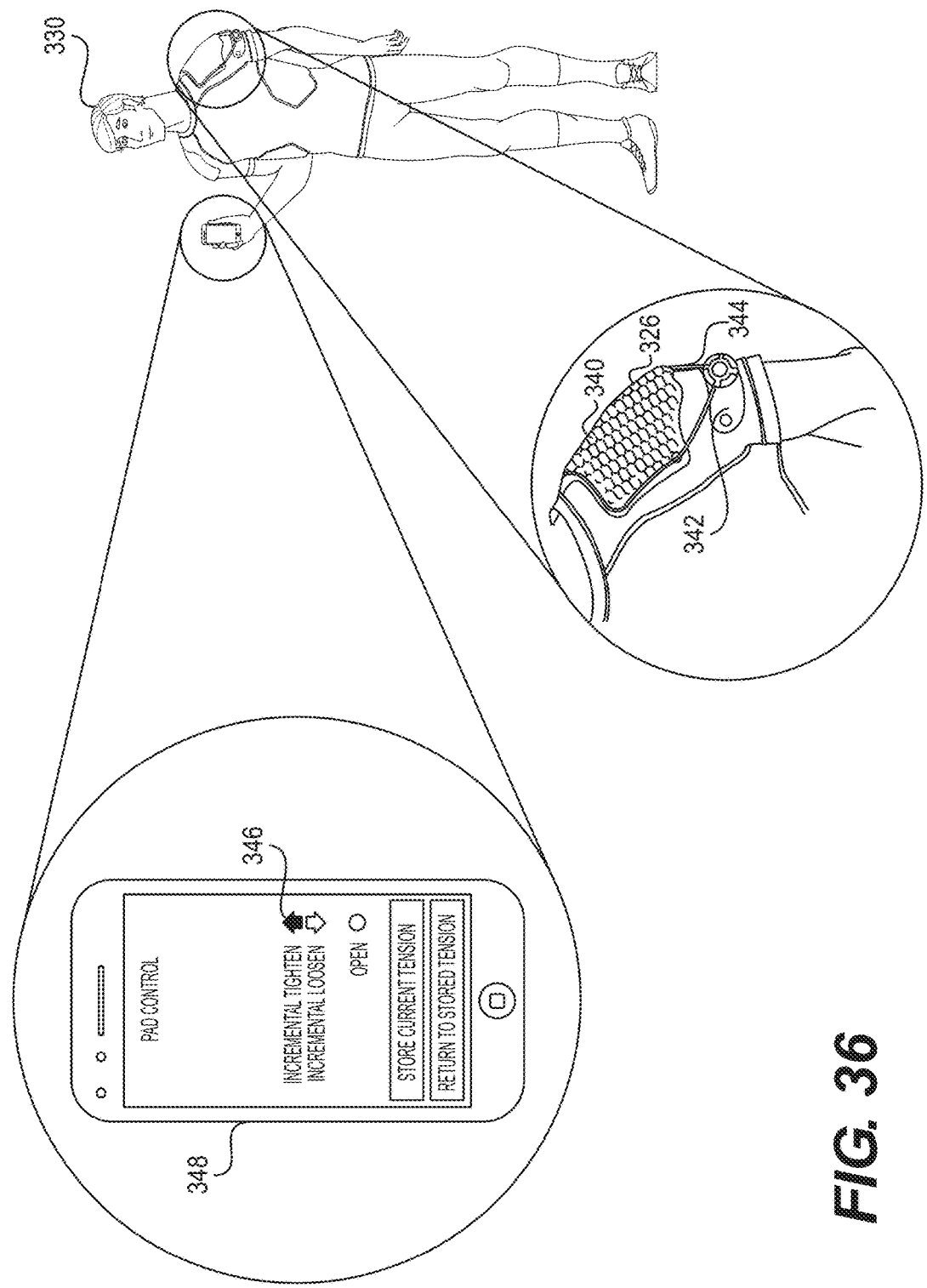
FIG. 36 is a schematic isometric view of the user, apparel and remote device of FIG. 35, in which the user has selected an incremental tighten button and the motorized tensioning device has increased tension around the pad.

Referring now to FIGS. 33 and 34, first shoulder pad 326, referred to hereafter simply as pad 326, may comprise a plurality of padding elements 340. In one embodiment, the geometry of these padding elements 340 is approximately hexagonal. Moreover, the plurality of padding elements 340 may be spaced apart from one another in a default configuration of pad 326.

In order to control the spacing between plurality of padding elements 340, some embodiments can utilize tensioning system 320 to apply an inwardly tensioning force that squeezes plurality of padding elements 340 closer together. In some embodiments, tensioning system 320 may include a motorized tensioning device 342 and a cable 344. In some embodiments, motorized tensioning device 342 is mounted onto article of apparel 322 at a location adjacent to pad 326. Cable 344 extends from motorized tensioning device 342 and wraps around a perimeter of pad 326, thereby surrounding the outer most elements of plurality of padding elements 340. In some cases, cable 344 may be placed through one or more cable guides or lace guides, however in other cases cable 344 may wrap around the perimeter of pad 326 without the use of any guides.

In the default configuration cable 344 is generally loose and applies no tension to pad 326. This is the configuration shown, for example, in FIG. 33. In order to compress or tighten pad 326, user 330 may press the incremental tightening button 346 on remote device 348, which sends tensioning commands to motorized tensioning device 342 (or to a separate control unit of motorized tensioning device 342). As cable 344 is tightened (see FIGS. 34 and 36), cable 344 applies an inward tensioning force on the outer most elements of plurality of padding elements 340, which may squeeze plurality of padding elements 340. This decreases the spacing between adjacent padding elements 340 and increases the overall density of pad 326, which may increase the overall stiffness of pad 326 as compared to the stiffness of pad 326 in the default configuration. In other words, motorized tensioning device 342 may be used to adjust the stiffness of pad 326 from a first stiffness associated with a non-tensioned state of cable 344 to a second stiffness associated with a tensioned state of cable 344, where the second stiffness is substantially greater than the first stiffness. This feature may be used to adjust padding stiffness according to playing conditions (dry, wet, turf, grass, etc.) as well as activity type (practice vs. game) or any other factors.

A tensioning system including a motorized tensioning device may be used with any other kinds of apparel. Some examples of other apparel are shown in FIG. 37, which illustrates schematic views of a backpack 350 and a hat 354, and a corresponding first tensioning system 356 and second tensioning system 358, respectively. For example, first tensioning system 356 may apply tension to a cable 372, which adjusts the tightness of straps 374 of backpack 350. Likewise, second tensioning system 358 may apply tension to a cable or band 380 that circumscribes the periphery of hat 354 and therefore can be used to adjust the size of opening 382 of hat 354.

Further examples of articles that can be used with tensioning systems are disclosed in Soderberg et al., U.S. Patent Application Publication Number 2010/0139057, now U.S. patent application Ser. No. 12/623,362, filed Nov. 20, 2009 and titled "Reel Based Lacing System" (the "'362 application"), the entirety of which is hereby incorporated by reference. Still further examples of articles that can be used with tensioning systems are disclosed in Soderberg et al., U.S. Patent Application Publication Number 2009/0184189, now U.S. patent application Ser. No. 12/355,675, filed Jan. 16, 2009 and titled "Closure System" (the "Closure system application"), the entirety of which is hereby incorporated by reference. It is contemplated that in some embodiments a motorized tensioning device could be incorporated into the articles described in the '362 application as well as articles described in the Closure system application, including a helmet, a hat, a glove, a backpack and/or hydration carrier, a belt, bindings for boots, a wrist guard and a sandal.

In still other embodiments, a tensioning system including a motorized tensioning device can be used with any other kinds of apparel and/or sports equipment including, but not limited to gloves, shirts, pants, socks, scarves, jackets, as well as other articles. Other examples of articles include, but are not limited to: shin guards, knee pads, elbow pads, shoulder pads, as well as any other type of protective equipment. Additionally, in some embodiments, the flexible manufacturing system could be used with bags, duffel bags, purses, backpacks, luggage, various kinds of sportswear and/or sporting equipment.

Alternative Controls

In different embodiments, control of a motorized lacing device can be accomplished using various methods and devices. Referring now to FIG. 38, some embodiments may utilize various kinds of remote devices, including an RF based control bracelet 390. Control bracelet 390 may incorporate one or more buttons for sending commands to a motorized tensioning device. In some cases, control bracelet 390 may include buttons for initiating incremental tightening and incremental loosening commands. In still other cases, additional buttons can be included for initiating any other commands including the open command (or fully loosen command), store tension command and return to stored tension command. Still other cases could incorporate any other buttons for issuing any other kinds of commands.

In some other embodiments, buttons for tightening, loosening and/or performing other functions can be located directly on an article. As an example, some embodiments could incorporate one or more buttons located on or adjacent to the housing of a motorized tensioning device. In still other embodiments, a motorized tightening device maybe controlled using voice commands. These commands could be transmitted through a remote device, or to a device capable of receiving voice commands that is integrated into the article and in communication with the motorized tensioning device.

Sensors

Embodiments can incorporate a variety of sensors for providing information to a control unit of a motorized tensioning system. As described above, in some embodiments an H-bridge mechanism is used to measure current. The measured current is provided as an input to control unit 302 (see FIG. 31). In some cases, a predetermined current may be known to correspond to a certain lace tension. By checking the measured current against the predetermined current, a motorized tensioning system may adjust the tension of a lace until the predetermined current is measured, which indicates the desired lace tension has been achieved.

With current as a feedback, a variety of digital control strategies can be used. For instance, proportional control only could be used. Alternatively, PI control could be used or full PID. In cases some cases, simple averaging could be used or other filtering techniques including fuzzy logic and band-pass to reduce noise.

Still other embodiments can include additional types of sensors. In some cases, pressure sensors could be used under the insoles of an article to indicate when the user is standing. A motorized tensioning system can be programmed to automatically loosen the tension of the lace when the user moves from the standing position to a sitting position. Such a configuration may be useful for older adults that may require low tension when sitting to promote blood circulation but high tension for safety when standing.

Still other embodiments could include additional tension sensing elements. In one embodiment, three point bend indicators could be used in the lace to more accurately monitor the state of the tensioning system, including the lace. In other embodiments, various devices to measure deflection such as capacitive or inductive devices could be used. In some other embodiments, strain gauges could be used to measure tension induced strain in one or more components of a tensioning system.

In some embodiments, sensors such as gyroscopes and accelerometers could be incorporated into a tensioning system. In some embodiments, an accelerometer and/or gyroscope could be used to detect sudden moment and/or position information that may be used as feedback for adjusting lace tension. These sensors could also be implemented to control periods of sleep/awake to extend battery life. In some cases, for example, information from these sensors could be used to reduce tension in a system when the user is inactive, and increase tension during periods of greater activity.

Some embodiments may use memory (for example onboard memory associated with a control unit) to store sensed data over time. This data may be stored for later upload and analysis. For example, one embodiment of an article of footwear may sense and store tension information over time that can be later evaluated to look at trends in tightening.

It is also contemplated that some embodiments could incorporate pressure sensors to detect high pressure regions that may develop during tightening. In some cases, the tension of a lace could be automatically reduced to avoid such high pressure regions. Additionally, in some cases, a system could prompt a user to alter them to these high pressure regions and suggest ways of avoiding them (by altering use or fit of the article).

It is contemplated that in some embodiments a user could be provided with feedback through motor pulsing, which generates haptic feedback for the user in the form of vibrations/sounds. Such provisions could facilitate operation of a tensioning system directly, or provide haptic feedback for other systems in communication with a motorized tensioning device.

Control Methods

Various methods of automatically operating a motorized tensioning device in response to various inputs can be used. For example, after initially tightening a shoe, it is common for the lace tension to quickly decline in the first few minutes of use. Some embodiments of a tensioning system may include provisions for readjusting lace tension to the initial tension set by the user. In some embodiments, a control unit may be configured to monitor tension in those first minutes to then readjust tension to match original tension.

Figure 39:
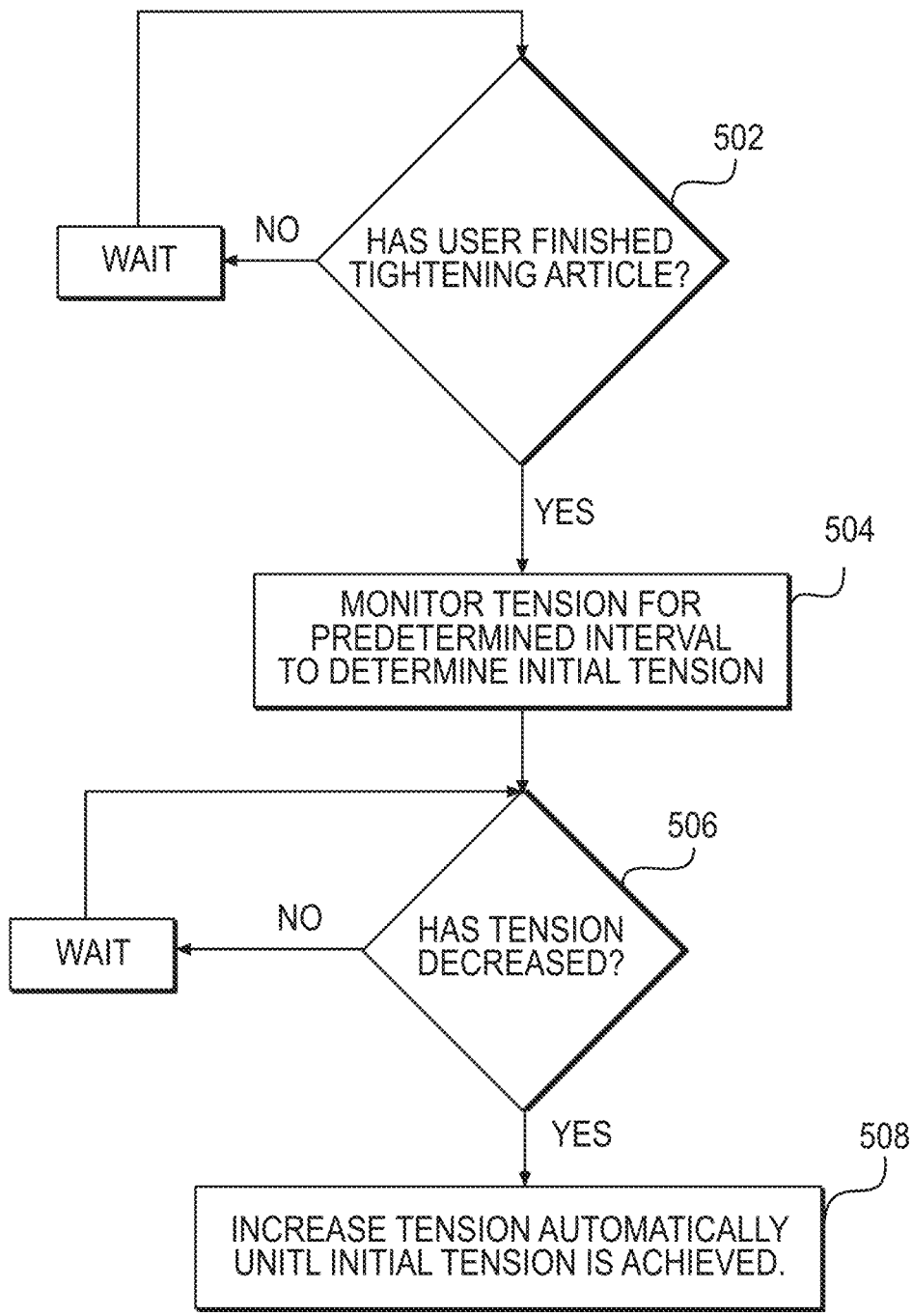
FIG. 39 is a schematic process for automatically controlling tension in an article to maintain an initial tension.

FIG. 39 is a schematic view of an exemplary process for automatically readjusting lace tension to maintain the user desired tension over time. In some embodiments, some of the following steps could be accomplished by a control unit 302 (see FIG. 31) associated with motorized tensioning device 160. In other embodiments, some of the following steps could be accomplished by other components of a tensioning system. It will be understood that in other embodiments one or more of the following steps may be optional.

In step 502, control unit 302 may determine if a user has finished tightening an article. In some cases, control unit 302 may determine that a user has finished tightening a lace if no control commands (e.g., an incremental tighten command) have been received after a predetermined period of time. If control unit 302 determines that the user has finished tightening the article, control unit 302 proceeds to step 504. Otherwise, control unit 302 may wait until it has been determined that the user has finished tightening the article.

In step 504, control unit 302 may monitor tension of the tensioning system (e.g., tension of a lace) for a predetermined interval to determine an initial tension. Methods for monitoring tension, including current sensors and other sensors have been previously discussed above. In some cases, control unit 302 may set the average measured tension over the predetermined interval as the initial tension.

Next, in step 506, control unit 302 may determine if the tension of the tensioning system has decreased. If not, control unit 302 may wait and then revaluate if the tension has decreased. Once it has been determined that the tension has decreased, control unit 302 may proceed to step 508. In step 508, control unit 302 may automatically increase the tension of the tensioning system until the initial tension has been achieved. In some embodiments, after step 508, control unit may wait and again automatically evaluate the tension at step 506. In some embodiments, control unit 302 may be additionally configured to automatically detect overtension and in response automatically decrease the tension of the tensioning system until the initial tension has been achieved. In some embodiments, control unit 302 may be configured to perform cyclic changes in tension, such as to enhance blood circulation.

In some embodiments, instead of only waiting a determined period of time, as illustrated in FIG. 39 and described above, the reevaluation of step 506 may be triggered by sensor information. In one example, sensor-based triggering may replace the waiting, with sensor information causing reevaluation of tension to occur. In another example, waiting may be performed as illustrated in FIG. 39, but with sensor information possibly causing the waiting to be terminated and triggering reevaluation of tension. Sensors providing such information to control unit 302 might include, but are not limited to, pressure sensors in shoe insoles to detect standing and/or rate of motion, bend indicators, strain gauges, gyroscopes, and accelerometers. In some embodiments, instead of or in addition to maintaining an initial tension, the sensor information may be used to establish a new target tension. For example, pressure sensors could be used to measure contact pressures of a brace and automatically adjust used to avoid injury due to high pressure. In some embodiments, control unit 302 may be configured to store sensor information obtained over a period of time to identify triggering events. Additionally, control unit 302 may be configured to upload or otherwise provide stored sensor information to a remote device. Uploaded sensor information may be reviewed and analyzed for purposes including, but not limited to, patient compliance for medical device use. Some embodiments may be configured to operate in two or more different modes. For example, some embodiments could operate in a "normal mode" and a "game mode" (or similarly, a "sports mode" or "active mode"). In the normal mode, the electric motor would be powered down after tensioning in order to save battery life. In contrast, when the game mode is selected by a user, the tension of the system may be continuously monitored and adjusted for maximum performance though at the expense of battery life. By enabling a user to change between these two modes, a user can choose to optimize battery life or optimize performance depending on the needs of the situation. In some embodiments, multiple target tensions may be stored and returned to, for either of the "normal mode" or the "game mode," such as configuring a target tension for sport and a substantially different tension for leisure. In some embodiments, control unit 302 may be configured to frequently, but not continuously, monitor and adjust tension, so as to further extend battery life while achieving some of the benefit of a continuously monitored "game mode."

Figure 40:
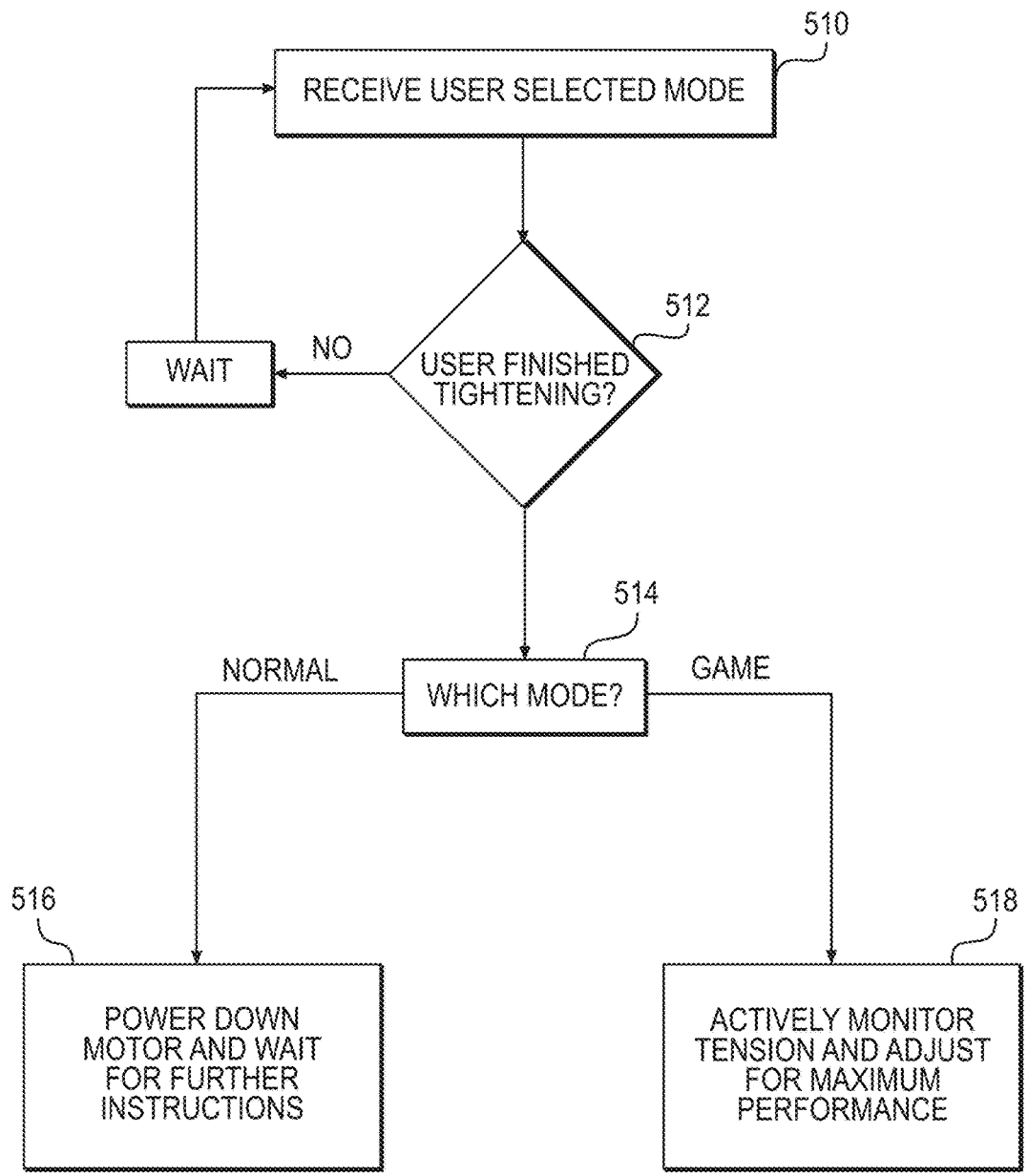
FIG. 40 is a schematic process for automatically controlling tension according to a user selected tensioning mode.

FIG. 40 is a schematic view of an exemplary process for operating a tensioning system in two different modes. In some embodiments, some of the following steps could be accomplished by a control unit 302 (see FIG. 31) associated with motorized tensioning device 160. In other embodiments, some of the following steps could be accomplished by other components of a tensioning system. It will be understood that in other embodiments one or more of the following steps may be optional.

In step 510, control unit 302 may receive the user selected mode. This may be determined by receiving a signal from a remote device, which may prompt a user to select with a "normal mode" or a "game mode". Next, in step 512, control unit 302 may determine if the user has finished tightening the article. If not, control unit 302 waits until the user has finished tightening the article. When the user has finished tightening the article, control unit 302 proceeds to step 514. At step 514, control unit 302 determines which mode has been selected from the information received during step 510. If the user has selected the normal mode, control unit proceeds to step 516, where the motor is powered down and the system awaits further instructions from the user (or other systems/sensors) to save battery power. If, however, the user has selected the game mode at step 514, control unit 302 proceeds to step 518. During step 518, control unit 302 may actively monitor the tension of the article and may automatically adjust the tension to achieve maximum performance.

As another example of a process for automatically controlling a tensioning system, GPS feedback from a remote device could be used to determine if a runner is on flat ground, climbing or descending. The system could automatically adjust the tension of the laces in footwear automatically, for example, by increasing tension in the laces during descent.

Although the exemplary methods described above and shown in FIGS. 39 and 40 are directed to footwear, it will be understood that similar methods could be used for automated operation of other kinds of articles including tensioning systems. In particular, these methods could be used with any of the apparel previously discussed.

Alternative Embodiment of Motorized Tightening Device

Figure 41:
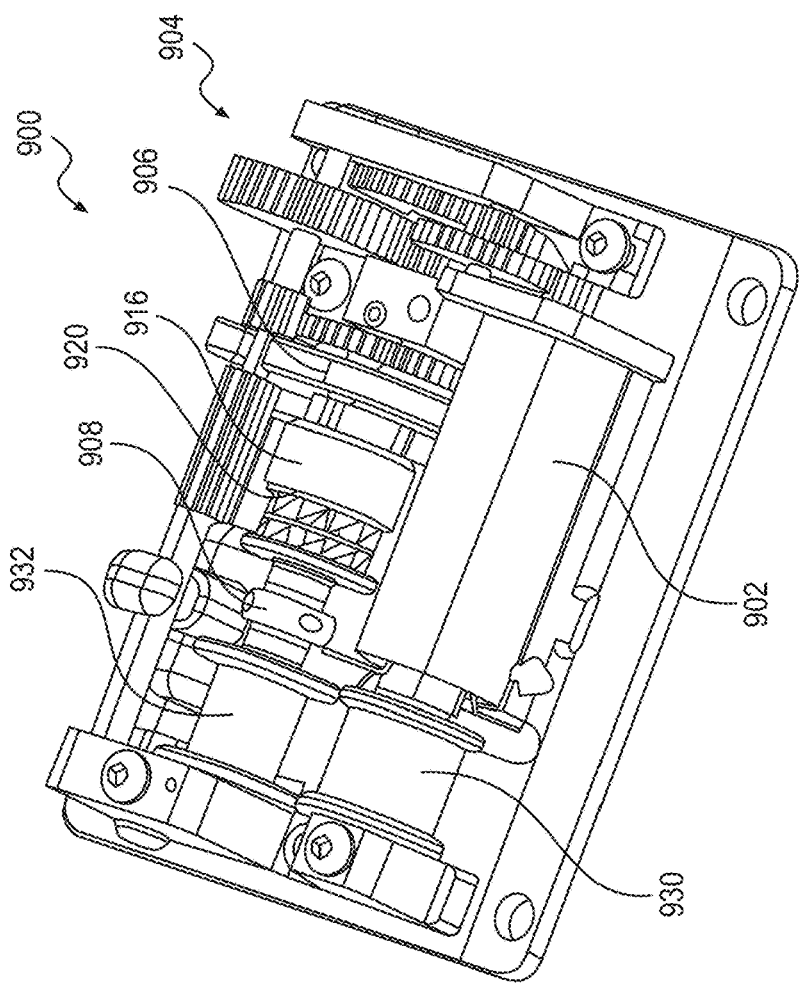
FIG. 41 is a schematic isometric view of an alternative embodiment of a motorized tensioning device.
Figure 43:
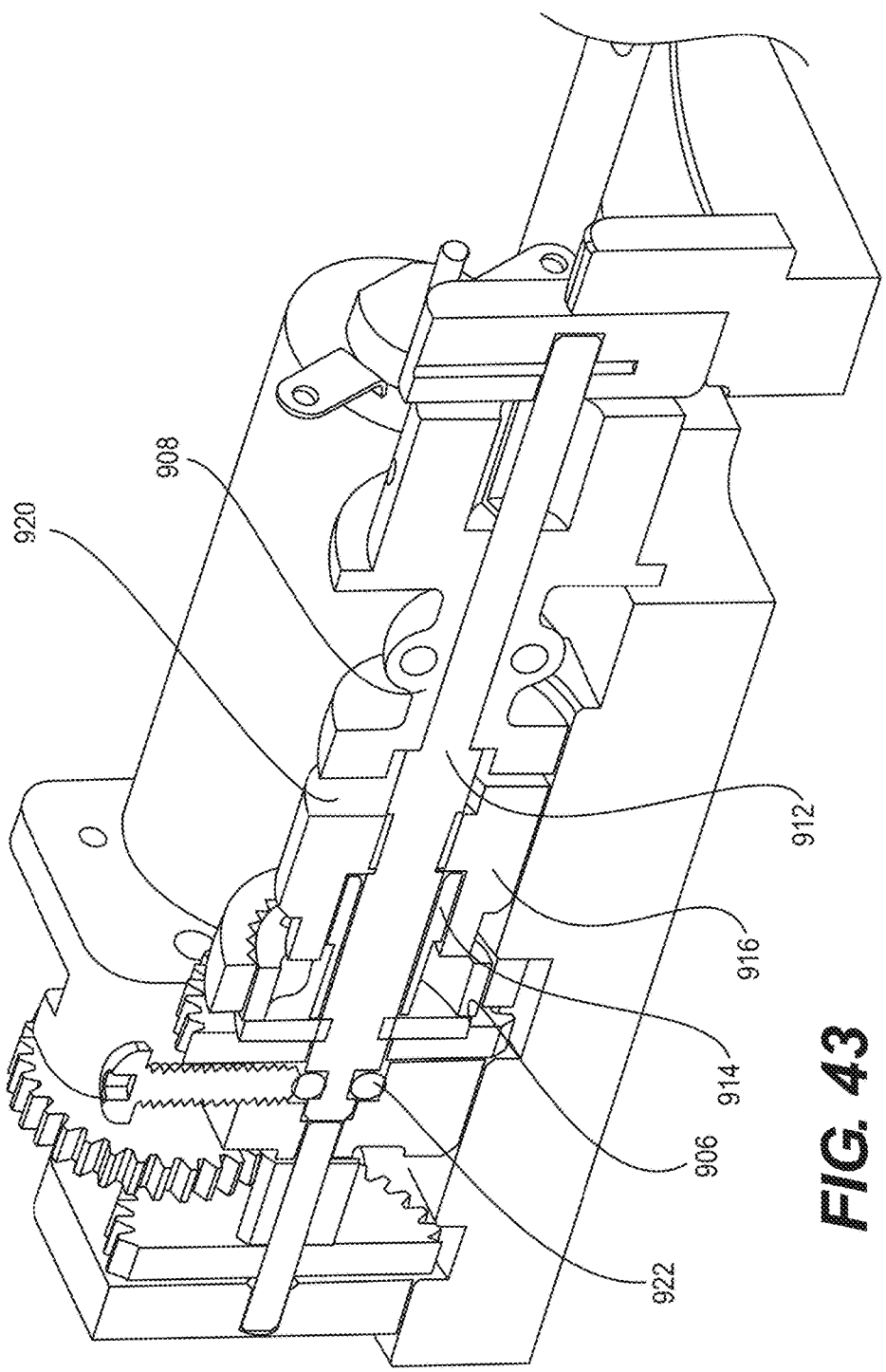
FIG. 43 is a cut-away view of an embodiment of a portion of a motorized tensioning device.

FIG. 41 shows a schematic view of an alternative embodiment of a motorized tensioning device 900. For purposes of describing some internal components, FIG. 43 illustrates a cross sectional view of some components of motorized tensioning device 900. Motorized tensioning device 900 may include some similar provisions as the previous embodiments, for example a motor 902 and a gear reduction system 904 that is driven by motor 902. Gear reduction system 904 as shown here includes 5 stages of spur gears. Other gear reductions that could be employed include: cycloidal, harmonic, and planetary. In some embodiments, the motor 902 and gear reduction system 904 combination may be sized to maximize the tradeoffs between current requirement, size, torque and speed. In the embodiment shown, the gear reduction is approximately 600:1 with an output RPM of 30 and a peak current of 1.2 amps.

Figure 42:
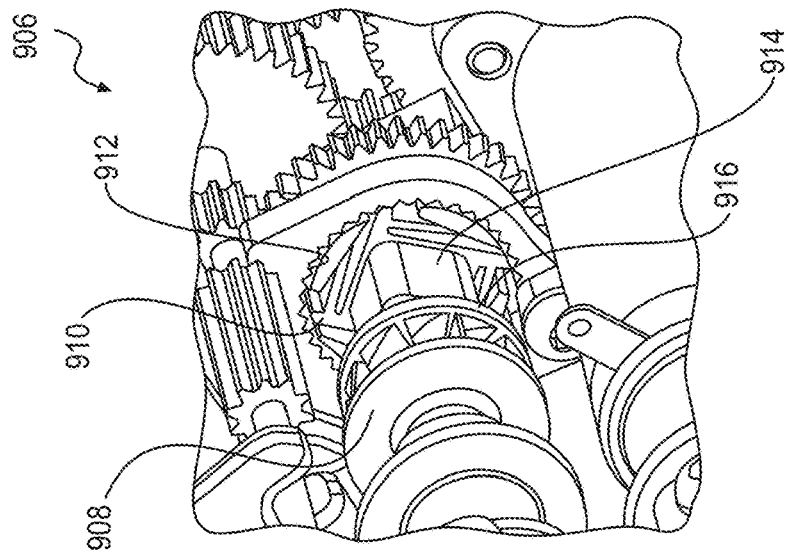
FIG. 42 is an enlarged isometric view of a load-holding mechanism of the motorized tensioning device of FIG. 41.

The output of gear reduction system 904 may enter an incrementally releasable load holding mechanism 906, which is shown in FIG. 42. This load holding mechanism 906 comprises a ratcheting type mechanism, which helps hold any loads applied to spool 908 without potentially back driving motor 902 and/or gear reduction system 904. The purpose is to hold the load without relying on the motor/gearbox to not back drive. Load holding mechanism 906 may hold load on spool 908 even while motor 902 is de-energized. When a small amount of lace tension is desired to be released, motor 902 unwinds and a sweeper element sweeps pawl elements 910 off internal teeth 912 allowing the output to unwind one tooth. This can be repeated as desired to precisely unwind the spool and correspondingly relax lace tension. This is important to allow the user to get to a precise fit. An exemplary load holding mechanism that may be used is disclosed in Soderberg et al., U.S. Patent Application Publication Number 2010/0139057, now U.S. patent application Ser. No. 12/623, 362, filed Nov. 20, 2009 and titled "Reel Based Lacing System", the entirety of which is hereby incorporated by reference.

Referring to FIGS. 41 and 43, the output of load holding mechanism 906 in this embodiment is a male square drive 914. This drive element could be any number of sides or be an external spline. The male square drive mates with a female element 916 with sufficient clearance and of a material for low friction sliding along shaft 912 (see FIG. 43). The female element 916 is driven by the male square drive 914. The opposite end of female element 916 includes a face driving element 920. In the embodiment shown, this is a large number of triangular teeth which can engage or disengage from matching teeth on one flange of spool 908. These teeth could be from as few as one to more than eight. To encourage engagement the teeth may be back drafted from 5 to 60 degrees. In some embodiments, the teeth may be angled at approximately 45 degrees.

The center of female element 916 has a thread (not shown) which can engage threaded portion of shaft 912. When motor 902 is driven in one direction element 916 moves axially as a result of the internal thread and engages the face teeth between itself and corresponding teeth on spool 908. Shaft 912, which is normally stationary, has a frictional element 922 to prevent rotation during axial travel and engagement. When engagement is complete and the face teeth are fully engaged, the external thread of shaft 912 will experience torque. Over a certain torque level, motor 902 and gear reduction system 904 will overcome the torsional friction element 922 and shaft 912 will turn. In the embodiment shown, frictional element 922 is an O-ring on shaft 912 that is contained in a housing. The O-ring pressure can be adjusted via a screw which can clamp down on the O-ring. In other embodiments, this torsion friction could be accomplished by a number of means. For example, in another embodiment, torsional friction could be done as a coulomb frictional device such as an adjustable face clutch for instance using steel or brass against nylon or other brake pad materials and adjustable via an axial spring tensioner. In other embodiments, torsional friction could also be done electrically via a particle clutch or hydraulically via a rotary damper. In some embodiments, the number of turns to reach disengagement can be coordinated if desired with the number of turns to go from full lace tension to no tension. That way, incremental release can be done anywhere in the range of lace that is tensioned.

In the embodiment shown, rapid slack wind may be achieved via a constant force spring (not shown) that is stored on a freewheeling spool 930 and rewound onto one end 930 of spool 908.

In some embodiments, the lace may exit and is tended through radiused eyelets in a housing to prevent lace wear and increase lace fatigue life. In some embodiments, these exits may be located at least ½ of the spool diameter away from the spool to help the lace more or less level wind onto the spool to maximize capacity.

In some embodiments, a user initiated manual release element is also provided should the user every find themselves in tightened shoes with no remaining battery life. Many approaches could be used to manually disengage the spool from the load holding and motor/gearbox mechanism. For instance a tapered blade (not shown) can be inserted between the teeth on spool 908 and element 916 to separate them via a spring element allowing axial movement of spool 908 in the separation direction.

Figure 53:
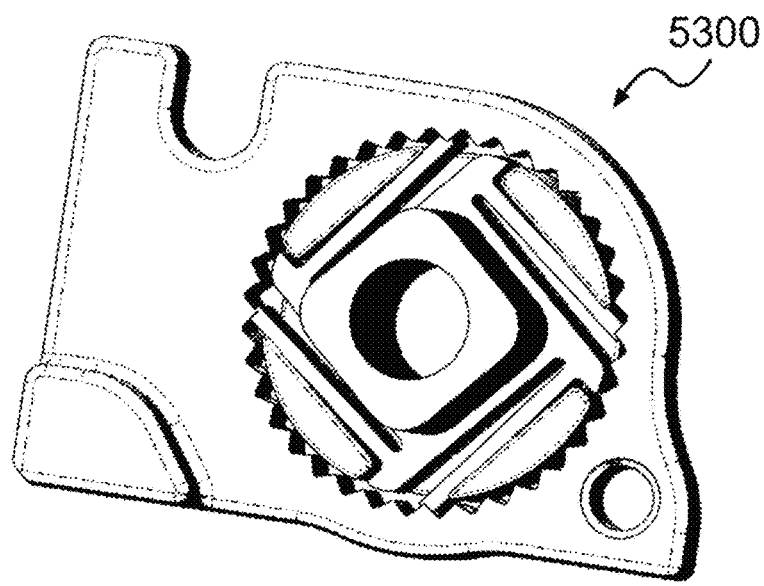
FIGS. 53-54 illustrate examples of ratcheting mechanisms for different embodiments of a motorized tensioning device.
Figure 54:
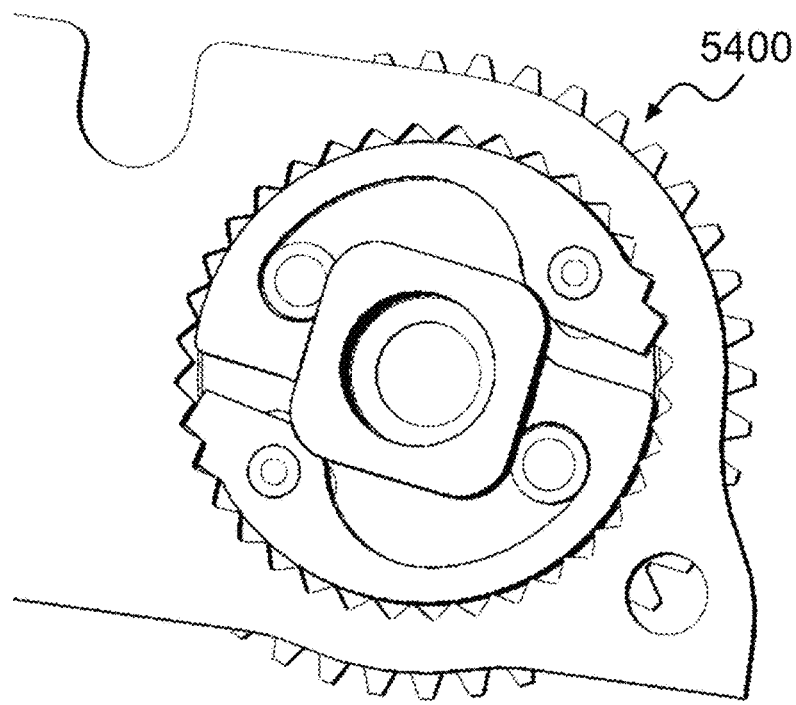

In addition, other example configurations of ratcheting mechanisms for different embodiments of a motorized tensioning device can be understood by studying devices 5300 and 5400 illustrated in FIGS. 53 and 54.

Alternate Tension and Release Mechanism

Figure 44:
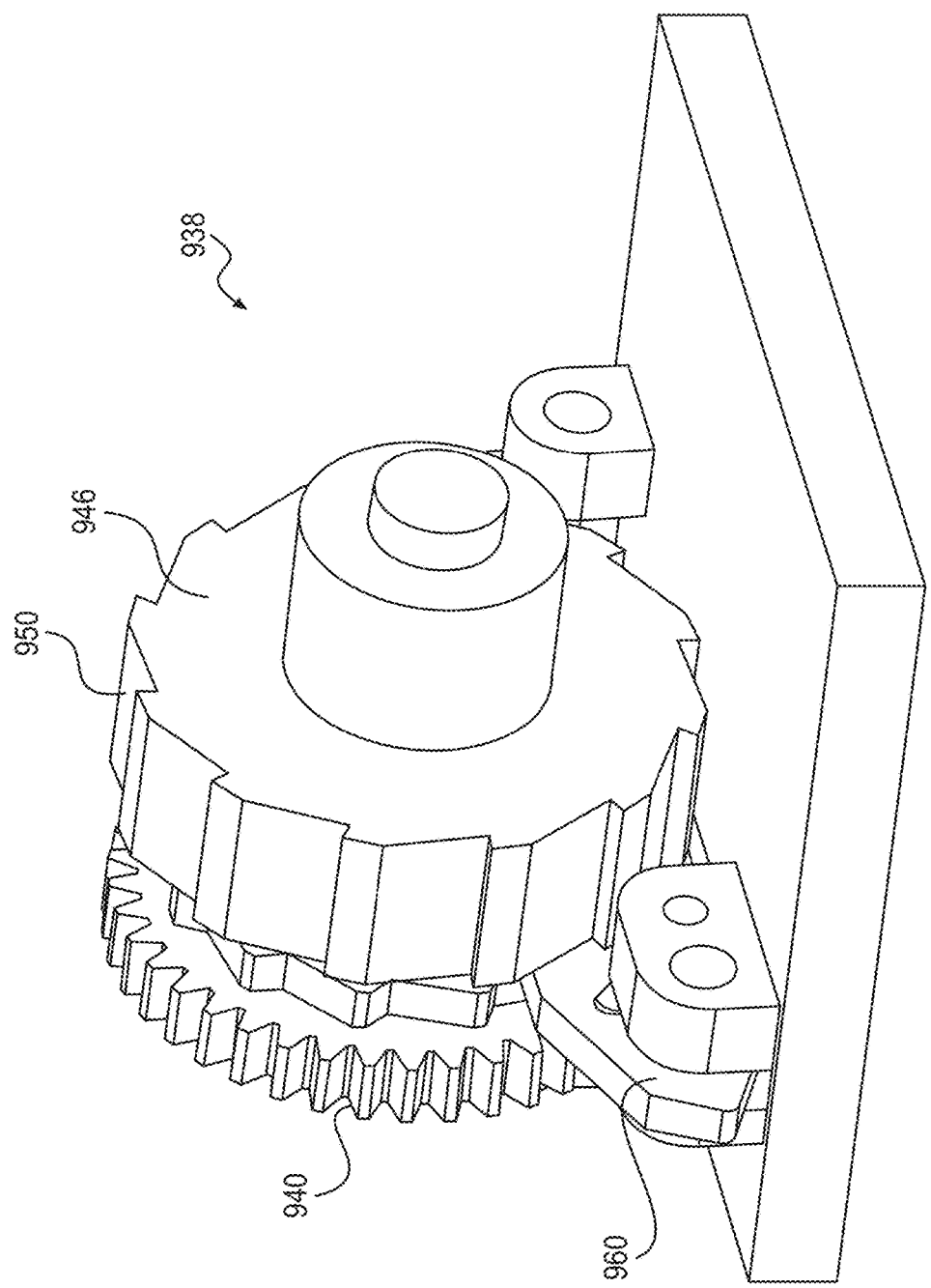
FIG. 44 is an isometric view of another embodiment of a load holding mechanism for a motorized tensioning device.
Figure 45:
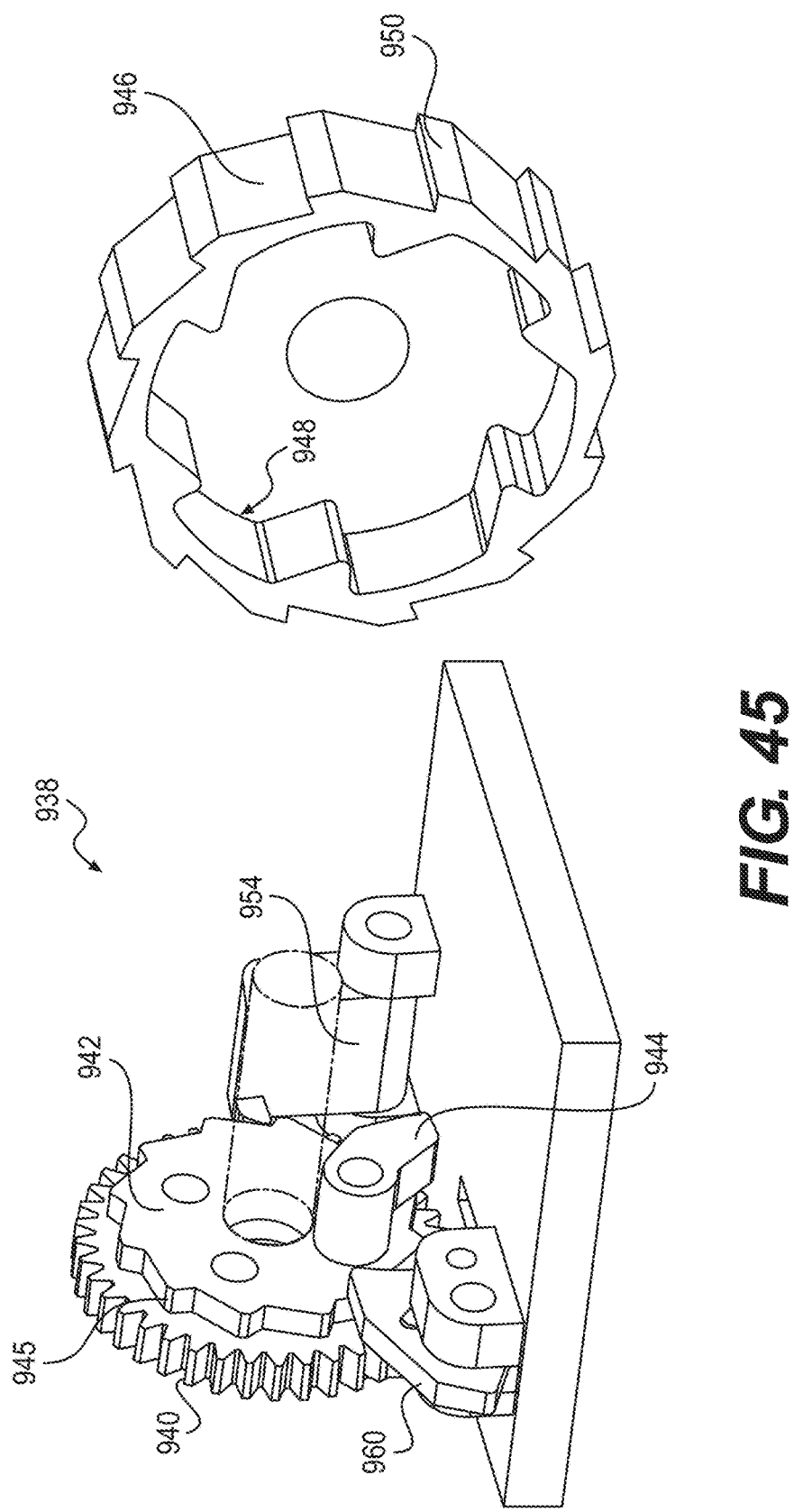
FIG. 45 is an isometric view of the load holding mechanism of FIG. 44, in which an output ring has been removed.
Figure 47:
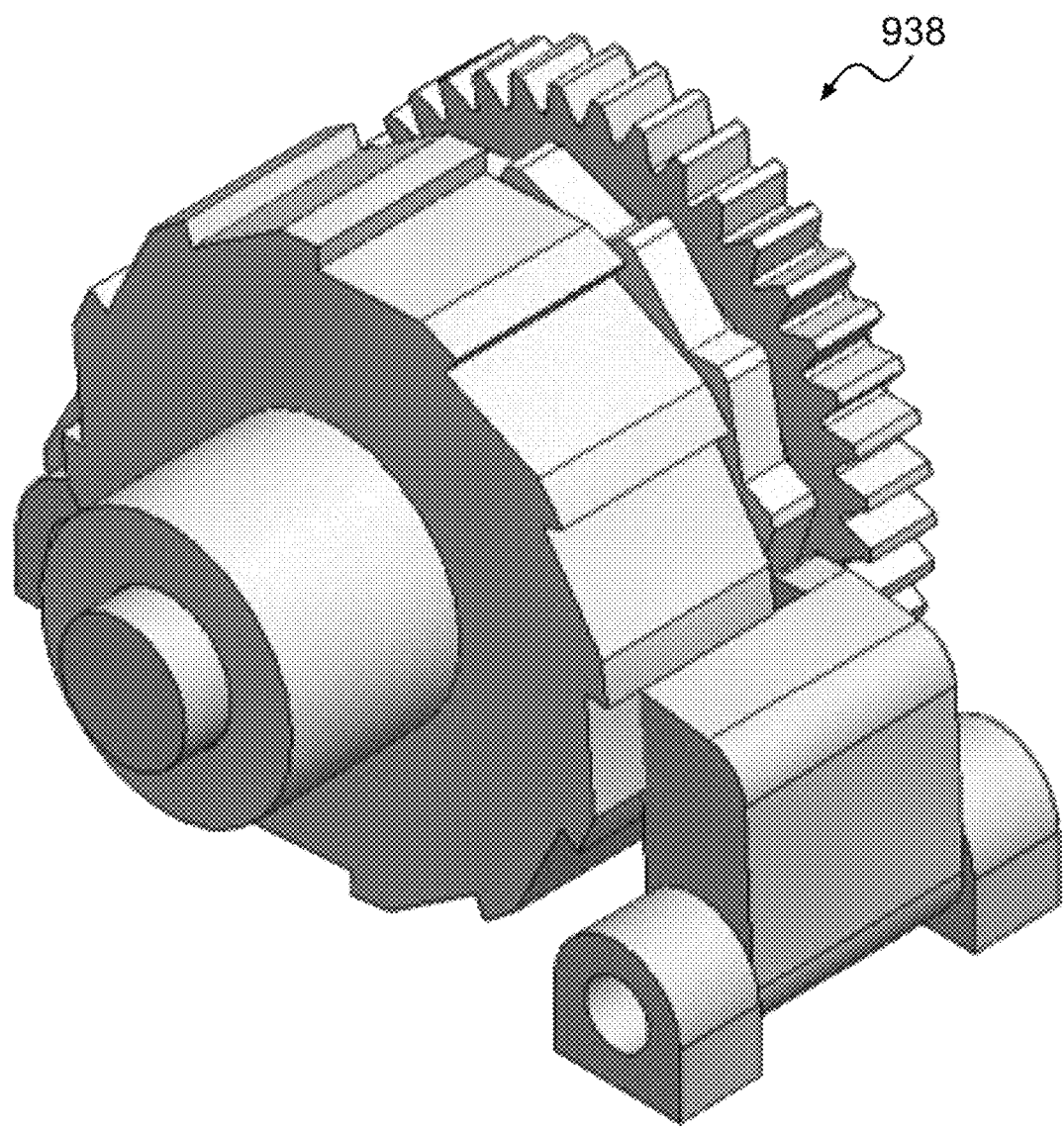
FIG. 47 is an isometric view of another embodiment of a load holding mechanism for a motorized tensioning device.

FIGS. 44 and 45 illustrate schematic views of an alternative tensioning and release mechanism that could be used with a motorized tightening system. Another view of this mechanism is also shown in FIG. 47. For purposes of reference, this mechanism is shown in isolation from other components of a tightening device. This mechanism can be used for accomplishing tightening, load holding, incremental release and full release.

In this design, a system of cams and latches are used. Referring to FIGS. 44 and 45, load holding mechanism 938 includes a final stage output gear 940 of a gear reduction system (not shown) which is connected to a cylindrical plate 942 that has a single driving pawl 944 near its center. In the tightening direction, the motor is continually driven and the pawl 944 drives via detents in an output ring 946 that is attached to the spool. This output ring 946 has internal detents 948 that plate 942 drives and external female teeth 950 that engage an external load holding pawl 954. When the motor is stopped the external load holding pawl 954 resists the spool torque. It can be seen that plate 942 not only has the internal drive pawl 944 but also has cam elements 945 on its periphery that periodically disengage the external load holding pawl 954. When stopped and holding load the external pawl is engaged 954. Then the cylindrical plate 942 begins to back up for an incremental release. At first the output does not release. Then one of cam elements 945 on plate 942 releases outside load holding pawl 954. When this happens, output ring 946 catches up to pawl 954 and next the load holding pawl 954 engages and the mechanism stops in an incremental load holding position. In this way incremental release is accomplished. For this to operate a limit switch is employed to monitor plate 942 and stop in each incremental release position. In the embodiment shown there are six stop positions or every 60 degrees of rotation. This number can vary based on space requirements and the incremental lace release resolution desired. There could be as few as 1 stop per revolution and as many as 12, for example.

For full release, mechanism 938 must be stopped with both the internal and external pawl released at the same time. There is one more releasing pawl 960 required to accomplish this. In the figure, pawl 960 has three positions. Fully retracted, actuator extended, and releasing cam extended. After tensioning, pawl 960 is fully retracted, as incremental releases are actuated the internal pawl 944 will likely pass this external pawl 960 and set it to the full release position. So when a full release is commanded, the internal pawl 944 will move into a position where both internal and external pawls are lifted and the user can freely extract lace and take off the article while only encountering minimal resistance which is provided by the slack take up mechanism.

Manual Release System

Figure 46:
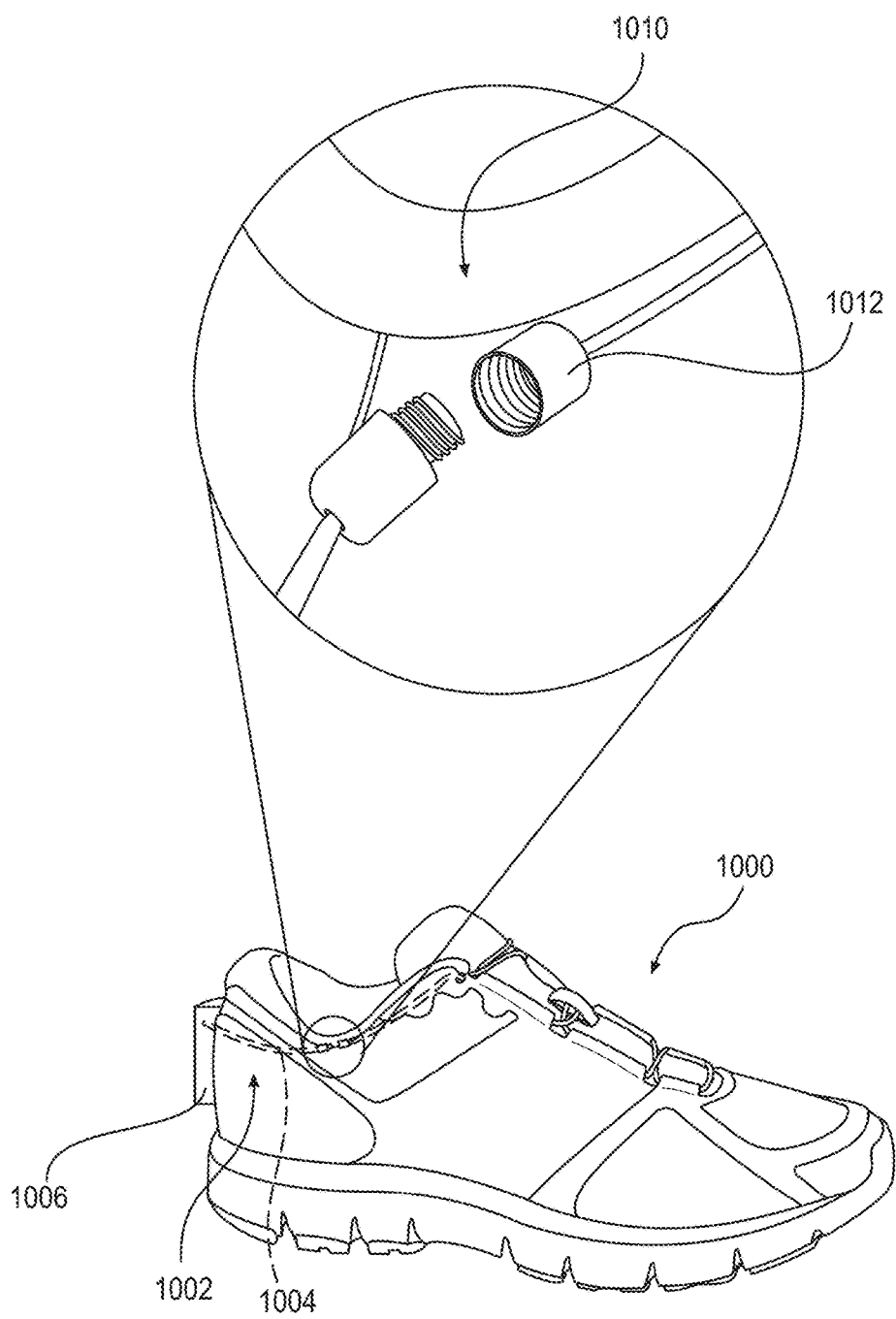
FIG. 46 is a schematic isometric view of an embodiment of a manual release mechanism for a tensioning system including a motorized tensioning device.

FIG. 46 illustrates an embodiment of an alternative manual release system from the system described above. Referring to FIG. 46, article 1000 may be similar to previous embodiments and can include a tensioning system 1002 with a lace 1004 and a motorized tensioning device 1006. In this embodiment, a portion of lace 1004 is equipped with a manual release mechanism 1010. In the embodiment shown here, manual release mechanism 1010 includes corresponding fasteners 1012 that can be manually disconnected to relieve lace tension. In some cases, fasteners 1012 comprise a screw together clasp. However, other embodiments could utilized any other fastening provisions including a snap fit connector, a hook and receiver type connector, or any other kinds of fasteners known in the art.

Medical Braces

Embodiments of a tensioning system, including a motorized tightening device may be incorporated into medical braces or other medical protective wear. Examples of different types of braces include, but are not limited to: wrist braces, arm braces, leg braces, knee braces, ankle braces, as well as any other kinds of braces and protective wear. In one embodiment, a motorized tightening device may be incorporated into the lacing system for a medial brace disclosed in Nickel et al., U.S. Patent Application Publication Number 2012/0004587, now U.S. patent application Ser. No. 13/174,533, filed Jun. 30, 2011 and titled "Braces Using Lacing Systems" (the "Braces application"), the entirety of which is hereby incorporated by reference. For example, a motorized tightening device, including various embodiments described here, could be incorporated into a wrist brace or ankle brace, which are described with various manual tightening systems in the Braces application. A motorized tightening device could also be incorporated into the closure system of the orthopedic braces and protective wear disclosed in Hammersiag et al., U.S. Patent Application Publication Number 2008/0066272, now U.S. patent application Ser. No. 11/854,522, filed Sep. 12, 2007 and titled "Closure System for Braces, Protective Wear and Similar Articles" (the "Protective Wear application"), the entirety of which is hereby incorporated by reference. For example, a motorized tightening device could be incorporated into any of the orthopedic devices (such as knee braces and leg braces) that are described with various manual tightening systems in the Protective Wear application. Various exemplary types of braces incorporating tensioning systems with motorized tightening devices are shown in FIGS. 48-52.

As with footwear and other articles, using a motorized tightening device for a lacing or tensioning system on a brace may provide benefits over manual tightening methods. For example, having a repeatable (measurable) closure may allow a doctor to prescribe a particular tension setting for the brace, allowing the tensioning to act as a repeatable "dosage". Moreover, repeatable closure may improve ease of use allowing a user to put on the brace, press a button and have the brace automatically adjust to the predetermined tension.

It is contemplated that in embodiments including medical braces the "dosing" of the brace tension could be digitally transmitted to a doctor and/or received digitally (at the device) by a doctor. This allows a doctor to efficiently monitor tension, especially as changes may occur due to stretch of the brace, changes in body size, as well as possibly other factors. This also may allow a doctor to tighten the brace (or recommend a tensioning level to the patient) according to a dose level and keep it there over time and as changes occur.

Figure 50:
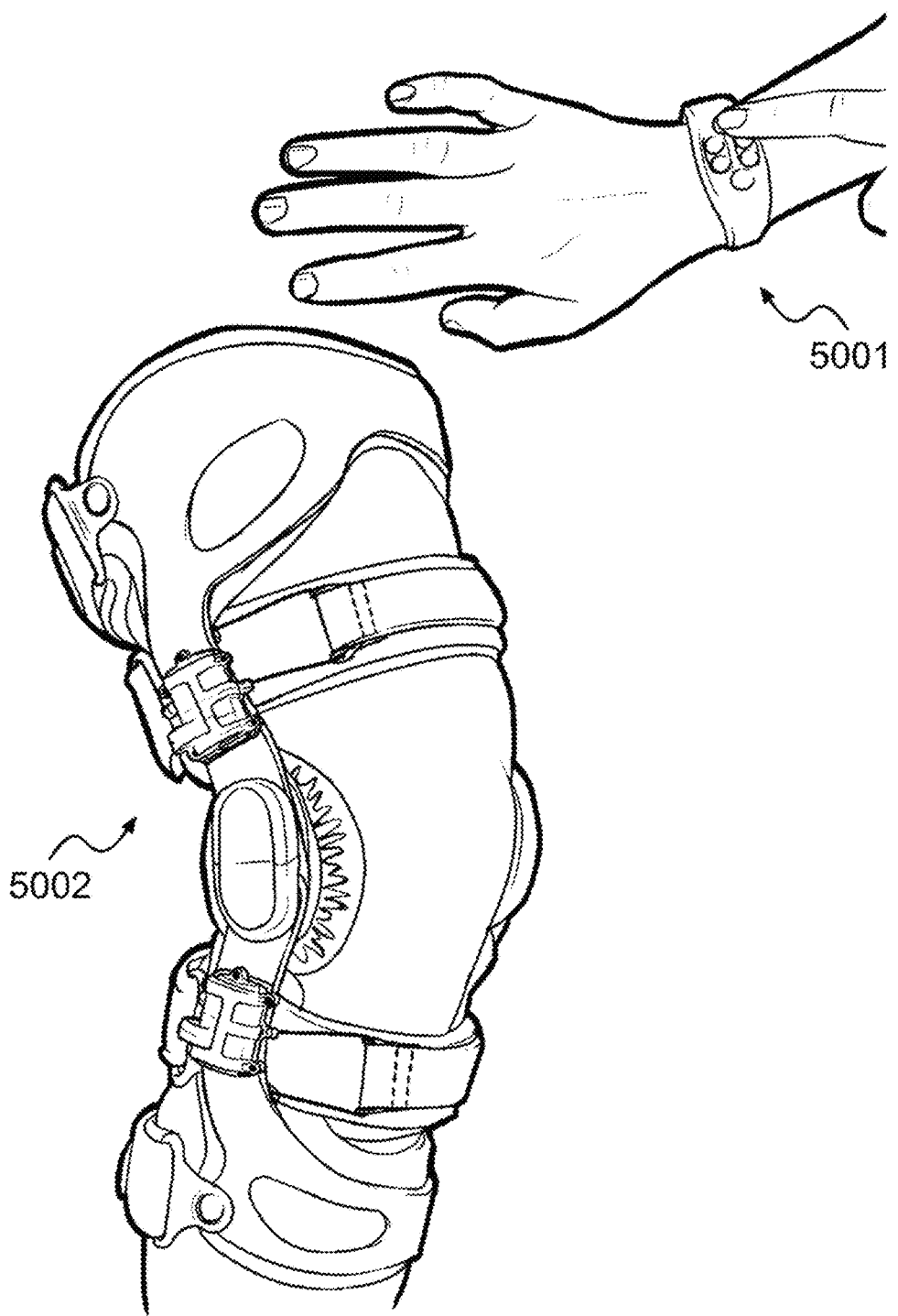
FIG. 50 illustrates an exemplary remote interface for tightening a knee brace.

Using a motorized tensioning device may remove dexterity issues that may occur with other tensioning technologies (pulling straps, Velcro, etc. . . . ). Such a design could improve the use of braces for physically impaired, or injured individuals who may otherwise have a hard time putting on and adjusting their braces. Using the designs proposed here, a brace could be tightened via a push button or remote interface. An exemplary remote interface 5001 for tightening a knee brace 5002 is shown in FIG. 50.

In some embodiments, a brace incorporating a motorized tensioning device can be configured to constantly measure internal system tension and then react to maintain a predetermined tension level. This may help reduce over-tensioning of the device. This may also help in automatically adjusting the brace to a limb as it shrinks from swelling reduction and/or atrophy. In some embodiments, the brace could adjust to provide additional support when/if the brace detects unusually high tensions due to a user falling on the injured limb.

Still additional elements can be added to a brace to aid in reactivity. For example, in some embodiments, a member within the brace that is able to shorten and stiffen at either prescribed times, or when additional support is needed. Such a feature could be accomplished using the motorized tensioning technology as well as possibly other provisions.

A motorized tension device used to tension a brace can also facilitate proactive adjustment of the brace. For example, motorized compression can be used for proactively adjusting compression of a bracing product. In one example, a motorized tensioning device may automatically adjust the tension in a brace at timed intervals, which can encourage blood flow and promote healing. As another example, a motorized tensioning device may automatically adjust tension to correspond with the position of a patient's body or activity. For instance, one level of tensioning could be provided for sitting, a second level of tensioning could be provided for standing and a third level of tensioning could be provided for activities such as walking, running or other ambulatory activities, sitting require one level of protection/support/tension An additional provision that could be used with a brace incorporating a motorized tensioning device for adjusting tensioning in a lace or other tensioning member include a spring based opening. In particular, some embodiments may include a spring between eyestays to keep the brace open when the brace is not in tension. This may make it easier to put the brace on and/or remove the brace. Additionally, this spring based opening may reduce lace tangling issues by proactively keeping lace pulled out of the tensioning device once tension has been released.

Figure 51:
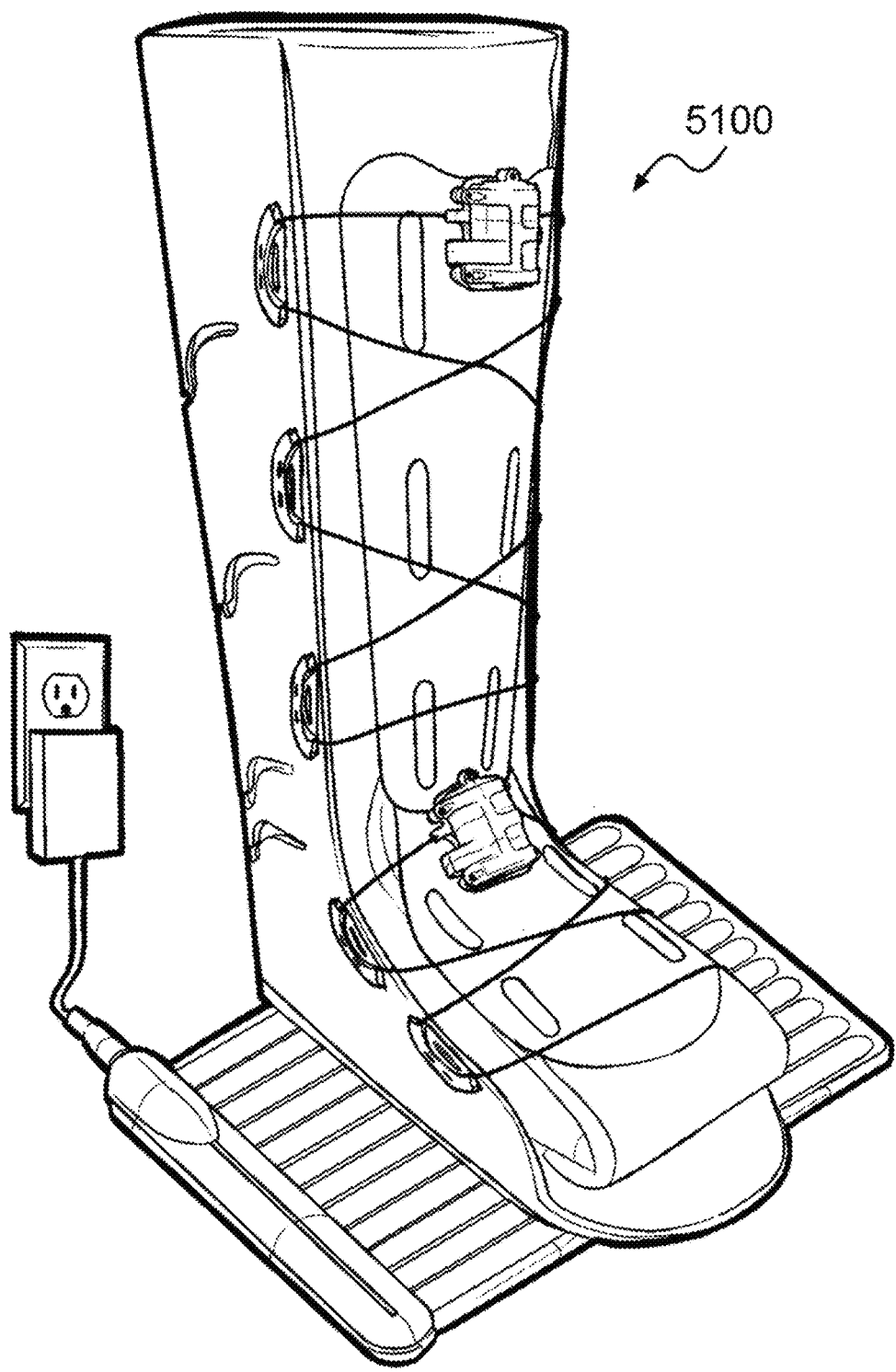
FIG. 51 illustrates an inductive charging configuration for a brace.

Various charging strategies could be employed for a medical brace including inductive charging, plug in charging as well as the use of removable batteries. An example of an inductive charging configuration 5100 for a brace is shown in FIG. 51.

Figure 49:
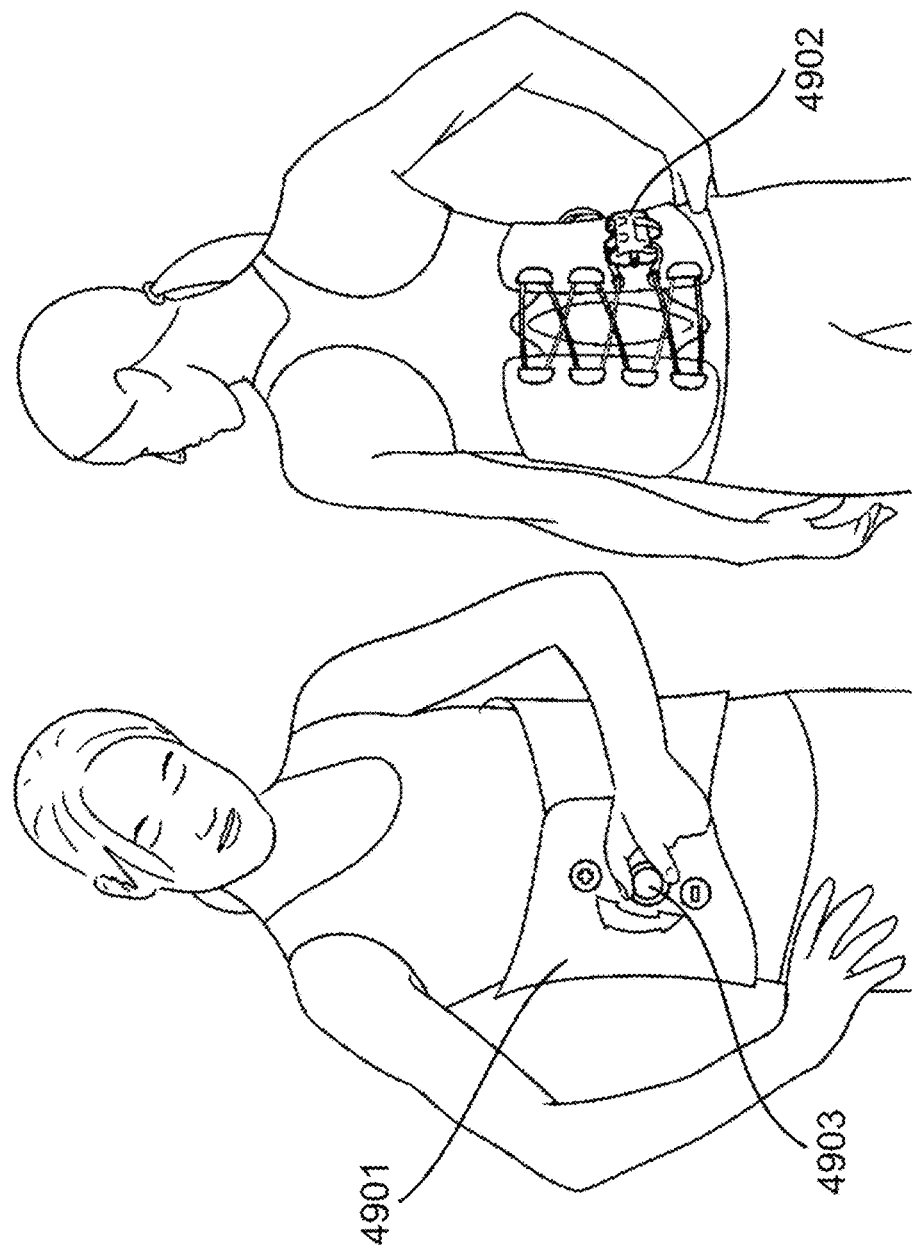
FIG. 49 illustrates an exemplary user interface including a dial for tightening or loosening tension.
Figure 52:
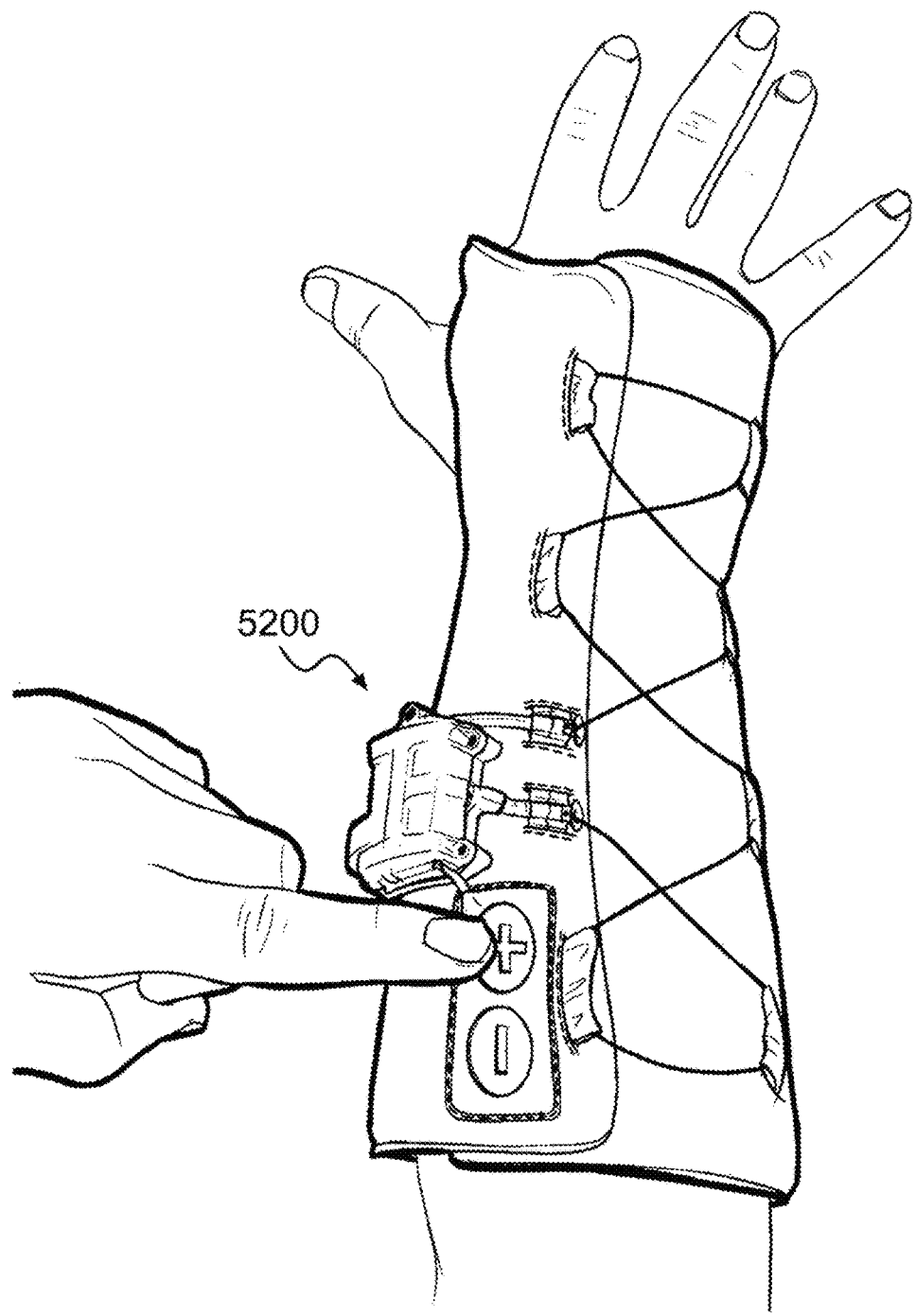
FIG. 52 illustrates a user interface for a motorized tightening device, the interface including a conductive panel.

Examples of user interfaces include a turn dial for tightening or loosening the tension. An exemplary configuration of a back brace 4901 with a motorized tightening device 4902 that uses a turn dial type user control 4903 is shown in FIG. 49. Another possible interface includes a conductive panel where a user moves their finger up or down to adjust tensioning. FIG. 52 shows one such interface for motorized tightening device 5200. Still another interface could be a push button interface.

Methods of digitally tracking tensioning data measured by one or more sensors could be used in some embodiments. The average tension of the device could also be tracked, to measure swelling, atrophy, etc. In addition, in some cases, the number of times the brace is put on and taken off can be tracked. Time of use and the level of patient compliance could also be tracked.

Figure 48:
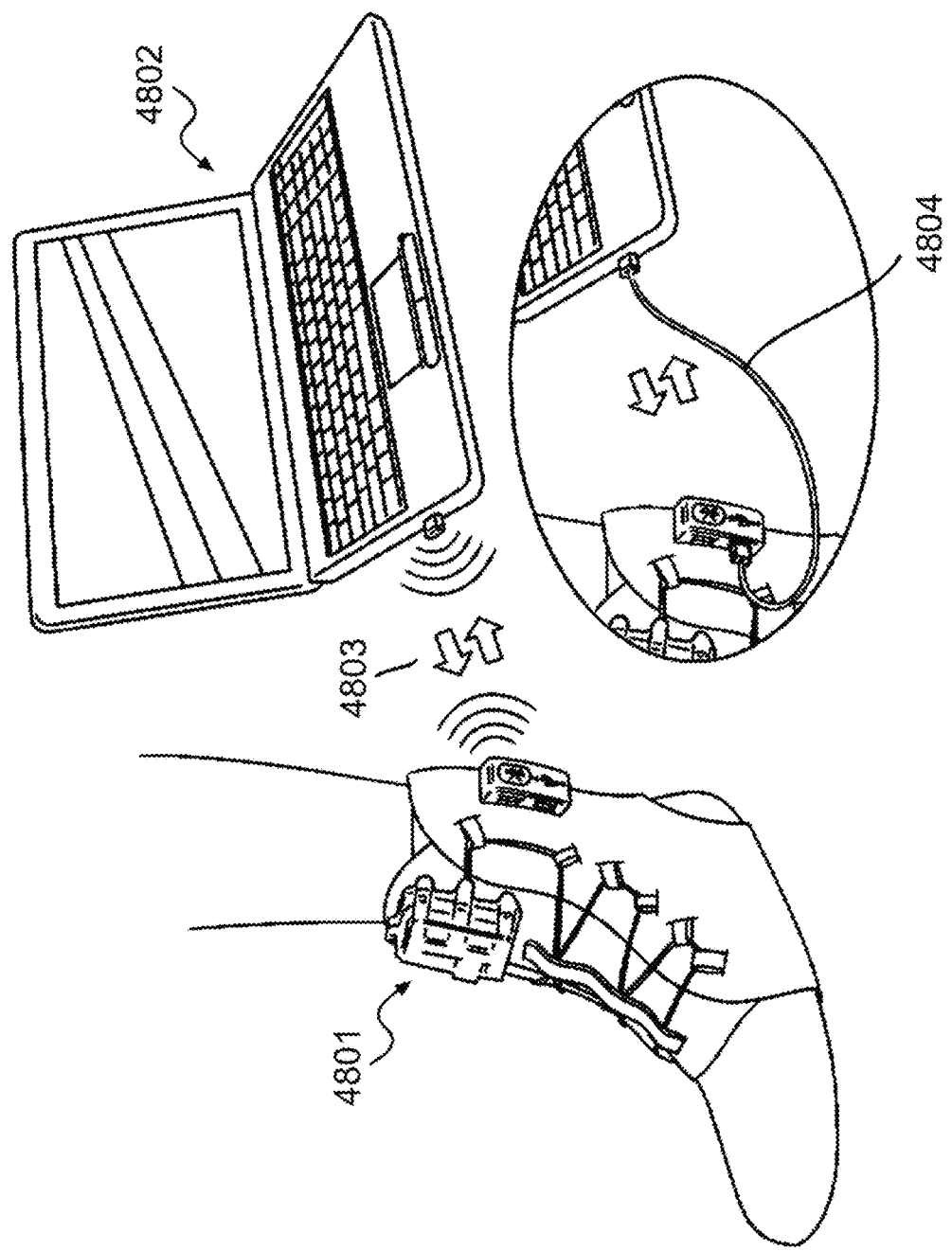
FIG. 48 illustrates exemplary communication modes between a tightening system and a computer.

Data collection could be facilitated by various technologies including USB devices, data cords and blue tooth communication technologies. Moreover, the data collected can be transmitted through a variety of technologies to either a central database for evaluation, and/or directly to a physician to allow them to monitor the progress of a patient. FIG. 48 shows exemplary communication modes between a tightening system 4801 and a computer 4802, including a Bluetooth connection 4803 and a USB connection 4804.

While various embodiments of the embodiments have been described, the description is intended to be exemplary, rather than limiting and it will be apparent to those of ordinary skill in the art that many more embodiments and implementations are possible that are within the scope of the embodiments. Accordingly, the embodiments are not to be restricted except in light of the attached claims and their equivalents. Also, various modifications and changes may be made within the scope of the attached claims.

What is claimed is:

1. A footwear tension control system, comprising:
an article of footwear including a tensioning member;
a motorized tensioning device for adjusting tension in the tensioning member;
a user control system in communication with the motorized tensioning device, wherein the user control system includes inputs that provide commands to the motorized tensioning device;
wherein the user control system includes a footwear selection input, the footwear selection input allowing the user to select between sending commands to a left article of footwear or a right article of footwear;
wherein the user control system includes a tighten input; and
wherein the user control system includes a loosen input.

2. The footwear tension control system according to claim 1, wherein the user control system includes a tension storing input.

3. The footwear tension control system according to claim 1, wherein the user control system includes a tension recall input.

4. The footwear tension control system according to claim 1, wherein the user control system comprises a software application configured to run on a control device.

5. The footwear tension control system according to claim 4, wherein the software application provides information related to one or more inputs that can be displayed as an indicia on a display of the control device.

6. The footwear tension control system according to claim 5, wherein the software application includes a left foot indicia and a right foot indicia associated with the footwear selection input.

7. The footwear tension control system according to claim 1, wherein the user control system includes an input for fully releasing tension of the tensioning member.

8. The footwear tension control system according to claim 1, wherein the tensioning member is configured to pass through lacing guides along a throat opening of the article of footwear.

9. The footwear tension control system according to claim 1, wherein the control device can be a remote device.

10. A footwear tension control system, comprising:
an article of footwear including a tensioning member;
wherein the tensioning member is disposed adjacent a throat opening of the article of footwear;
a motorized tensioning device for adjusting tension in the tensioning member;
a user control system in communication with the motorized tensioning device, wherein the user control system includes inputs that provide commands to the motorized tensioning device;
wherein the user control system includes a footwear selection input, the footwear selection input allowing the user to select between sending commands to a left article of footwear or a right article of footwear;
wherein the user control system includes a tighten input; and
wherein the user control system includes a loosen input.

11. The footwear tension control system according to claim 10, wherein the motorized tensioning device tightens the tensioning member and constricts the throat opening.

12. The footwear tension control system according to claim 10, wherein the motorized tensioning device loosens the tensioning member and expands the throat opening.

13. The footwear tension control system according to claim 10, wherein the motorized tensioning device incrementally adjusts tension in the tensioning member.

14. A footwear tension control system, comprising:
an article of footwear including a tensioning member;
a motorized tensioning device for adjusting tension in the tensioning member;
a user control system in communication with the motorized tensioning device, wherein the user control system includes inputs that provide commands to the motorized tensioning device;

wherein the user control system includes a footwear selection input;

wherein the user control system includes an incremental tighten input;

wherein the user control system includes an incremental loosen input; and wherein the user control system includes a fully loosen input.

15. The footwear tension control system according to claim 14, wherein the user control system includes a store tension input.

16. The footwear tension control system according to claim 15, wherein the user control system includes a return to stored tension input.

17. The footwear tension control system according to claim 15, wherein the store tension input can store two or more tension settings.

18. The footwear tension control system according to claim 17, wherein the two or more tension settings correspond to at least two different tension preferences of the tensioning member.

19. The footwear tension control system according to claim 14, wherein the motorized tensioning device adjusts tension in the tensioning member in a continuous manner.

20. The footwear tension control system according to claim 14, wherein the motorized tensioning device adjusts tension in the tensioning member in discrete steps.

* * * * *